(12) United States Patent
Kono et al.

(10) Patent No.: US 9,376,467 B2
(45) Date of Patent: Jun. 28, 2016

(54) CROSS-LINKED PEPTIDES CONTAINING NON-PEPTIDE CROSS-LINKED STRUCTURE, METHOD FOR SYNTHESIZING CROSS-LINKED PEPTIDES, AND NOVEL ORGANIC COMPOUND USED IN METHOD

(75) Inventors: Yusuke Kono, Tokyo (JP); Shuji Fujita, Tokyo (JP); Hideaki Suzuki, Tokyo (JP); Mari Okumoto, Tokyo (JP); Takashi Nakae, Tokyo (JP); Kazuhiro Chiba, Tokyo (JP)

(73) Assignee: JITSUBO CO., LTD., Tokyo (JP)

( * ) Notice: Subject to any disclaimer, the term of this patent is extended or adjusted under 35 U.S.C. 154(b) by 0 days.

(21) Appl. No.: 14/004,058

(22) PCT Filed: Feb. 28, 2012

(86) PCT No.: PCT/JP2012/054895
§ 371 (c)(1),
(2), (4) Date: Sep. 9, 2013

(87) PCT Pub. No.: WO2012/121057
PCT Pub. Date: Sep. 13, 2012

(65) Prior Publication Data
US 2013/0345393 A1 Dec. 26, 2013

(30) Foreign Application Priority Data
Mar. 9, 2011 (JP) .................. 2011-052107

(51) Int. Cl.
*C07K 7/08* (2006.01)
*A61K 47/48* (2006.01)
*C07K 1/00* (2006.01)
*C07K 1/113* (2006.01)
*C07K 7/06* (2006.01)
*C07K 14/00* (2006.01)

(52) U.S. Cl.
CPC ............. *C07K 7/08* (2013.01); *A61K 47/48215* (2013.01); *C07K 1/006* (2013.01); *C07K 1/113* (2013.01); *C07K 7/06* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 5,610,141 A | 3/1997 | Undheim et al. |
| 6,143,722 A | 11/2000 | Merlin et al. |
| 6,608,027 B1 | 8/2003 | Tsantrizos et al. |
| 6,682,739 B1 | 1/2004 | Greene et al. |
| 8,093,435 B2 | 1/2012 | Chiba et al. |
| 2010/0029904 A1 | 2/2010 | Chiba et al. |
| 2010/0249374 A1 | 9/2010 | Takahashi |

FOREIGN PATENT DOCUMENTS

| | | |
|---|---|---|
| JP | 2004-059509 | 2/2004 |
| WO | WO 93/24523 A1 | 12/1993 |
| WO | 98/53842 | 12/1998 |
| WO | WO 2005-030796 | 4/2005 |
| WO | WO 2009-058856 | 5/2009 |
| WO | 2011/008260 A2 | 1/2011 |

OTHER PUBLICATIONS

Aoki et al.,J. of Clin. Invest., 2006, 116(6), 1525-1534.*
Aoki et al., J. of Clin. Chem., 2006, 116(6), 1525-1534.*
Schafmeister et al., J. Am. Chem. Soc., 2000, 122, 5891-5892.*
Brik, Adv. Synth. Catal., 2008, 350, 1661-1675.*
Taylor, Bioplymers (Peptide Science), 2002, 66, 49-75.*
Taylor, Biopolymers(Peptide Science), 2002, 66, 49-75.*
Arnold, Lee D., et al. "Synthesis of Optically Pure α-Amino Acids via Salts of α-Amino-β-propioloactone," J. Am. Chem. Soci., 110, pp. 2237-2241 (1988).
Arnold, Lee D., et al. "Conversion of Serine to Stereochemically Pure β-Substituted β-Amino Acids via β-Lactones," J. Am. Chem. Soci., 107, pp. 7105-7109 (1985).
Bregant, Sarah, et al. "Orthogonally Protected Lanthionines: Synthesis and Use for the Solid-Phase Synthesis on an Analogue of Nisin Ring C," J. Org. Chem., 70, pp. 2430-2438 (2005).
Liu, Hongqiang, et al. "Stereoselective Syntheses of 4-Oxa Diaminopimelic Acid and Its Protected Derivatives via Aziridine Ring Opening," vol. 9, No. 21, pp. 4211-4214 (2007).
Liu, Hongqiang et al. Synthesis and Biological Activity of Oxa-Lacticin A2, a Lantibiotic Analogue with Sulfur Replaced by Oxygen, vol. 11, No. 24, pp. 5574-5577 (2009).
English translation of the Written Opinion for Application No. PCT/JP2012/054895 mailed on Sep. 10, 2013.
Extended European Search Report issued in European Patent Application No. 12755137.2 dated Dec. 12, 2014.
P.D. Bailey et al., "Synthesis of polycyclic hexapeptides containing multiple intramolecular cross-links", Tetrahedron Letters, 33(22), 1992, 3215-3218.
G. Tana et al., "A practical solution-phase synthesis of an antagonistic peptide of TNF-α based on hydrophobic tag strategy†", Chem. Commun., 46, 2010, 8219-8221.
H.I. Mosberg et al. "Bis-penicillamine enkephalins posses highly improved specificity toward o opioid receptors," Proc. Natl. Acad. Sci. 80:5871-5874 (1983).
D. Flora et al. "Detection and control of aspartimide formation in the synthesis of cyclic peeptides," Bioorg. Med. Chem. Lett. 15:1065-1068 (2005).
C.E. Schafmeister et al. "An All-Hydrocarbon Cross-Linking System for Enhancing the Helicity and Metabolic Stability of Peptides," J. Am. Chem. Soc. 122:5891-5892 (2000).

(Continued)

*Primary Examiner* — Karlheinz R Skowronek
*Assistant Examiner* — Roy Teller
(74) *Attorney, Agent, or Firm* — Michael Ye; Andrews Kurth, LLP

(57) ABSTRACT

The purpose of the present invention is to provide a cross-linked peptide containing a novel non-peptide cross-linked structure, and a method for synthesizing the same. A cross-linked peptide having a novel non-peptide cross-linked structure, a useful intermediate for synthesizing the cross-linked peptide, and a method for synthesizing the novel cross-linked peptide and the intermediate are provided. The cross-linked peptide is characterized by having an —NR— bond in the cross-linked structure. By using the method for synthesizing the cross-linked peptide, a cross-link can be freely designed and an change can be freely made to a cross-link.

13 Claims, 13 Drawing Sheets

(56) References Cited

OTHER PUBLICATIONS

C. Gilon et al. "Backbone Cyclization: A New Method for Conferring Conformational Constraint on Peptides," Biopolymers 37:745-750 (1991).

D. Scharn et al. "Sequential Nucleophilic Substitution on Halogenated Triazines, Pyrimidines, and Purines: A Novel Approach to Cyclic . . . " J. Org. Chem., 66:507-513 (2001).

M. Goodman et al. "Solid-PHase Synthesis of Amine-Bridged Cyclic Enkephalin Analogues via On-Resin Cyclization . . . " J. Org. Chem., 67:8820-8826 (2002).

K. Aoki et al. "A TNF receptor loop peptide mimic blocks RANK ligand-induced signaling, bone resorption, and bone loss," J. Clin. Invest. 116:1525-1534 (2006).

T. Kojima et al. "Subcutaneous Injections of a TNF-a Anafonistic Peptide Inhibit Both Inflammation and Bone Resortption in . . . " J. Med. Dent. Sci, vol. 52, No. 1: 91-99 (2005).

K. Aoki et al. "RANKL/RANK signaling-inhibitor," Japanese Journal of Clinical Medine, vol. 63, No. 9:1620-1626 (2005).

S. Kitada et al. "Development of Synthesis method for cyclic peptide . . . " Annual Meet. of Japan Soc. for Bioscience, Biotech. & Agrochem., vol. 2011, p. 190 (2011).

T. Kakune et al. "Studies on practical method for liquid phase synthetic . . . " Annual Meet. of Japan Soc. for Bioscience, Biotech. & Agrochem., vol. 2009, p. 181 (2009).

C. Korner et al. "An expedient synthesis of orthogonally protected lysinalanine from Aloc-protected Garner's aldehyde," Journ. Tetrahedron Letters 51:6381-6383 (2010).

P. Ciapetti et al. "Nucleophilic substitution of Protected 2-Amino-4-Butanoic Acid. An Easy route to exotic Amino . . . " Tetrahedron Letters 39: 3843-3846 (1998).

\* cited by examiner

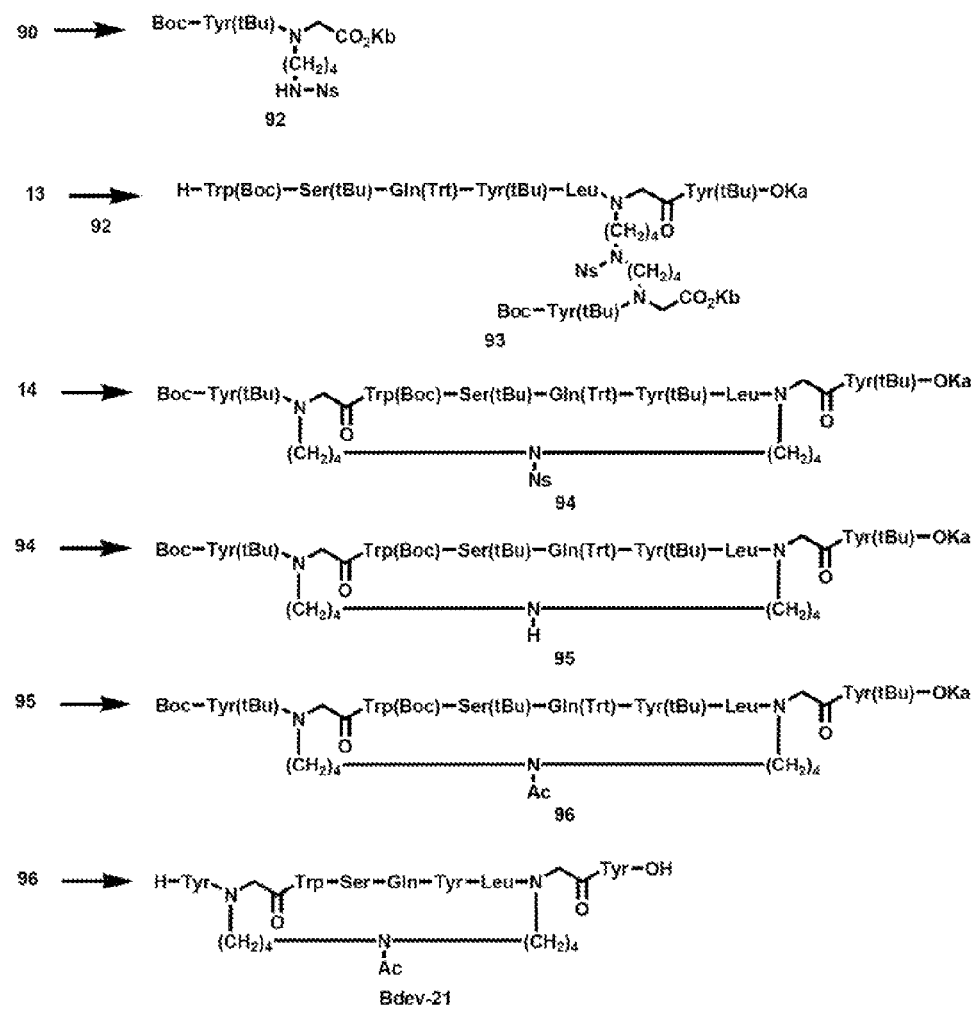

CROSS-LINKED PEPTIDES CONTAINING NON-PEPTIDE CROSS-LINKED STRUCTURE, METHOD FOR SYNTHESIZING CROSS-LINKED PEPTIDES, AND NOVEL ORGANIC COMPOUND USED IN METHOD

This application is a national stage application under 35 U.S.C. §371 of International Application No. PCT/JP2012/054895, filed Feb. 28, 2012, entitled "NOVEL CROSS-LINKED PEPTIDES CONTAINING NON-PEPTIDE CROSS-LINKED STRUCTURE, METHOD FOR SYNTHESIZING CROSS-LINKED PEPTIDES, AND NOVEL ORGANIC COMPOUND USED IN METHOD," which claims priority to Japanese Patent Application No. 2011-052107, filed Mar. 9, 2011, the contents of both of which are hereby incorporated in their entirety by reference.

TECHNICAL FIELD

The present invention relates to a cross-linked peptide containing a novel nonpeptidic cross-linked structure. Also, the present invention relates to a method of synthesizing such a cross-linked peptide. Further, the present invention relates to a novel organic compound used for synthesis of such a cross-linked peptide.

BACKGROUND ART

Almost all physiological processes are based on molecular recognition of peptides or proteins and other biologically active components and the like. A lot of peptides having important biological functions such as hormones, enzymes, inhibitors, enzyme substrates, neurotransmitters, immunomodulators and the like have been found to date. There are resultantly many studies conducted to develop therapeutic means with a peptide, with understanding physiological effects of active substances composed of these peptides.

In development of a peptide as a medicinal product, there are new methods established for treatments and therapies of diseases correlated with peptides, however, in use of a peptide as a medicinal product, problems as described below are generated. That is, a) under physiological conditions, most peptides are decomposed by specific and nonspecific peptidases, to give low metabolic stability, b) due to relatively large molecular weight thereof, absorption after ingestion is poor, c) excretion through liver and kidney is fast, and d) since a peptide is structurally flexible and receptors for a peptide can be distributed widely in an organism, undesired side effects occur in non-targeted tissues and organs.

Except for some examples, relatively small natural peptides (peptide composed of 30 to less than 50 amino acids) are present under disorderly conditions due to a lot of conformations in dynamic equilibrium in a diluted aqueous solution, as a result, the peptides lack in selectivity for a receptor and become liable to undergo metabolism, thus, determination of a biologically active conformation is difficult. When a peptide itself has a biologically active conformation, namely, when having the same conformation as that under condition linked to a receptor, a reduction in entropy in linking to a receptor is smaller as compared with a flexible peptide, consequently, an increase in affinity to a receptor is expected. Therefore, there is a need for a biologically active peptide having a uniformly controlled conformation, and development thereof is important.

There are recently many efforts conducted to develop a peptide mimic or a peptide analog (hereinafter, referred to as "peptide mimic" together) showing a more preferable pharmacological property than that of a natural peptide as the original form thereof. "Peptide mimic" used in the present specification is a compound which is capable of mimicking (agonistic substance) or blocking (antagonistic substance) at receptor level, the biological effect of a peptide, as a ligand of a receptor. For obtaining a peptide mimic as the most possible agonistic substance, factors such as a) metabolic stability, b) excellent bioavailability, c) high receptor affinity and receptor selectivity, d) minimum side effects, and the like should be taken into consideration. From the pharmacological and medical standpoint, it is often desirable not only to mimic the effect of a peptide at receptor level (agonistic action) but also, if necessary, to block a receptor (antagonistic action). The same items as the pharmacological items which should be considered for designing a peptide mimic as the above-described agonistic substance can be applied also to designing of a peptide antagonistic substance.

One example of peptide mimics is development of a peptide having a controlled conformation. This mimics, as correctly as possible, a conformation linked to a receptor of an endogenic peptide ligand. When analogs of these types are investigated, resistance to a protease increases, and resultantly, metabolic stability rises and selectivity rises, thereby lowering side effects.

Overall control in the conformation of a peptide is possible by restricting flexibility of a peptide chain by cyclization. Cyclization of a biologically active peptide not only improves its metabolic stability and selectivity for a receptor but also gives a uniform conformation, thereby enabling analysis of the conformation of a peptide. The cyclization form is the same as that observed in natural cyclic peptides. Examples thereof include side chain-side chain cyclization, or side chain-end group cyclization. For cyclization, side chains of amino acids not correlated with receptor recognition can be mutually linked, or can be linked to the peptide main chain. As another embodiment, there is head to tail cyclization, and in this case, a completely cyclic peptide is obtained.

For these cyclization operations, a cross-linking technology is imperative. Typical examples of cyclization include cross-linkages via a disulfide bond (SS bond), an amide bond, a thioether bond and an olefin bond. More specific examples thereof include cyclization by connecting two penicillamine residues via a disulfide cross-linkage (Mosberg et al., P.N.A.S. US, 80:5871, 1983), cyclization by forming an amide bond between lysine and aspartic acid (Flora et al., Bioorg. Med. Chem. Lett. 15 (2005) 1065-1068), a procedure in which an amino acid derivative containing a cross-linked portion having a thioether bond introduced previously is introduced into a peptide bond and cyclization thereof is performed in the last condensation reaction (Melin et al., U.S. Pat. No. 6,143,722), and cyclization by mutually cross-linking (S)-α-2'-pentenylalanines introduced into the main chain using an olefin metathesis reaction (Schafmeister et al., J. Am. Chem. Soc., 122, 5891-5892, 2000).

A cross-linkage via a disulfide bond, however, will be cleaved by a reductase generally present in an organism. Also, a cross-linkage via an amide bond will be cleaved by an enzyme cutting an amide structure present in an organism. A thioether bond and an olefin bond need substitution of side chains of an amino acid in a peptide elongation process, for attaining cyclization thereof.

Also known is a cross-linked structure originating from nitrogen constituting an amide in the peptide main chain skeleton, as a method needing no modification of a side chain of a peptide (Gilon et al., Biopolymers 31:745, 1991). However, this peptide will be cleaved by an enzyme cutting an amide structure, because of inclusion of an amide bond in this peptide.

Further, known as a cross-linked peptide having a molecular structure capable of linking to other substituent is a cross-linked peptide utilizing 2,4,6-trichloro[1,3,5]-triazine (Scharn et al., J. Org. Chem. 2001, 66, 507-513). In this method, however, the reaction in forming a cross-linked portion is an aromatic nucleophilic substitution reaction, thereby limiting applicable peptides.

As the analogous peptide, a cross-linked peptide in which a side chain and a carboxy terminus are linked is known (Goodman et al., J. Org. Chem. 2002, 67, 8820-8826). This peptide, however, will be cleaved by an enzyme cutting an amide structure, because of inclusion of an amide bond in this peptide.

A peptide having a controlled conformation is expected to provide a lot of pharmacological use applications. For example, somatostatin is a cyclic tetradecapeptide present in both the central nerve system and surrounding tissues and has been identified as an important inhibitor against secretion of a grow hormone from pituitary gland, and additionally, has functions such as suppression of secretion of glucagon and insulin from spleen, regulation of most gastrointestinal hormones, regulation of release of other neurotransmitters correlated with motor activity and a recognition process all over the central nerve system, and the like. A cross-linked peptide composed of nine amino acids called a WP9QY (W9) peptide mimicking the steric structure of a contact site between TNF and a TNF receptor suppresses the inflammation activity of TNFa, and additionally, is known to suppress bone resorption (Aoki et al., J. Clin. Invest. 2006; 116(6):1525-1534).

There is a study conducted to obtain a peptide mimic having metabolic stability improved by adding to the peptide a structure not present in natural peptides, as the peptide mimic showing a more preferable pharmacological property than that of a natural peptide as the original form thereof, in addition to a cross-linked peptide having a conformation controlled as described above. For example, resistance to an enzyme is improved by using cross-linkages (a cross-linkage via a thioether bond, a cross-linkage via an olefin, and the like) other than the above-described natural cross-linking (disulfide cross-linkage). Further, resistance to metabolism in an organism is improved by adding, for example, PEG and the like, to the terminus or the side chain of a peptide.

JP-A No. 2004-59509, compounds described in PCT international publication WO2007/034812, compounds described in PCT international publication WO2007/122847, compounds described in PCT international publication WO2010/104169 and compounds described in PCT international publication WO2010/113939

CITED REFERENCE

Patent Documents

Patent document 1: U.S. Pat. No. 6,143,722
Patent document 2: JP Laid-Open Application No. 2004-59509
Patent document 3: PCT international publication WO2007/034812
Patent document 4: PCT international publication WO2007/122847
Patent document 5: PCT international publication WO2010/113939

Non-Patent Documents

Non-patent document 1: Mosberg et al., P.N.A.S. US, 80:5871, 1983
Non-patent document 2: Flora et al., Bioorg. Med. Chem. Lett. 15(2005) 1065-1068
Non-patent document 3: Schafmeister et al., J. Am. Chem. Soc., 122, 5891-5892, 2000
Non-patent document 4: Gilon et al., Biopolymers 31:745, 1991
Non-patent document 5: Scharn et al., J. Org. Chem. 2001, 66, 507-513
Non-patent document 6: Goodman et al., J. Org. Chem. 2002, 67, 8820-8826
Non-patent document 7: Aoki et al., J. Clin. Invest. 2006; 116(6):1525-1534

SUMMARY OF THE INVENTION

Technical Problem

However, introduction of a functional molecule has often damaged the pharmacological function intrinsically owned by a peptide. There has been desired a cross-linking method capable of producing a cross-linked peptide while simply carrying out the elongation reaction of a peptide and forming a cross-linking bond at any site. Further, a cross-linking method has been desired which can optionally perform substitution and other alterations also in the cross-linked structure.

One object of the present invention is to provide a cross-linked peptide containing a new cross-linked structure or a peptide mimic having the new cross-linked structure.

Another object of the present invention is to provide a cross-linking method capable of producing a cross-linked peptide or a peptide mimic, which can perform a peptide elongation reaction in a liquid phase and can form a cross-linked bond at any site.

Still another object of the present invention is to provide a cross-linked structure in which substitution and other alterations can be optionally performed also in the cross-linked structure, and a cross-linked peptide or a peptide mimic containing such a structure.

Even still another object of the present invention is to provide a cross-linking method capable of producing a cross-linked peptide or a peptide mimic containing a cross-linked structure in which substitution and other alterations can be optionally performed also in the cross-linked structure.

The other object of the present invention is to provide a novel cross-linked peptide in which resistance to a peptidase and the like is improved or a peptide mimic having the novel cross-linked structure.

Solution of Problem

The present inventors have intensively studied to solve the above-described problems and resultantly succeeded in synthesizing a cross-linked peptide containing a novel nonpeptidic cross-linked structure by using a novel organic compound having a cross-linked structure in the molecule, leading to completion of the present invention.

That is, the present invention provides novel cross-linked peptides, novel compounds and methods of synthesizing these cross-linked peptides, described below.

The present invention provides:
1. A cross-linked peptide represented by the following chemical formula:

[chemical formula 1]

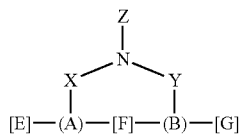

(wherein, X and Y represent each independently an alkylene chain having 1 to 12 carbon atoms or an alkylene chain having 1 to 66 carbon atoms containing at least one —O—, —NH— or —S-bond (optionally substituted by a divalent oxygen atom or sulfur atom), Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group, [E] represents a hydrogen atom, an optionally substituted acyl group having 1 to 6 carbon atoms or a peptide having 1 to 20 residues composed of amino acids and/or unnatural amino acids as constituent elements, [G] represents OH, an amino group or a peptide having 1 to 20 residues composed of amino acids and/or unnatural amino acids as constituent elements, [F] represents a peptide having 1 to 20 residues composed of amino acids and/or unnatural amino acids as constituent elements (here, the sum of the numbers of amino acids of [E], [F] and [G] is at least 3), and (A) and (B) represent each independently a structure represented by any of the following formula:

[chemical formula 2]

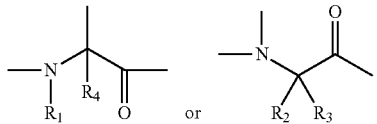

(wherein, $R_1$, $R_3$ and $R_4$ represent each independently a hydrogen atom or a methyl group, and $R_2$ represents a hydrogen atom or a side chain of an amino acid or unnatural amino acid.));

2. The cross-linked peptide according to [1] represented by the following formula:

[chemical formula 3]

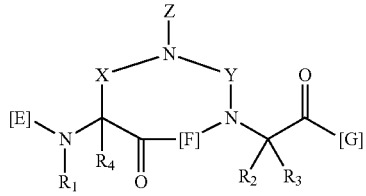

(wherein, X represents an alkylene chain having 1 to 12 carbon atoms or an alkylene chain having 1 to 66 carbon atoms containing at least one —O— or —S-bond, Y represents an alkylene chain having 1 to 12 carbon atoms or an alkylene chain having 1 to 66 carbon atoms containing at least one —O—, —NH— or —S-bond (optionally substituted by a divalent oxygen atom or sulfur atom), and Z, [E], [F], [G], $R_1$, $R_2$, $R_3$ and $R_4$ are as described above.);

3. The cross-linked peptide according to [1] represented by the following formula:

[chemical formula 4]

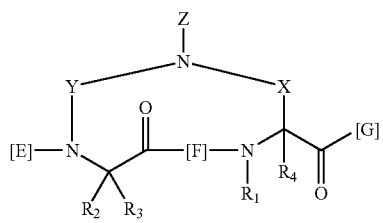

(wherein, X represents an alkylene chain having 1 to 12 carbon atoms or an alkylene chain having 1 to 66 carbon atoms containing at least one —O— or —S-bond, Y represents an alkylene chain having 1 to 12 carbon atoms or an alkylene chain having 1 to 66 carbon atoms containing at least one —O—, —NH— or —S-bond (optionally substituted by a divalent oxygen atom or sulfur atom), and Z, [E], [F], [G], $R_1$, $R_2$, $R_3$ and $R_4$ are as described above.);

4. The cross-linked peptide according to [1] represented by the following formula:

[chemical formula 5]

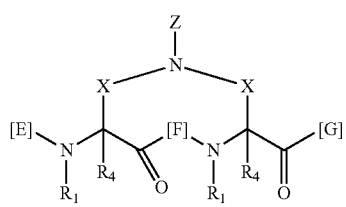

(wherein, X represents an alkylene chain having 1 to 12 carbon atoms or an alkylene chain having 1 to 66 carbon atoms containing at least one —O— or —S-bond, and Z, [E], [F], [G], $R_1$ and $R_4$ are as described above. Here, Xs, $R_1$ s or $R_4$ s in the chemical formula may each be the same or different.);

5. The cross-linked peptide according to [1] represented by the following formula:

[chemical formula 6]

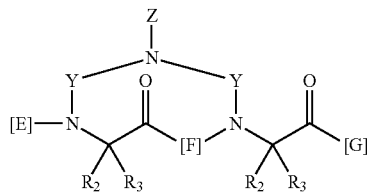

(wherein, Y represents an alkylene chain having 1 to 12 carbon atoms or an alkylene chain having 1 to 66 carbon atoms containing at least one —O—, —NH— or —S-bond (optionally substituted by a divalent oxygen atom or sulfur atom), and Z, [E], [F], [G], $R_2$ and $R_3$ are as described above. Here, Ys, $R_2$ s or $R_3$ s in the chemical formula may each be the same or different.);

6. The cross-linked peptide according to any one of [1] to [5], wherein X is selected from the group consisting of the following chemical formulae:

[chemical formula 7]

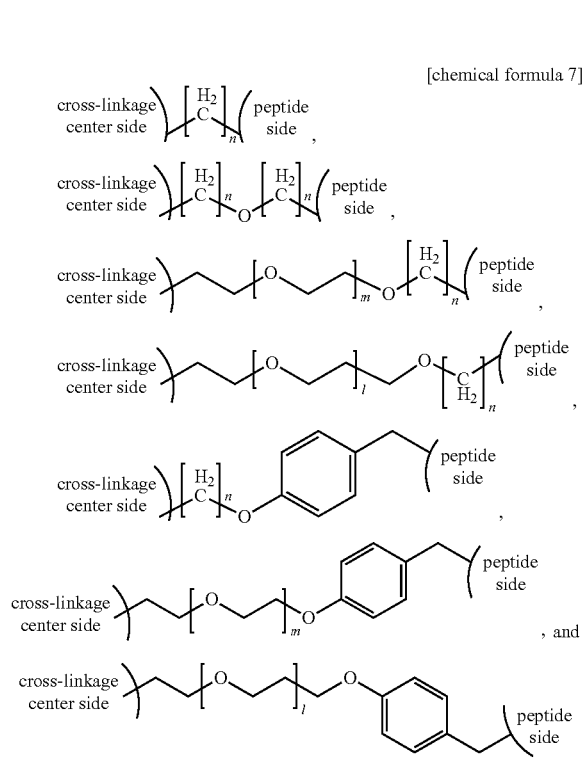

(wherein, n represents an integer of 1 to 12, m represents an integer of 1 to 24 and l represents an integer of 1 to 24.);

7. The cross-linked peptide according to any one of [1] to [6], wherein Y is any one selected from the group consisting of the following compound Y1, compound Y2, compound Y3, compound Y4 and compound Y5:

(Compound Y1)

[chemical formula 8]

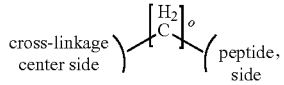

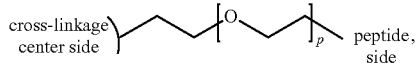

(Compound Y2)

[chemical formula 9]

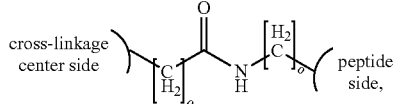

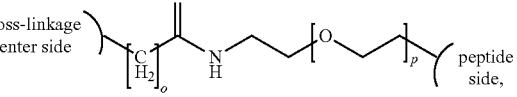

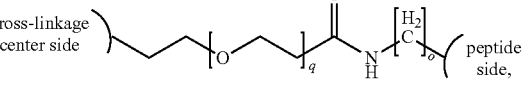

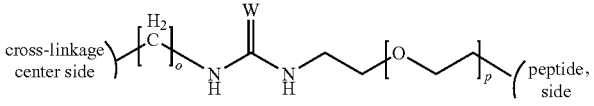

(Compound Y3)

[chemical formula 10]

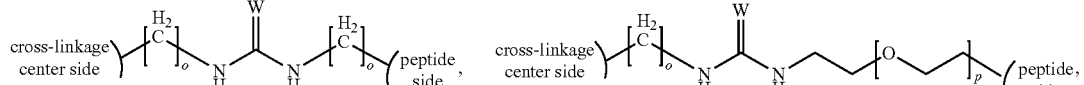

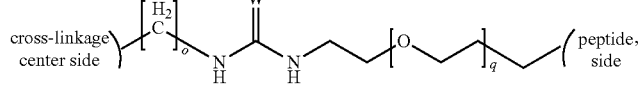

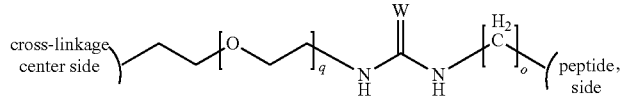

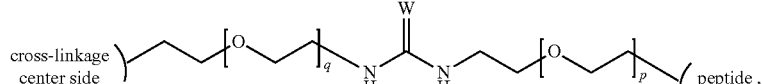

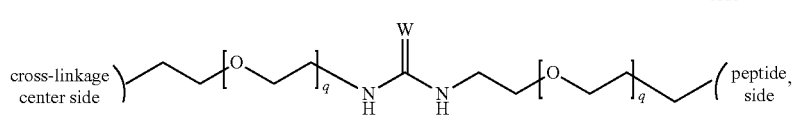

-continued

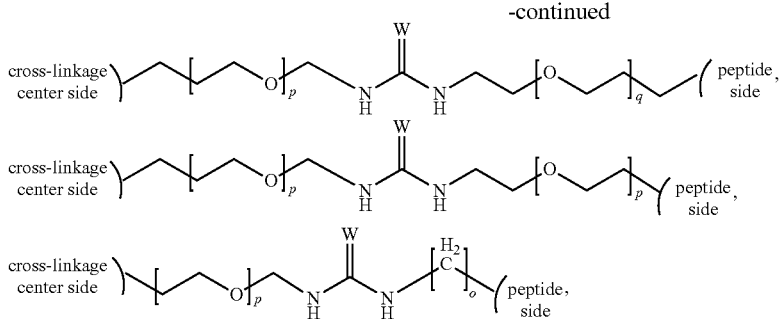

(Compound Y4)

[chemical formula 11]

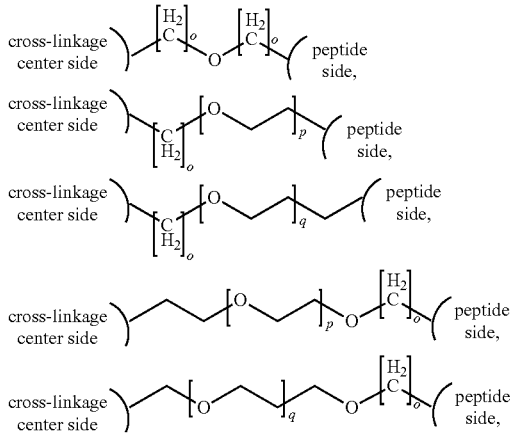

(Compound Y5)

[chemical formula 12]

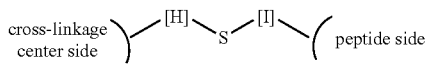

(here, [H] is represented by the following formula:

[chemical formula 13]

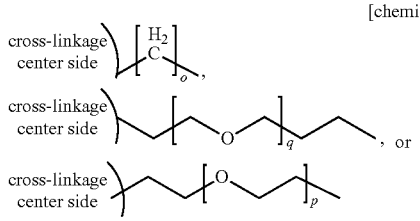

[I] is represented by the following formula:

[chemical formula 14]

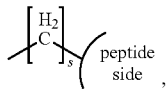

-continued

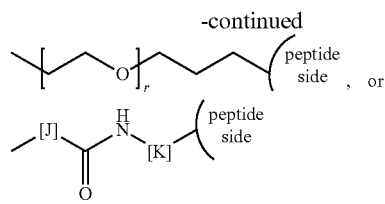

(here, [J] is represented by the following formula:

[chemical formula 15]

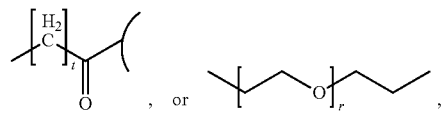

[K] is represented by the following formula:

[chemical formula 16]

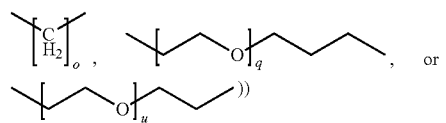

(wherein, o represents an integer of 1 to 12, p represents an integer of 1 to 27, q represents an integer of 1 to 24, r represents an integer of 1 to 8, s represents an integer of 1 to 16, t represents an integer of 1 to 15, u represents an integer of 1 to 11 and W represents O or S.);

8. The cross-linked peptide according to any one of [1] to [5], wherein X is any one selected from the group consisting of the following chemical formulae:

[chemical formula 17]

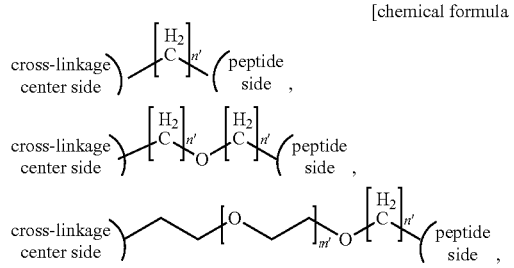

-continued

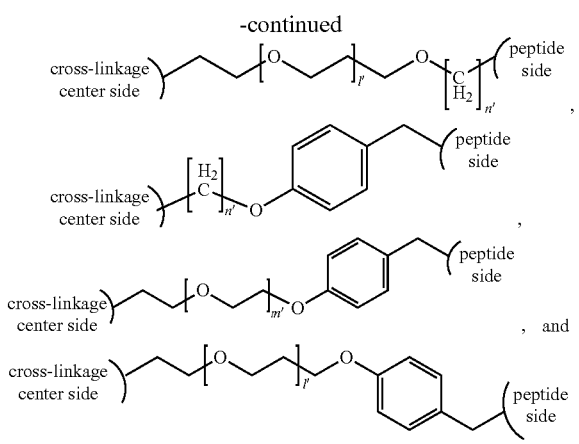

(wherein, n' represents an integer of 1 to 7, m' represents an integer of 1 to 11 and l' represents an integer of 1 to 12.) and Y is any one selected from the group consisting of the following chemical formulae:

[chemical formula 18]

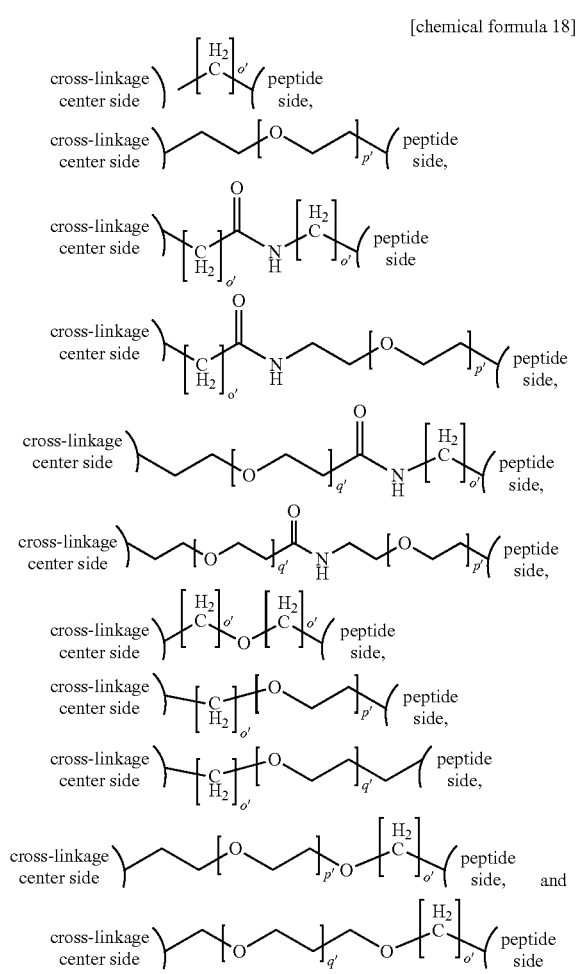

(wherein, o' represents an integer of 1 to 8, p' represents an integer of 1 to 11 and q' represents an integer of 1 to 12.);

9. The cross-linked peptide according to any one of [1] to [8], wherein Z is an acyl group having 1 to 8 carbon atoms, an unsubstituted or substituted alkyl group having 1 to 8 carbon atoms, polyethylene glycol having a molecular weight of 100 to 10000 Da represented by —C(=O)—CH$_2$CH$_2$(OCH$_2$CH$_2$)nOCH$_2$CH$_2$OCH$_3$ or any one selected from the group consisting of the following formulae:

[chemical formula 19]

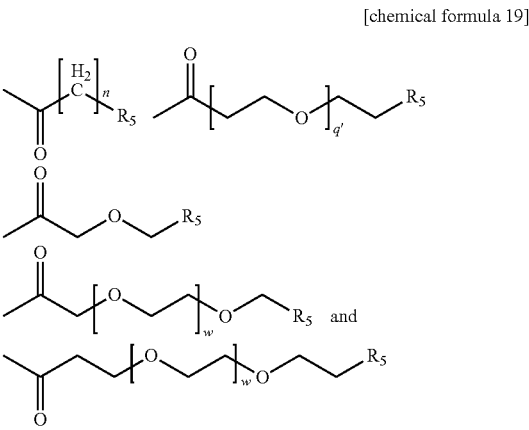

(wherein, n represents an integer of 1 to 12, q' represents an integer of 1 to 12, v represents 1 or 2 and w represents an integer of 1 to 12 (here, R$_5$ is represented by the following formula:

[chemical formula 20]

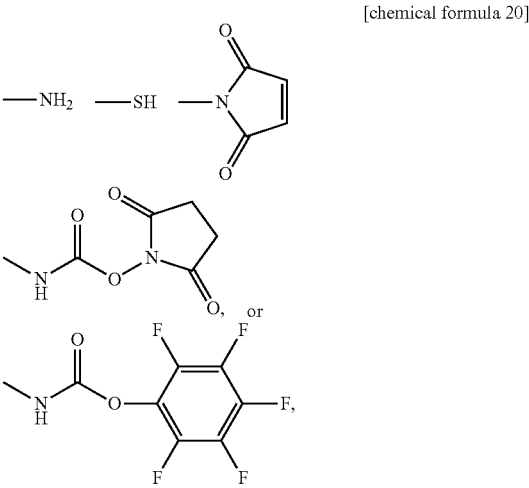

and R$_6$ is represented by the following formula:

[chemical formula 21]

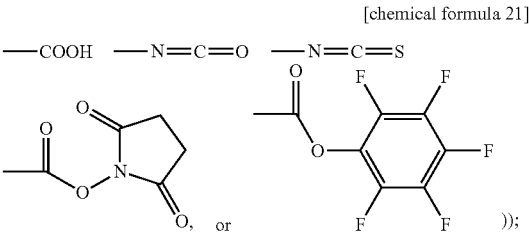

10. The cross-linked peptide according to any one of [1] to [9], wherein each of [E] and [G] represents at least one amino acid and/or unnatural amino acid and [F] represents at least two amino acids and/or unnatural amino acids;

11. A compound represented by the following chemical formula:

[chemical formula 22]

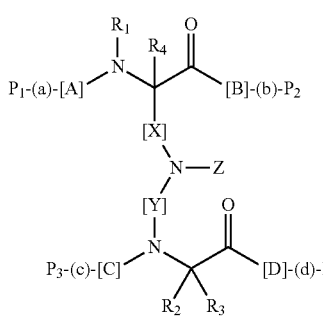

(wherein, X represents an alkylene chain having 1 to 12 carbon atoms or an alkylene chain having 1 to 66 carbon atoms containing at least one —O— or —S-bond, Y represents an alkylene chain having 1 to 12 carbon atoms or an alkylene chain having 1 to 66 carbon atoms containing at least one —O—, —NH— or —S-bond (optionally substituted by a divalent oxygen atom or sulfur atom), Z represents hydrogen, an optionally substituted alkyl group, having 1 to 30 carbon atoms, an optionally substituted acyl group having 1 to 36 carbon atoms, polyethylene glycol, a tBoc group, a Fmoc group, a Cbz group or a Nosyl group, [A], [B], [C] and [D] represent each independently a peptide having 1 to 20 residues composed of amino acids and/or unnatural amino acids as constituent elements or a single bond, (a) and (c) represent each independently —NH— or a single bond, (b) and (d) represent each independently —(C=O)— or a single bond (here, the sum of the numbers of amino acids of [A], [B], [C] and [D] is at least 1, and each of them may have a side chain protective group.), $R_1$, $R_3$ and $R_4$ represent each independently a hydrogen atom or a methyl group, $R_2$ represents a hydrogen atom or a side chain of an amino acid or unnatural amino acid, $P_1$ and $P_3$ represent each independently an amino protective group or a hydrogen atom, $P_2$ and $P_4$ represent each independently a —O-ester protective group, a —NH-benzyl protective group, an amino group or a hydroxyl group.);

12. A compound represented by the following chemical formula:

[chemical formula 23]

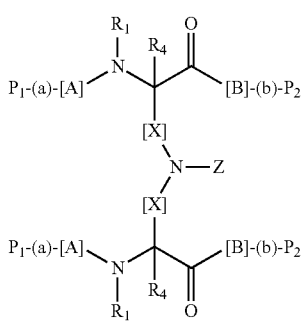

(wherein, X, Z, [A], [B], (a), (b), $R_1$, $R_4$, $P_1$ and $P_2$ are as described above. Here, Xs, [A]s, [B]s, (a)s, (b)s, $R_1$ s, $R_4$ s, $P_1$ s and $P_2$ s in the chemical formula may each be the same or different. The sum of the numbers of amino acids of [A] and [B] is at least 1, and each of them may have a side chain protective group.);

13. A compound represented by the following chemical formula:

[chemical formula 24]

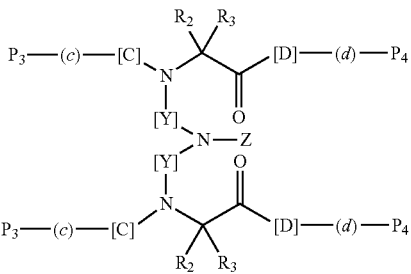

(wherein, Y, Z, [C], [D], (c), (d), $R_2$, $R_3$, $P_3$ and $P_4$ are as described above. Here, Ys, [C]s, [D]s, (c)s, (d)s, $R_2$ s, $R_3$ s, $P_3$ s and $P_4$ s in the chemical formula may each be the same or different. The sum of the numbers of amino acids of [C] and [D] is at least 1, and each of them may have a side chain protective group.);

14. The compound according to any one of [11] to [13], wherein one or more terminuses composed of $P_1$ or $P_3$ represent a hydrogen atom and one or more terminuses composed of $P_2$ or $P_4$ represent a hydroxyl group;

15. The compound according to any one of [11] to [13], wherein any one terminus composed of $P_2$ or $P_4$ represents a 2,4-alkoxy-substituted benzyl;

16. The compound according to [15], wherein the number of carbon atoms of the alkoxy-substituted group is 1 to 60;

17. The compound according to any one of [11] to [16], wherein X represents any one compound selected from the group consisting of the following formulae:

[chemical formula 25]

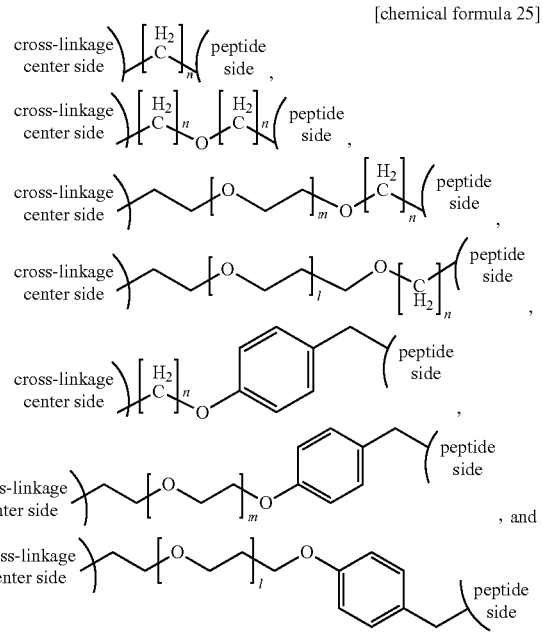

(wherein, n represents an integer of 1 to 12, m represents an integer of 1 to 24 and l represents an integer of 1 to 24.);

18. The compound according to [17], wherein Y is any one compound selected from the group consisting of the following compound Y1, compound Y2, compound Y3, compound Y4 and compound Y5:

(Compound Y1)

[chemical formula 26]

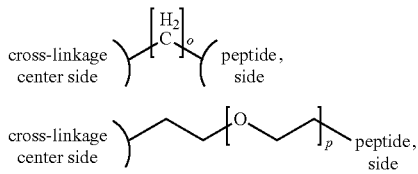

(Compound Y2)

[chemical formula 27]

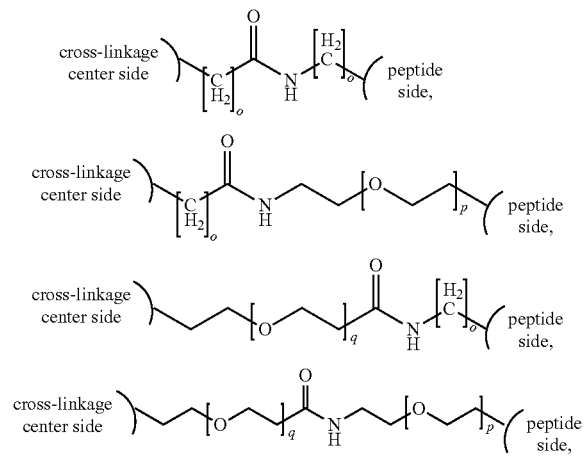

(Compound Y3)

[chemical formula 28]

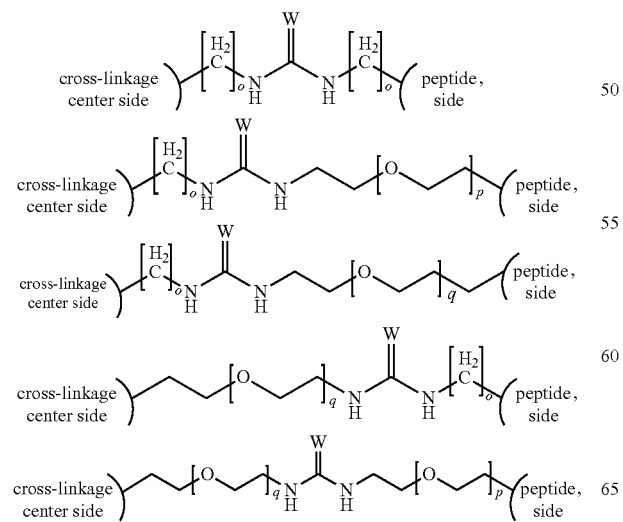

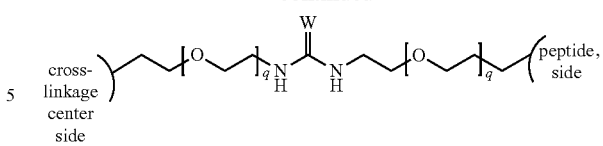
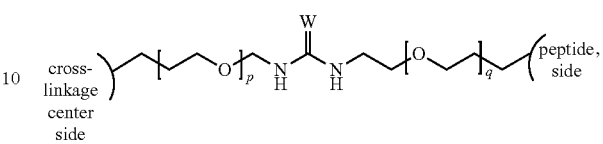
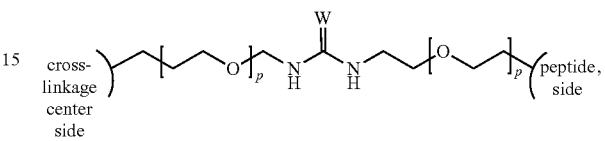
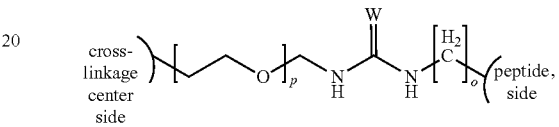

(Compound Y4)

[chemical formula 29]

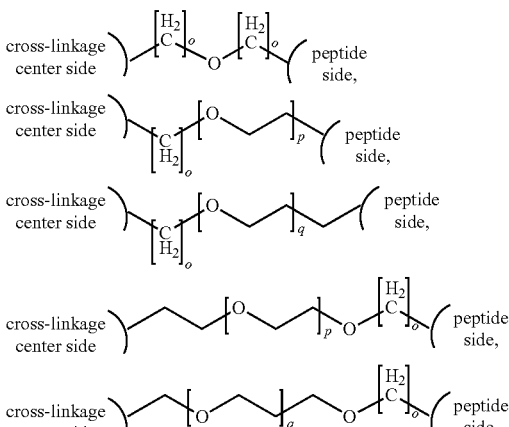

(Compound Y5)

[chemical formula 30]

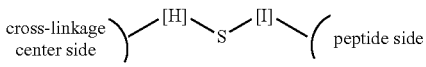

(wherein, [H] is represented by the following formula:

[chemical formula 31]

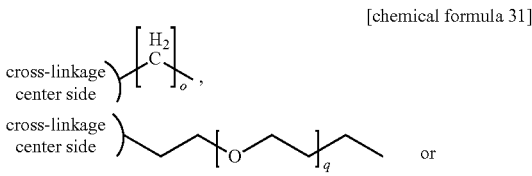

or

-continued

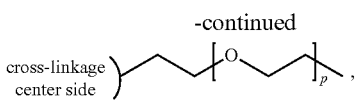

[I] is represented by the following formula:

[chemical formula 32]

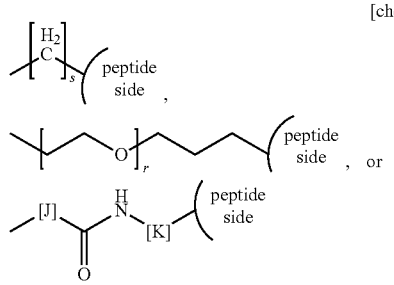

(here, [J] is represented by the following formula:

[chemical formula 33]

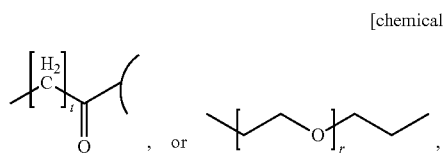

[K] is represented by the following formula:

[chemical formula 34]

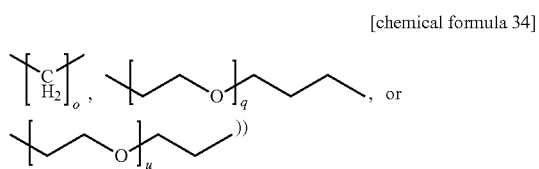

(wherein, o represents an integer of 1 to 12, p represents an integer of 1 to 27, q represents an integer of 1 to 24, r represents an integer of 1 to 8, s represents an integer of 1 to 16, t represents an integer of 1 to 15, u represents an integer of 1 to 11 and W represents O or S.);

19. The compound according to any one of [11] to [18], wherein each of [A], [B], [C] and [D] represents at least one amino acid and/or unnatural amino acid;

20. A method of synthesizing a cross-linked peptide represented by the following formula:

[chemical formula 35]

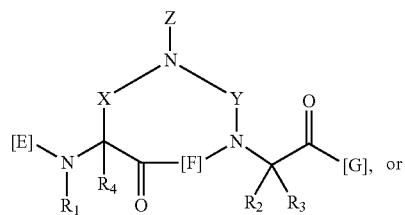

P-1

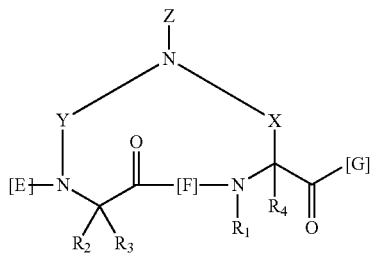

P-2

(wherein, X and Y represent each independently an alkylene chain having 1 to 12 carbon atoms or an alkylene chain having 1 to 66 carbon atoms containing at least one —O—, —NH— or —S-bond (optionally substituted by a divalent oxygen atom or sulfur atom), Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group, [E] represents hydrogen, an acetyl group or a peptide having 1 to 20 residues composed of amino acids and/or unnatural amino acids as constituent elements, [G] represents OH, an amino group or a peptide having 1 to 20 residues composed of amino acids and/or unnatural amino acids as constituent elements, [F] represents a peptide having 1 to 20 residues composed of amino acids and/or unnatural amino acids as constituent elements (here, the sum of the numbers of amino acids of [E], [F] and [G] is at least 3), $R_1$, $R_3$ and $R_4$ represent each independently a hydrogen atom or a methyl group, and $R_2$ represents a hydrogen atom or a side chain of an amino acid or unnatural amino acid.), comprising the following steps (a) to (g):

(a) a step of preparing a first component (A), comprising the following steps,
  (a-1) a step of, if necessary, condensing a carboxyl protective group with amino acids or a peptide constituting a partial peptide sequence of the cross-linked peptide, and further, if necessary, elongating the condensed group,
  (a-2) a step of reacting the N terminus side of the peptide or amino acid synthesized or the carboxyl protective group with an amino acid derivative containing in the side chain a linker forming part of a cross-linkage of the cross-linked peptide, to synthesize the peptide having the linker in the side chain or the amino acid derivative having the carboxyl group protected,
  (a-3) a step of, if necessary, further performing a peptide elongation reaction to elongate the peptide, and
  (a-4) a step of, if necessary (that is, when the linker end is not reactive), converting the functional group of the linker into a form with which the linker can be subjected to the subsequent cross-linkage forming reaction,
(b) a step of preparing a second component (B), comprising the following steps,
  (b-1) a step of condensing a carboxyl protective group with amino acids or a peptide constituting a partial peptide sequence of the cross-linked peptide, and if necessary, elongating the condensed group,
  (b-2) a step of reacting the N terminus of the peptide or the amino acid derivative synthesized with a compound containing a linker forming part of a cross-linkage of the cross-linked peptide, to synthesize a peptide or an amino acid derivative having a secondary amine at the N terminus containing the linker,
  (b-3) a step of, if necessary, further performing a peptide elongation reaction to elongate the peptide, and (b-4) a step of, if necessary (that is, when the linker end is not reactive), converting the functional group of the linker into a form with which the linker can be subjected to the subsequent cross-linkage forming reaction, (c) a step of linking (cross-linking) the first component (A) and the second component (B) by the Mitsunobu reaction, a reductive amination reaction or the Aza-Wittig reaction and the subsequent reduction reaction, to prepare an intermediate having a structure in which the two components are linked via a secondary amine or a tertiary amine, (d) a step of, if necessary, deprotecting a protective group at the N terminus of the first component (A) or the second component (B) and/or a protective group at the C terminus of the first component (A) or the second component (B), (e) a step of condensing the peptide N or C terminus of one component with the peptide C or N terminus of another component to form a peptide bond (peptide chain), (f) a step of, if necessary, post-processing the cross-linked peptide by any method known to those skilled in the art, and (g) a step of, if necessary, deprotecting the protective group;

21. A method of synthesizing the following cross-linked peptide:

[chemical formula 36]

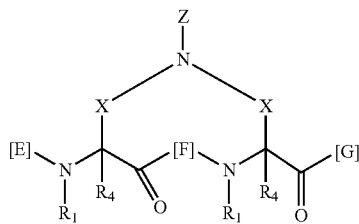

P-3

(X, Y, Z, [E] [F], [G], $R_1$, $R_2$, $R_3$ and $R_4$ are as described above.) comprising the following steps (a) to (g):

(a) a step of preparing a first component (A1) comprising the following steps, (a-1) a step of, if necessary, condensing a carboxyl protective group with amino acids or a peptide constituting a partial peptide sequence of the cross-linked peptide, and further, if necessary, elongating the condensed group, (a-2) a step of reacting the N terminus side of the peptide or amino acid synthesized or the carboxyl protective group with an amino acid derivative containing in the side chain a linker forming part of a cross-linkage of the cross-linked peptide, to synthesize the peptide having the linker in the side chain or the amino acid derivative having the carboxyl group protected, (a-3) a step of, if necessary, further performing a peptide elongation reaction to elongate the peptide, and (a-4) a step of, if necessary (that is, when the linker end is not reactive), converting the functional group of the linker into a form with which the linker can be subjected to the subsequent cross-linkage forming reaction, (b) a step of preparing a second component (A2), comprising the same steps as the above-described steps (a-1) to (a-4), (c) a step of linking (cross-linking) the first component (A1) and the second component (A2) by the Mitsunobu reaction, a reductive amination reaction or the Aza-Wittig reaction and the subsequent reduction reaction, to prepare an intermediate having a structure in which the first component (A1) and the second component (A1) are linked via a secondary amine or a tertiary amine, (d) a step of, if necessary, deprotecting a protective group at the N terminus of the first component (A1) or the second component (A2) and/or a protective group at the C terminus of the first component (A1) or the second component (A2), (e) a step of condensing the peptide N or C terminus of the first component (A1) with the peptide C or N terminus of the second component (A2) to form a peptide bond (peptide chain), (f) a step of, if necessary, post-processing the cross-linked peptide by any method known to those skilled in the art, and (g) a step of, if necessary, deprotecting the protective group;

22. A method of synthesizing the following cross-linked peptide:

[chemical formula 37]

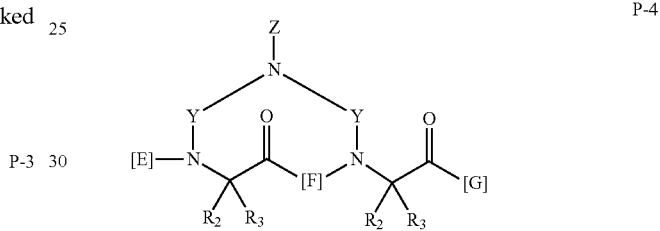

P-4

(X, Y, Z, [E], [F], [G], $R_1$, $R_2$, $R_3$ and $R_4$ are as described above.), comprising the following steps (a) to (g):

(a) a step of preparing a first component (B1), comprising the following steps, (a-1) a step of condensing a carboxyl protective group with amino acids or a peptide constituting a partial peptide sequence of the cross-linked peptide, and if necessary, elongating the condensed group, (a-2) a step of reacting the N terminus of the peptide or amino acid synthesized with a compound containing a linker forming part of a cross-linkage of the cross-linked peptide, to synthesize a peptide or an amino acid derivative having a secondary amine at the N terminus containing the linker, (a-3) a step of, if necessary, further performing a peptide elongation reaction to elongate the peptide, and (a-4) a step of, if necessary (that is, when the linker end is not reactive), converting the functional group of the linker into a form with which the linker can be subjected to the subsequent cross-linkage forming reaction, (b) a step of preparing a second component (B2), comprising the same steps as the above-described steps (a-1) to (a-4), (c) a step of linking (cross-linking) the first component (B1) and the second component (B2) by the Mitsunobu reaction, a reductive amination reaction or the Aza-Wittig reaction and the subsequent reduction reaction, to prepare an intermediate having a structure in which the first component (B1) and the second component (B2) are linked via a secondary amine or a tertiary amine, (d) a step of, if necessary, deprotecting a protective group at the N terminus of the first component (B1) or the second component (B2) and/or a protective group at the C terminus of the first component (B1) or the second component (B2), (e) a step of condensing the peptide N or C terminus of the first component (B1) with the peptide C or N terminus of the second component (B2) to form a peptide bond (peptide chain), (f) a step of, if necessary, post-processing the cross-linked peptide by any method known to those skilled in the art, and (g) a step of, if necessary, deprotecting the protective group;

23. A method of synthesizing the cross-linked peptide according to any one of [20] to [22], wherein the step (c) is carried out under condition in which at least one of the first component and the second component is linked to the carboxyl protective group as a peptide supporting body, wherein the peptide supporting body is an alkoxy-substituted benzyl selected from the group consisting of a 2,4-substituted benzyl alcohol, a 3,5-substituted benzyl alcohol, a 3,4,5-substituted benzyl alcohol and a 2,4,5-substituted benzyl alcohol;

24. The method of synthesizing the cross-linked peptide according to [23], wherein the number of carbon atoms of the alkoxy substituent of the 2,4-substituted benzyl alcohol used as the peptide supporting body is 1 to 60;

25. A cross-linked peptide represented by the following chemical formula:

[chemical formula 38]

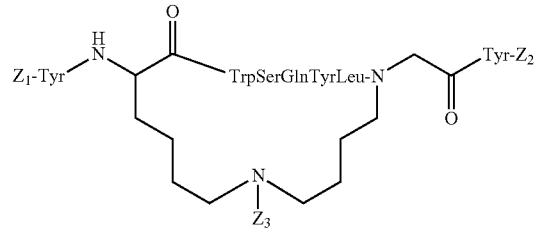

(wherein, $Z_1$ and $Z_3$ represent each independently an unsubstituted or substituted acyl group having 1 to 36 carbon atoms, an unsubstituted or substituted alkyl group having 1 to 30 carbon atoms or a polyethylene glycol having a molecular weight of 100 to 20000 Da represented by —C(=O)—CH$_2$CH$_2$(OCH$_2$CH$_2$)$_n$OCH$_2$CH$_2$OCH$_3$, and $Z_2$ represents a hydroxyl group, an amino group, an unsubstituted or substituted monoalkylamino group having 1 to 30 carbon atoms or a polyethylene glycol having a molecular weight of 100 to 20000 Da represented by —NH—CH$_2$CH$_2$ (OCH$_2$CH$_2$)$_n$ OCH$_2$CH$_2$OCH$_3$.); and 26. A cross-linked peptide represented by the following formula:

[chemical formula 39]

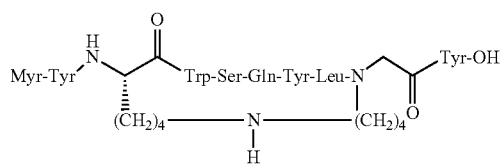

[chemical formula 40]

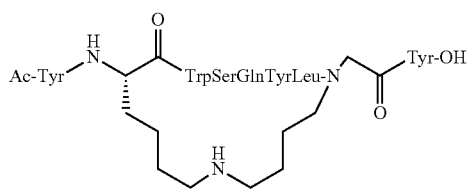

[chemical formula 41]

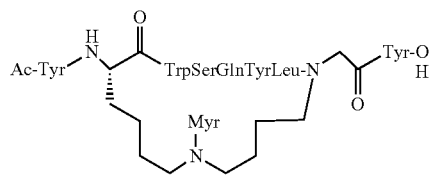

[chemical formula 42]

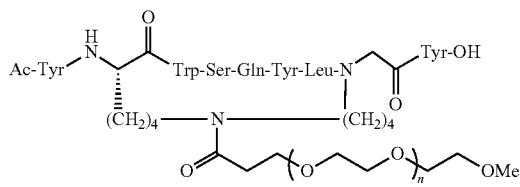

[chemical formula 43]

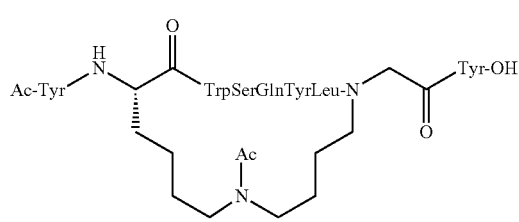

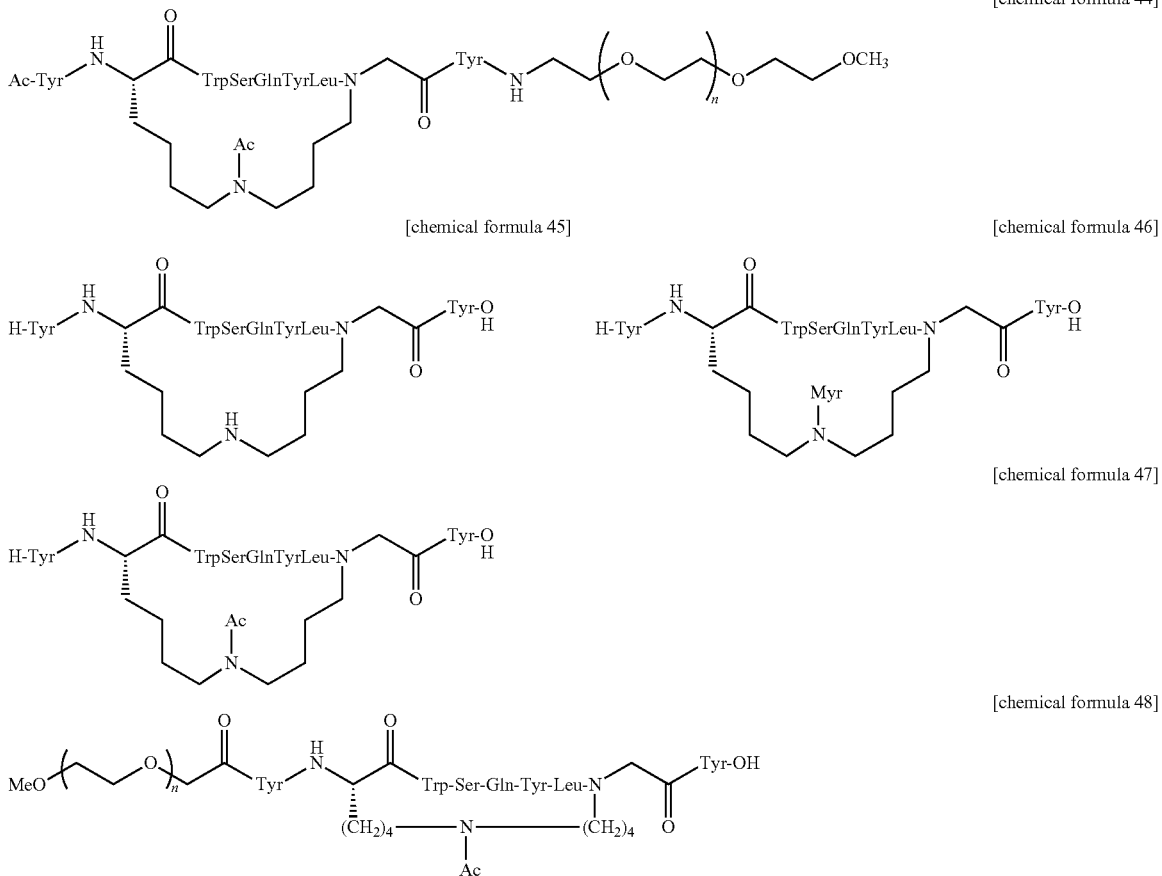

(wherein, Ac represents an acetyl group, and the polyethylene glycol has a number-average molecular weight of 500 to 2000 Da).

Advantageous Effects of Invention

In one object of the present invention, amino acids at any positions in a peptide chain can be cross-linked via a linker to synthesize a cross-linked peptide having a cross-linkage at any position.

In another object of the present invention, a novel cross-linked peptide can be provided in which the cross-linked portion of the cross-linked peptide has a new structure represented by —X—NZ—Y— (here, X, Y and Z are as defined above).

In still another object of the present invention, a peptide mimic can be provided, and the peptide mimic provided by the present invention can manifest different biological characteristics from those of peptides having a natural cross-linked structure, for example, resistance to a peptidase, and the like.

BRIEF EXPLANATION OF DRAWINGS

FIG. 8 shows a schematic view of a synthesis example of still other W9 cross-linked peptide mimics (Bdev-27 to 30) of the present invention.

DESCRIPTION OF EMBODIMENTS

Figure 1:
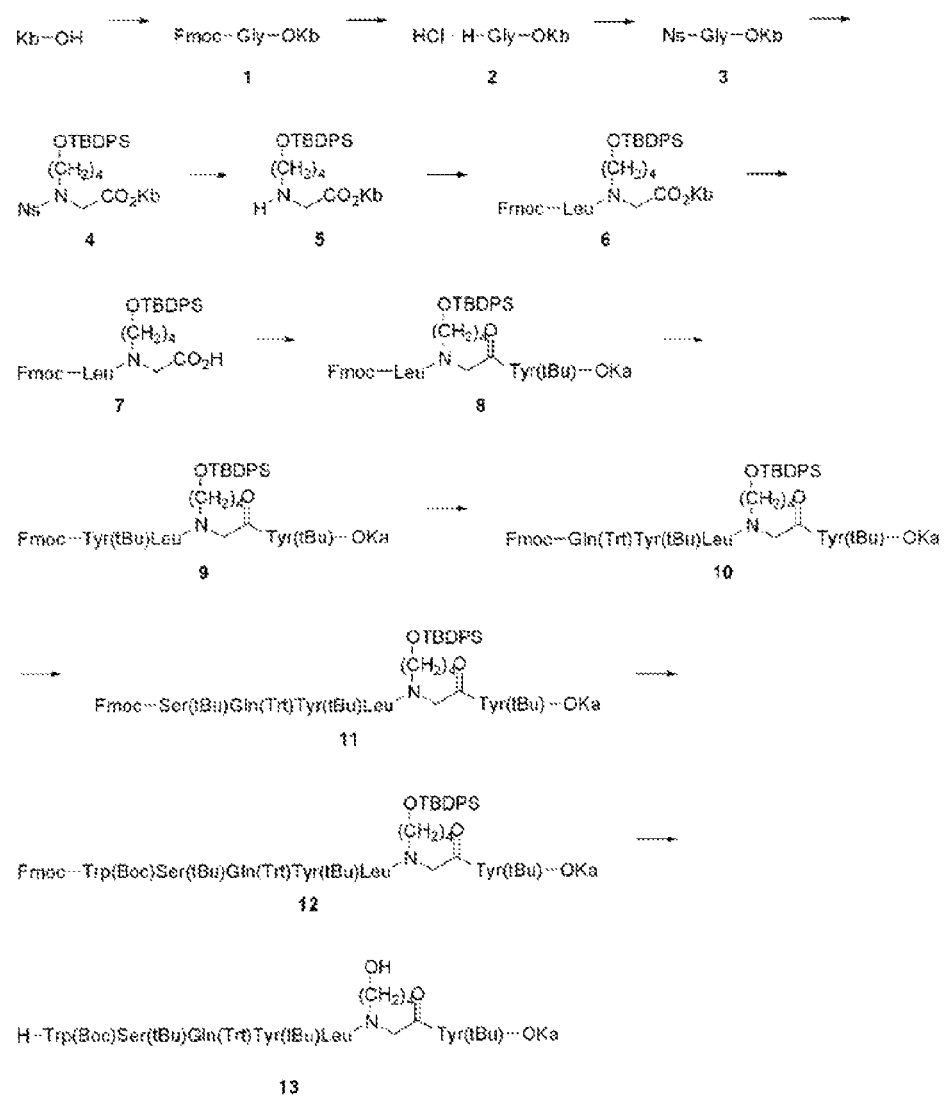
FIG. 1 shows a schematic view of a synthesis example of a component used in an intermediate of the present invention.

In the present specification, "cross-linked peptide" means a peptide chain in which side chains of amino acids in the main chain or terminus groups of the peptide chain constitute a circular form, and circularization is caused by side chain-side chain cyclization, side chain-terminus group cyclization or terminus group-terminus group cyclization, and as the cyclization, side chains and/or terminus groups may be directly linked or may be linked via a cross-linked structure having any length between them, and the cross-linked peptide of the present invention is characterized by having a —NR— bond in the cross-linked structure. R will be illustrated in detail in the present specification, together with other features of the present invention.

In the present specification, "amino acid" is used in a meaning including natural L-configured amino acids, and examples thereof include glycine, alanine, leucine, proline, phenylalanine, tyrosine, methionine, serine, threonine, cystine, cysteine, aspartic acid, glutamic acid, asparagine, glutamine, lysine, arginine, hydroxylysine, histidine, tryptophan, valine, β-alanine and the like, and α-amino acids in them are L-configured. In the present specification, "unnatural amino acid" includes, but not limited to, D-configured bodies and racemic bodies of the above-described natural amino acids, L-configured bodies, D-configured bodies and racemic bodies of hydroxyproline, norleucine, ornithine, naphthylalanine, nitrophenylalanine, chlorophenylalanine, fluorophenylalanine, thienylalanine, furylalanine, cyclohexylalanine, homoarginine, homoserine, 3-amino-2-benzyl-propionic acid, N-Me type amino acid and the like, and derivatives thereof. A lot of unnatural amino acids or amino acid derivatives are well known in the art, and included in "unnatural amino acid" referred to in the present specification.

In the present specification, when referred to "the number of amino acids", it means the number of amino acids of amino acids and/or unnatural amino acids, and in a peptide containing both amino acids and unnatural amino acids, it means the total number thereof.

1. Cross-Linked Peptide of the Present Invention

The cross-linked peptide (or peptide mimic) having a nonpeptidic cross-linked structure of the present invention has a structure described below.

[chemical formula 49]

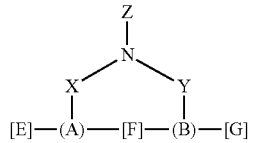

More specific embodiments of the cross-linked peptide (or peptide mimic) having a nonpeptidic cross-linked structure of the present invention has the following structures.

[chemical formula 50]

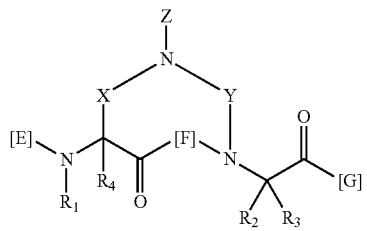

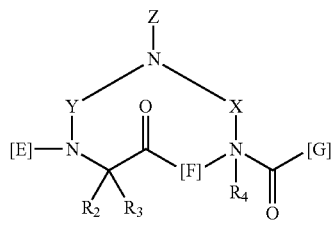

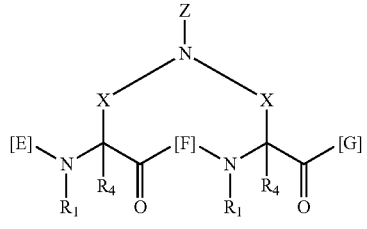

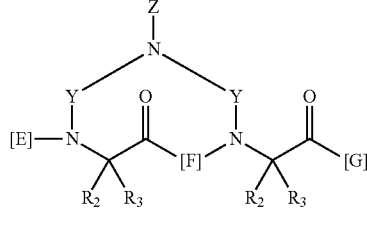

The definitions of marks in the above-described chemical formulae (P), (P-1), (P-2), (P-3) and (P-4) are as described below.

X represents an alkylene chain having 1 to 12, preferably 1 to 8, more preferably 1 to 4 carbon atoms or preferably a methylene chain thereof, or an alkylene chain having 1 to 66, preferably 1 to 30, more preferably 1 to 16 carbon atoms containing at least one —O— or —S-bond or preferably a methylene chain thereof. More preferably, X is selected from the following formulae.

[chemical formula 51]

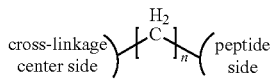
(X-1)

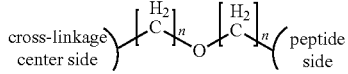
(X-2)

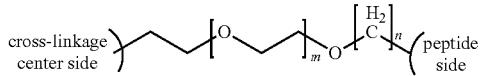
(X-3)

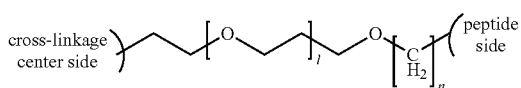
(X-4)

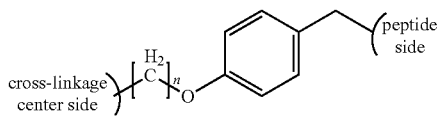
(X-5)

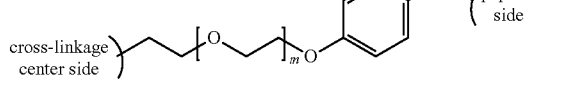
(X-6)

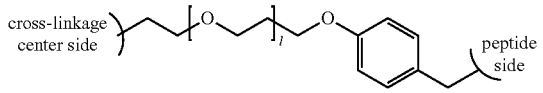
(X-7)

(wherein, n represents an integer of 1 to 12, preferably an integer of 1 to 7, further preferably an integer of 1 to 4. m represents an integer of 1 to 24, preferably an integer of 1 to 11, further preferably an integer of 1 to 7. l represents an integer of 1 to 24, preferably an integer of 1 to 12, further preferably an integer of 1 to 8). X is, more preferably, selected from the above-described chemical formulae (X-1), (X-2), (X-3) and (X-5), and most preferably, X is (X-1).

Y represents an alkylene chain having 1 to 12, preferably having 1 to 8, more preferably having 1 to 4 carbon atoms or preferably a methylene chain thereof, or an alkylene chain having 1 to 66, preferably having 1 to 30, more preferably having 1 to 16 carbon atoms containing at least one —O—, —NH— or —S-bond (optionally substituted by a divalent oxygen atom or sulfur atom) or preferably a methylene chain thereof. More preferably, Y is selected from the following formulae. (Compound Y1) Hereinafter, these are called Y1-1 and Y1-2 in descending order.

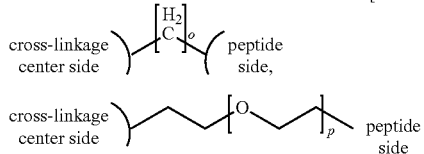
[chemical formula 52]

(Compound Y2) Hereinafter, these are called Y2-1 to Y2-4 in descending order.

[chemical formula 53]

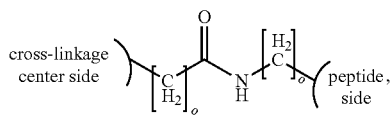

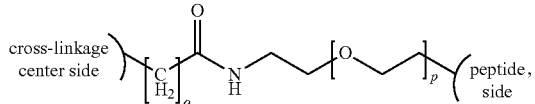

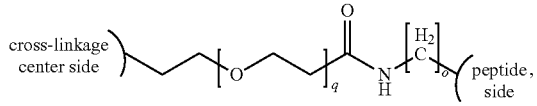

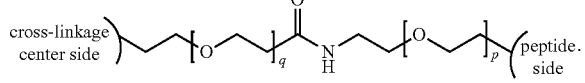

(Compound Y3) Hereinafter, these are called Y3-1 to Y3-9 in descending order.

[chemical formula 54]

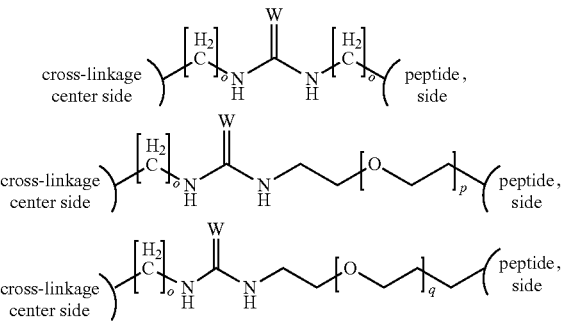

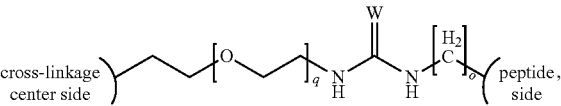

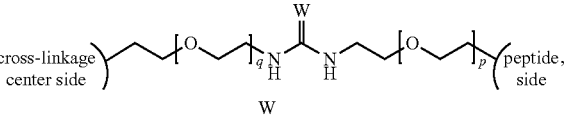

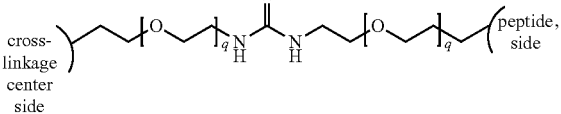

-continued

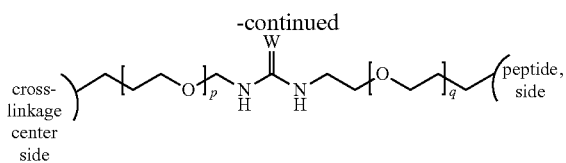

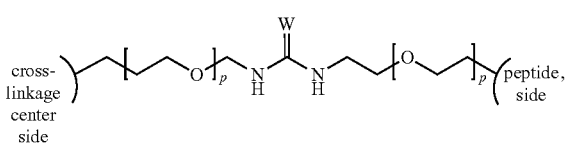

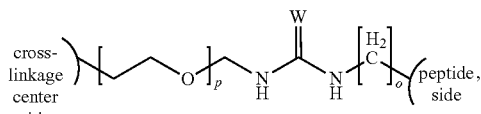

(Compound Y4) Hereinafter, these are called Y4-1 to Y4-5 in descending order.

[chemical formula 55]

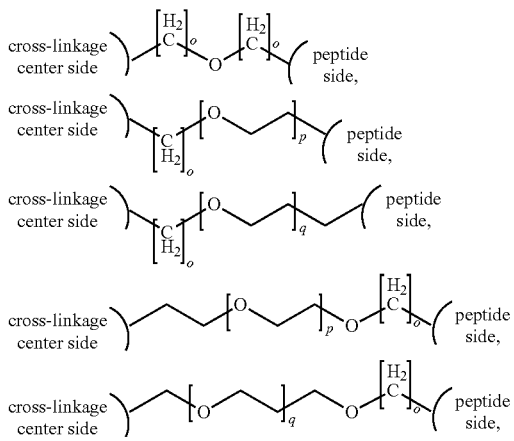

or
(Compound Y5)

[chemical formula 56]

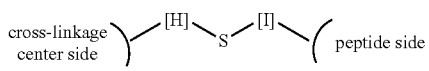

(wherein, [H] is represented by the following formula:

[chemical formula 57]

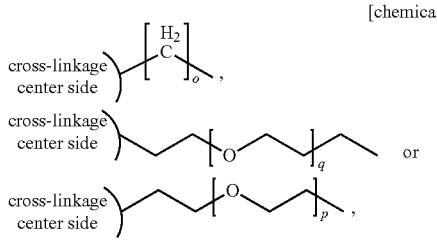

[I] is represented by the following formula:

[chemical formula 58]

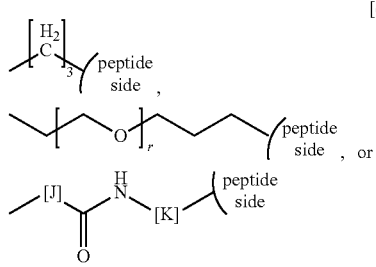

(here, [J] is represented by the following formula:

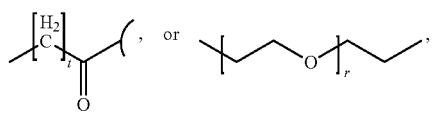

[K] is represented by the following formula:

[chemical formula 60]

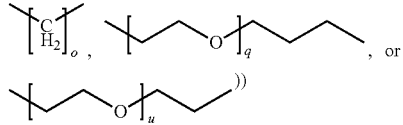

(wherein, o represents an integer of 1 to 12, preferably an integer of 1 to 8, more preferably an integer of 1 to 6. p represents an integer of 1 to 27, preferably an integer of 1 to 11, preferably an integer of 1 to 7. q represents an integer of 1 to 24, preferably an integer of 1 to 12, more preferably an integer of 1 to 8. r represents an integer of 1 to 8, preferably an integer of 1 to 4. s represents an integer of 1 to 16, preferably an integer of 1 to 11, more preferably an integer of 1 to 6. t represents an integer of 1 to 15, preferably an integer of 1 to 10, more preferably an integer of 1 to 4. u represents an integer of 1 to 11, preferably an integer of 1 to 7, more preferably an integer of 1 to 3. W represents O or S).

More preferably, Y is selected from (Y1-1), (Y1-2), (Y2-1), (Y2-2), (Y2-3), (Y4-1), (Y4-2) and (Y4-4), most preferably, Y is selected from (Y1-1) and (Y1-2).

Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group.

Here, the substituent is not particularly restricted providing that is can be linked by an organic reaction, and can be optionally selected depending on the object of the cross-linked peptide to be synthesized. Examples thereof include, but not limited to, a carboxyl group, an aldehyde group, an amino group, a thiol group, a maleimide group, a N-hydroxysuccinimide ester group, a pentafluorophenyl ester group, an isocyanate group, a thioisocyanate group, an acyl group, an alkyl group, an alkynyl group, an alkenyl group or an alkoxy group, or polyethylene glycol and the like.

Preferably, Z is an optionally substituted acyl group having 1 to 36 carbon atoms (for example, an acetyl group), an optionally substituted alkyl group having 1 to 30 carbon atoms, a polyethylene glycol having a molecular weight of 100 to 20000 Da, a tBoc group, a Fmoc group, a Cbz group or a Nosyl group, or any one selected from the group consisting of groups represented by the following formula.

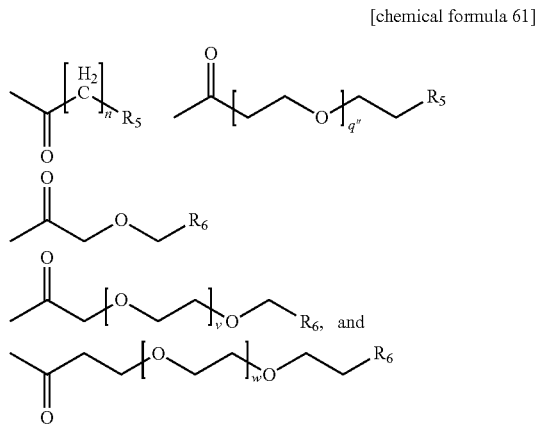

(wherein, n represents an integer of 1 to 12, preferably of 1 to 8, more preferably of 1 to 6, q' represents an integer of 1 to 12, preferably of 1 to 8, more preferably of 1 to 4, v represents 1 or 2, w represents an integer of 1 to 12, preferably of 1 to 8, more preferably of 1 to 4 (here, $R_5$ is represented by the following formula:

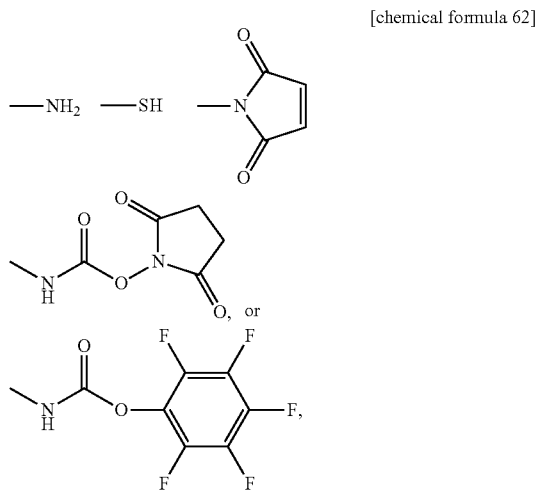

$R_6$ is represented by the following formula:

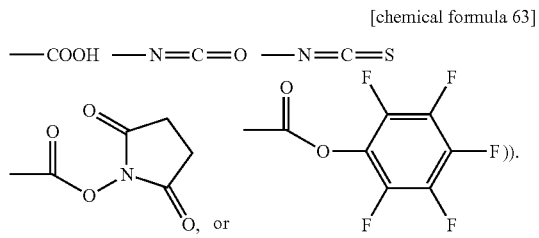

Further preferably, Z is hydrogen, an optionally substituted acyl group having 1 to 16 carbon atoms, a polyethylene glycol having a molecular weight of 1000 to 20000 Da, a tBoc group, a Fmoc group, a Cbz group or a Nosyl group.

In the cross-linked peptide of the present invention, it is possible to introduce a functional group or a substance capable of contributing to the stability and physiological activity of a peptide and the like into Z, thereby improving the physiological activity of a peptide and allowing a peptide to have a new function, and such a peptide is also included in the scope of the present invention.

The above-described (A) and (B) represent each independently any structure represented by the following formula:

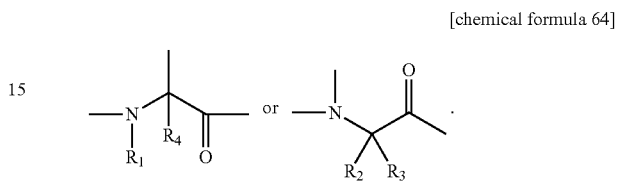

The above-described $R_1$, $R_3$ and $R_4$ represent each independently a hydrogen atom or a methyl group, and $R_2$ represents a hydrogen atom, or a side chain of an amino acid or unnatural amino acid. When $R_2$ is a side chain of an amino acid or unnatural amino acid, its kind is not particularly restricted, and in the case of, for example, serin, $R_2$ is $CH_2OH$.

The above-described [E] represents a peptide composed of any amino acids and/or unnatural amino acids, or a hydrogen atom or an optionally substituted acyl group having 1 to 6 carbon atoms, preferably represents at least one amino acid and/or unnatural amino acid, or a hydrogen atom or an acetyl group. The above-described [G] represents a peptide composed of any amino acids and/or unnatural amino acids, or a hydroxyl group or an amino group. The length of a peptide can be arbitrarily selected in the present invention, and for the purpose of synthesis of a peptide mimic of a peptide having physiological activity and from the standpoint of a peptide synthesis technology, the number of amino acids and/or unnatural amino acids of [E] or [G] is 1 to 20, preferably 1 to 10. However, the number of amino acids is not limited to this.

Further various modification groups can be attached to the terminus of [E] and/or [G], and also these embodiments are included in the scope of the cross-linked peptide of the present invention. Such a cross-linked peptide can be obtained by attaching a modification group to the terminus of [E] and/or [G] using a known method after synthesis of the above-described cross-linked peptide, or by using an amino acid constituting the terminus of [E] and/or [G] carrying a modification group in a synthesis process of a cross-linked peptide of the present invention.

In contrast, the above-described [F] is a peptide composed of any amino acids and/or unnatural amino acids, and its length can be arbitrarily selected depending on a physiologically active peptide to be mimicked, and the number of amino acids and/or unnatural amino acids is 1 to 20, preferably 2 to 20, more preferably 2 to 15, further preferably 3 to 10. However, the number of amino acids is not limited to this.

The sum of the numbers of amino acids or unnatural amino acids of [E], [F] and [G] is at least 3, preferably at least 4, further preferably at least 5.

When the number of amino acids of [F] is 10 or less, the above-described X is an alkylene chain having 1 to 8 carbon atoms, preferably a methylene chain, or a polyoxyalkylene chain having 1 to 16, preferably having 1 to 8 carbon atoms, preferably a polyoxyethylene glycol chain, and Y is an alkylene chain having 1 to 8 carbon atoms, preferably a methylene chain, or a polyoxyalkylene chain having 1 to 16, preferably having 1 to 8 carbon atoms, preferably a polyethylene glycol chain.

In the cross-linked peptide of the present invention, it is also possible to further bind any substances, for example, a low molecular weight or high molecular weight compound, a peptide, a supporting body or other substances to the N terminus of a peptide [E] or the C terminus of a peptide [G] or both the terminuses, and also cross-linked peptides carrying these substances bound are included in the scope of the present invention. Examples thereof include, but not limited to, a low molecular weight compound or peptide showing a binding ability specific to a particular tissue, cell or protein, a fluorescent pigment, a compound containing a radioactive isotope, an intracellular migrating peptide, a low molecular weight compound or peptide having cytocidal activity such as doxorubicin and the like, polyethylene glycol, an acyl group having 1 to 18 carbon atoms, an alkyl group having 1 to 18 carbon atoms, a solid phase plate and the like.

The above-described N terminus of [E] may be protected by an amino protective group. Examples of the amino protective group include, but not limited to, Fmoc, Boc, CbZ, Trityl, or an acetyl group.

The above-described C terminus of [G] may be protected by an O-ester protective group or —NH-benzyl protective group. The O-ester protective group includes, but not limited to, a —O— benzyl group, a —O-t-butyl group, and additionally, —O-alkoxy-substituted benzyl groups described below.

2. Synthesis Intermediate Compound

As the intermediate for synthesizing a cross-linked peptide of the present invention, the following compounds are useful.

[chemical formula 65]

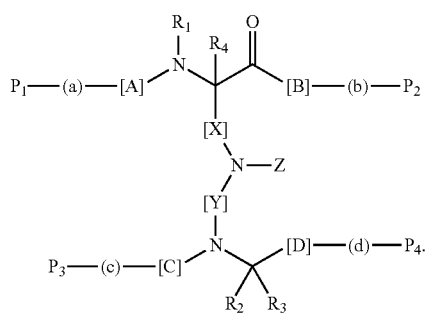

(M-1)

Further, as the intermediate for synthesizing a cross-linked peptide of the present invention, the following compounds are useful.

[chemical formula 66]

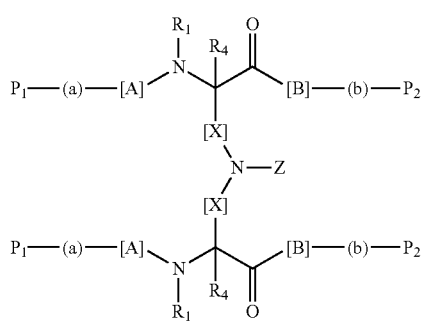

(M-4)

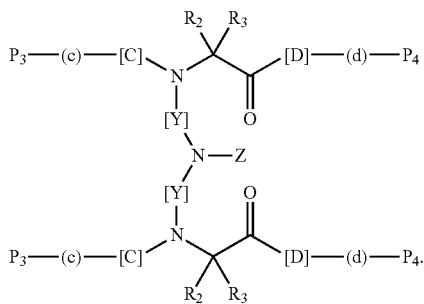

(M-5)

X, Y, $R_1$, $R_2$, $R_3$ and $R_4$ are as described above.

[A], [B], [C] and [D] are as described above. When [A], [B], [C] or [D] is a peptide, the sum of the numbers of amino acids is at least 3, preferably at least 4, and the number of amino acids of each moiety can be optionally selected depending on the intended cross-linked peptide. Specifically, the kind of an amino acid and/or unnatural amino acid and the number of amino acids can be optionally selected depending on which of [A], [B], [C] and [D] of the above-described compound corresponds to a peptide in the ring after circularization or a peptide at the N terminus or C terminus outside of the ring after circularization.

The above-described (a) and (c) represent each independently —NH— or a single bond, and (b) and (d) represent each independently —(C=O)— or a single bond. When two or more (a)s, (b)s, (c)s or (d)s are contained in the above-described formulae, each of them may be the same or different.

$P_1$ and $P_3$ represent each independently an amino protective group or a hydrogen atom, and $P_2$ and $P_4$ represent each independently an —O-ester protective group, an —NH-benzyl protective group, an amino group or a hydroxyl group. In the above-described formula, $P_1$, $P_2$, $P_3$ or $P_4$ may be the same or different, and when two or more $P_1$ s, $P_2$ s, $P_3$ s or $P_4$ s are contained in the same formula, each of them may be the same or different, and different is preferable.

Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group.

Here, the substituent is not particularly restricted providing that it can be linked by an organic reaction, and can be optionally selected depending on the object of the cross-linked peptide to be synthesized. Examples thereof include, but not limited to, a protected carboxyl group, a protected amino group, a protected thiol group, an acyl group, an alkyl group, an alkynyl group, an alkenyl group or an alkoxy group, or polyethylene glycol and the like.

Examples of the above-described amino protective group represented by $P_1$ or $P_3$ include, but not limited to, Fmoc, Boc, CbZ, Trityl, an acetyl group, and additionally, compounds working as a peptide supporting body in liquid phase synthesis of a peptide.

When the above-described $P_1$ and $P_3$ are both an amino protective group, a combination of protective groups capable of performing de-protection under different conditions is preferable. When, for example, one component is a Boc group, it is preferable that the other protective group is a CbZ group or a Fmoc group.

The above-described —O-ester protective group represented by $P_2$ or $P_4$ includes, but not limited to, an —O-benzyl group, an —O-t-butyl group, an —O-alkoxy-substituted benzyl group, an —O-substituted methyl group, a —O-diphenylmethane derivative, and additionally, compounds working as a peptide supporting body in liquid phase synthesis of a peptide.

When the above-described $P_2$ and $P_4$ are both an —O-ester protective group, a combination of protective groups capable of performing de-protection under different conditions is preferable. When, for example, one component is an —O-t-butyl group, it is preferable that the other protective group is an —O-tetrahydropyranyl group.

Examples of the compound working as a peptide supporting body in liquid phase synthesis of a peptide (in the present specification, referred sometimes to as "Hiver") include compounds described in JP-A No. 2004-59509, compounds described in PCT international publication WO2007/034812, compounds described in PCT international publication WO2007/122847, compounds described in PCT international publication WO2010/104169 and compounds described in PCT international publication WO2010/113939. The contents described in these publications constitute part of the present specification by incorporating herein by reference.

The preferable alkoxy-substituted benzyl group includes, compounds having a structure described below (referred to as "Ka" in some cases in the present specification):

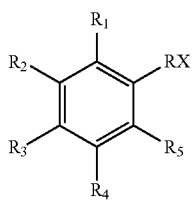

[chemical formula 67]

(wherein, $R_1$ and $R_5$ represent a hydrogen atom, and $R_2$, $R_3$ and $R_4$ represent an alkoxyl group having 18 to 30, preferably 18 to 22 carbon atoms. In the formula, RX has a reagent active site represented by the following formula.

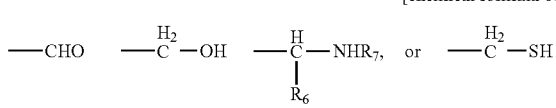

[chemical formula 68]

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group.))

compounds having a structure described below (referred to as "Kb" in some cases in the present specification):

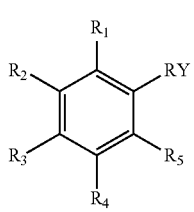

[chemical formula 69]

(wherein, $R_2$, $R_4$ and $R_5$ represent a hydrogen atom, and $R_1$ and $R_3$ represent an alkoxyl group having 18 to 30, preferably 18 to 22 carbon atoms. In the formula, RY has a reagent active site represented by the following formula.

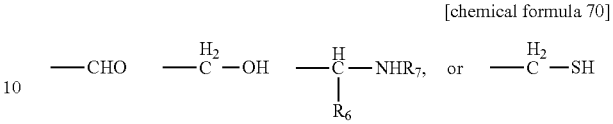

[chemical formula 70]

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group.)), and compounds having a structure described below (referred to as "Kc" in some cases in the present specification):

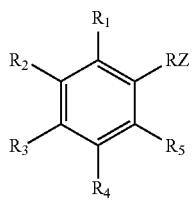

[chemical formula 71]

(wherein, $R_1$, $R_3$ and $R_5$ represent a hydrogen atom, and $R_2$ and $R_4$ represent an alkoxyl group having 18 to 30, preferably 18 to 22 carbon atoms. In the formula, RZ has a reagent active site represented by the following formula.

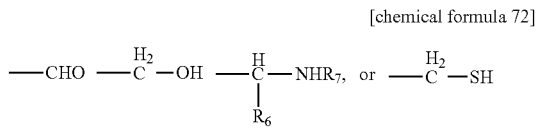

[chemical formula 72]

(wherein, $R_7$ represents a hydrogen atom, an alkyl group having 1 to 6 carbon atoms, a benzyl group or an alkoxy-substituted benzyl group, and $R_6$ represents a hydrogen atom, a phenyl group or an alkoxy-substituted phenyl group.)).

By using the above-described alkoxy-substituted benzyl groups Ka to Kc in combination with other amino protective groups and —O-ester protective groups, the whole reaction for synthesizing a cross-linked peptide of the present invention including peptide synthesis can be carried out in a liquid phase. Ka is preferably used with designing de-protection with 50 to 100% trifluoroacetic acid, Kb is preferably used with designing de-protection with 1 to 100% trifluoroacetic acid, and Kc is preferably used with designing de-protection with 95 to 100% trifluoroacetic acid.

It is particularly preferable to use Ka and Kb in combination or Kc and Kb in combination, owing to a difference in the property thereof, for example, because only Kb can be selectively deprotected under condition of 1 to 5% trifluoroacetic acid.

In another preferable embodiment, it is preferable to use Kb as $P_2$ or $P_4$ of one component and to use an —O-ester protective group de-protectable under ultra-weakly acidic conditions, basic conditions and reductive conditions as $P_2$ or $P_4$ of the other component. The protective group cleavable under ultra-weakly acidic conditions includes an —O-tetrahydropyranyl group, the protective group cleavable under basic conditions includes an —O-fluorenylmethyl group, and the protective group cleavable under reductive conditions includes an —O-benzyl group.

The cross-linked peptides (P-1) and (P-2) of the present invention can be synthesized, for example, by reactions shown below using the above-described intermediate compounds.

sequence and an exocyclic amino acid sequence of the cross-linked peptide can be easily operated at will in the present invention. When any one or two or more of [A], [B], [C] and [D] are a single bond, also a cyclic peptide carrying no exocyclic peptide present or a cyclic peptide in which a peptide extends to only one direction from the ring can be fabricated, and these are also included in the scope of the present invention.

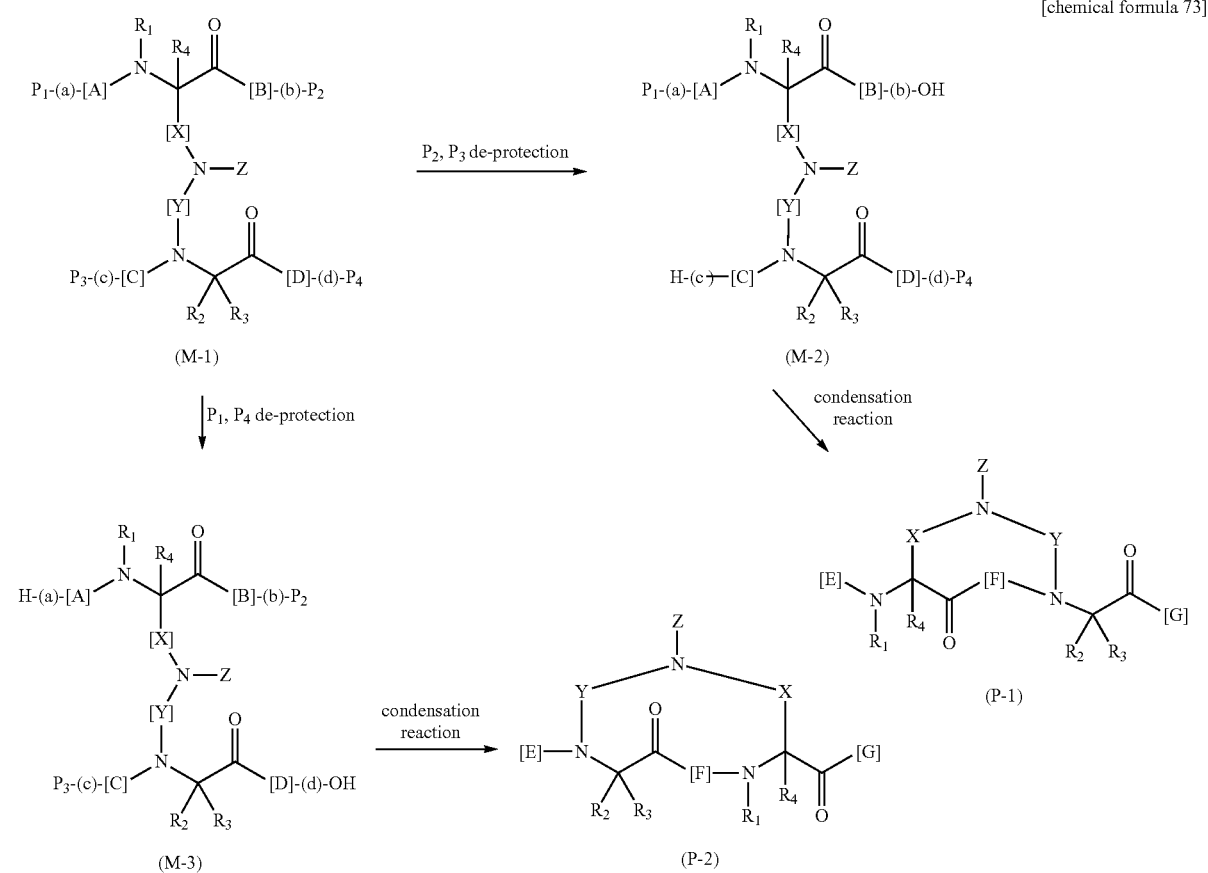

(wherein, the definitions of marks are the same as those described for the above-described intermediates and the above-described cross-linked peptides.).

That is, the final cross-linked peptide (P-1) can be fabricated via an intermediate (M-1) and an intermediate (M-2) in this order. In this case, an endocyclic peptide sequence [F] is fabricated from peptide sequences [B] and [C] of the intermediate, and a peptide sequence [A] constitutes the N terminus and a peptide sequence [D] constitutes the C terminus.

In contrast, the final cross-linked peptide (P-2) can be fabricated via an intermediate (M-1) and an intermediate (M-3) in this order. In this case, an endocyclic peptide sequence [F] is fabricated from peptide sequences [A] and [D] of the intermediate, and an amino acid of a peptide [C] constitutes the N terminus and a peptide [B] constitutes the C terminus.

Therefore, a cross-linked peptide having a cross-linked structure at any site in a peptide sequence can be synthesized easily. Further, since the sequence of a peptide [A], [B], [C] or [D] can be optionally selected, an endocyclic amino acid In the intermediate (M-1), all terminuses are protected, and the intermediate (M-2) or the intermediate (M-3) can be fabricated by deprotecting any N terminus and any C terminus of the intermediate (M-1), and depending on the intermediate synthesis method, the intermediate (M-2) or the intermediate (M-3) can be synthesized directly not via the intermediate (M-1).

The de-protection reaction can be carried out by a method well known to those skilled in the art. Examples thereof include, but not limited to, de-protection with an acid such as trifluoroacetic acid, 4N—HCl/dioxane and the like, de-protection by a catalytic hydrogenation reaction using palladium as a catalyst, de-protection with a base such as DBU and the like.

A cross-linked peptide (P-1) or (P-2) of the present invention can be synthesized by performing a condensation reaction in the intermediate (M-2) or (M-3). The condensation reaction can be carried out by a method known to those skilled in the art, and examples thereof include, but not limited to, a method using a carbodiimide condensation agent such as diisopropylcarbodiimide and the like, a method using an uronium condensation agent such as HBTU and the like; etc.

Synthesis of a cross-linked peptide from an intermediate of another embodiment of the present invention will be described below.

A cross-linked peptide (P-3) of the present invention can be synthesized by the same method as used for (M-1), as described below, using the above-described another intermediate compound.

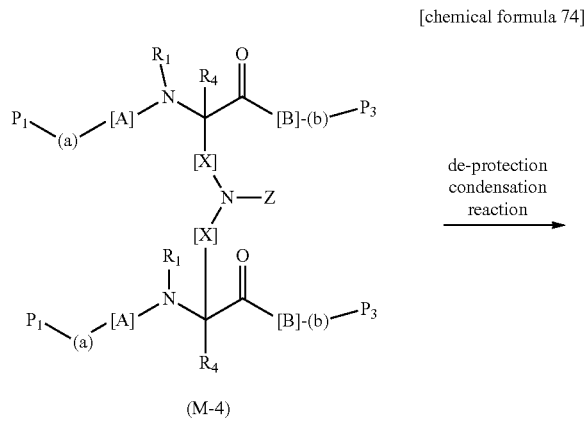

(wherein, the definitions of marks are as described above.).

A cross-linked peptide (P-4) of the present invention can be synthesized by the same method as used for (M-1), as described below, using the above-described another intermediate compound.

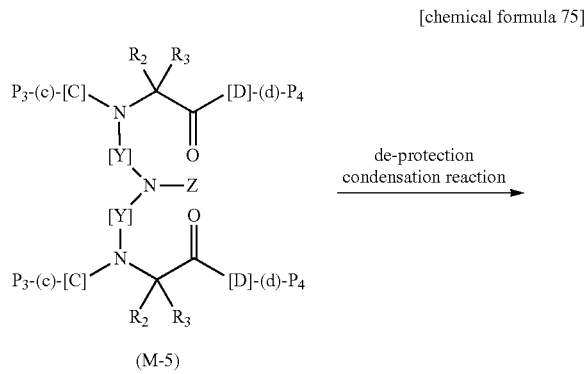

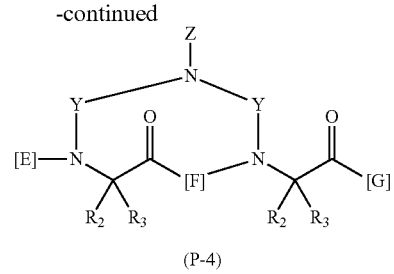

(wherein, the definitions of marks are as described above.).

3. Synthesis of Intermediate

The intermediate compound (M-1) of the present invention can be synthesized by synthesizing a compound containing X forming part of a cross-linkage (here, referred to as "X side component") and a compound containing Y forming part of a cross-linkage (here, referred to as "Y side component"), separately, then, linking both the compounds.

(3-1. Synthesis of X Side Component)

An X side component can be synthesized via the following steps.

(a) a step of preparing a first component, comprising the following steps, (a-1) a step of, if necessary, condensing a carboxyl protective group with amino acids or a peptide constituting a partial peptide sequence of the cross-linked peptide, and further, if necessary, elongating the condensed group, (a-2) a step of reacting the N terminus side of the peptide or amino acid synthesized or the carboxyl protective group with an amino acid derivative containing in the side chain a linker forming part of cross-linkage of the cross-linked peptide, to synthesize the peptide having the linker in the side chain or the amino acid derivative having the carboxyl group protected, and (a-3) a step of, if necessary, further performing a peptide elongation reaction to elongate the peptide.

The peptide elongation reaction can be carried out based on a known peptide synthesis method, and may be carried out by a solid phase method or a liquid phase method, and from the standpoint of enhanced efficiency of the reaction, and the like, a liquid phase synthesis method is preferable. In the case of synthesis in a liquid phase, it is preferable to protect the C terminus of a peptide with an alkoxy-substituted benzyl group.

Linking a compound containing a linker to the N terminus of a peptide can be carried out by a condensation reaction known to those skilled in the art, for example, by using the Mitsunobu reaction, however, the method is not limited to this.

Examples of synthesis of an X side component include, but not limited to, reactions exemplified below, and those skilled in the art can make various changes using known technologies.

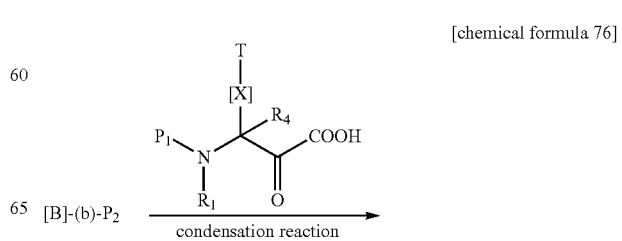

-continued

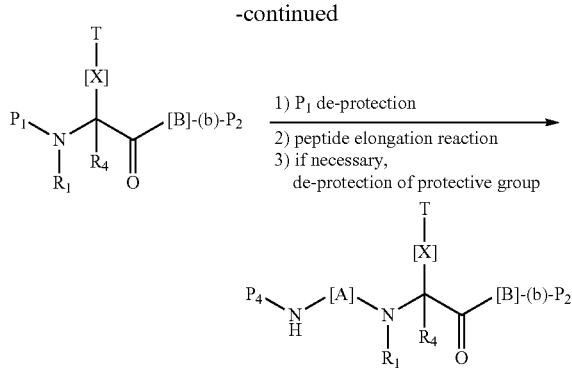

(here, the definitions of marks are as described above, and T represents —OH, —OP$_5$, —NH$_2$, —NHP$_6$ or —NHNs. P$_5$ and P$_6$ represent a hydroxyl protective group and an amino protective group, respectively, known to those skilled in the art.).

Examples of the compound providing X in synthesis of an X side component preferably include, but not limited to, the following compounds.

[chemical formula 77]

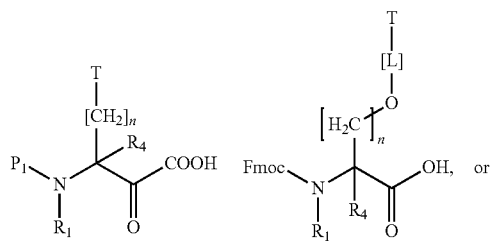

-continued

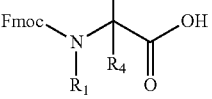

(wherein, n represents an integer of 1 to 10, preferably an integer of 1 to 7, more preferably an integer of 1 to 4, and the definitions of R$_1$ and R$_4$ are as described above. T represents —OH, —OP$_2$, —NH$_2$, —NHP$_3$ or —NHNs.).

Here, [L] is selected from the following compounds.

[chemical formula 78]

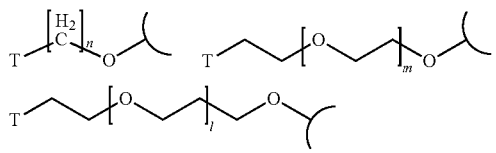

(wherein, n represents an integer of 1 to 10, preferably an integer of 1 to 7, more preferably an integer of 1 to 4, m represents an integer of 1 to 27, preferably an integer of 1 to 11, more preferably an integer of 1 to 7, and l represents an integer of 1 to 24, preferably an integer of 1 to 12, more preferably an integer of 1 to 8.)).

One of examples of synthesizing compounds providing various Xs, used in synthesis of an X side component, will be illustrated below.

[chemical formula 79]

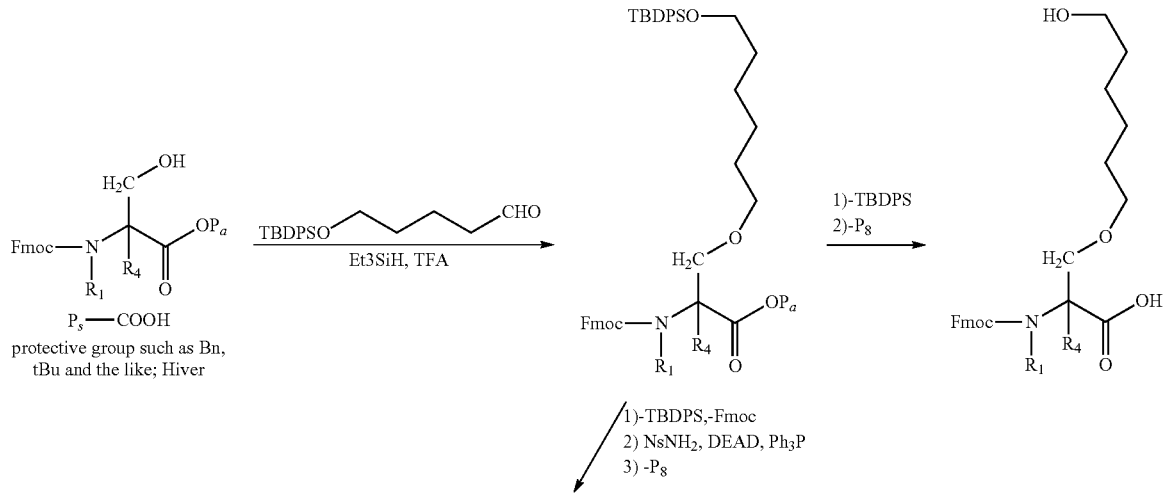

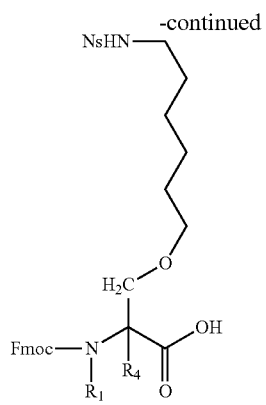

(3-2. Synthesis of Y Side Component)

A Y side component can be synthesized via the following steps.

- (b-1) a step of condensing a carboxyl protective group with amino acids or a peptide constituting a partial peptide sequence of the cross-linked peptide, and if necessary, elongating the condensed group,
- (b-2) a step of reacting the N terminus of the peptide (in this case, it is preferable that the N terminus is, for example, modified with Ns or modified with bromoacetyl) or the amino acid derivative synthesized with a compound containing a linker forming part of a cross-linkage of the cross-linked peptide, to synthesize a peptide or an amino acid derivative having a secondary amine at the N terminus containing the linker, and
- (b-3) a step of, if necessary, further performing a peptide elongation reaction to elongate the peptide.

Examples of synthesis of a Y side component include, but not limited to, reactions exemplified below, and those skilled in the art can make various changes using known technologies.

[chemical formula 80]

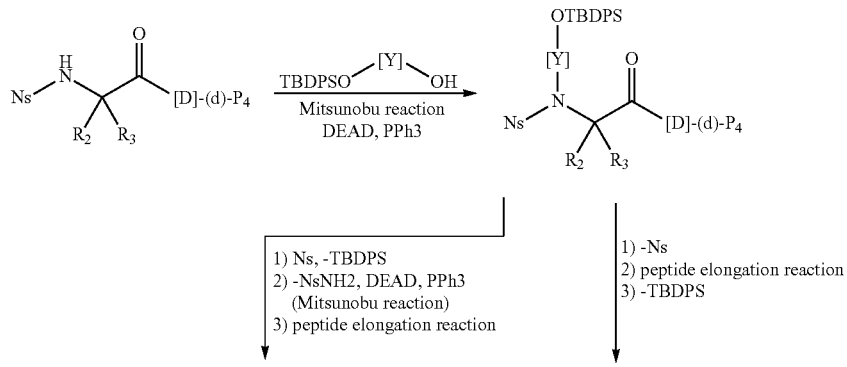

(The definitions are as described above.).
Another embodiment:

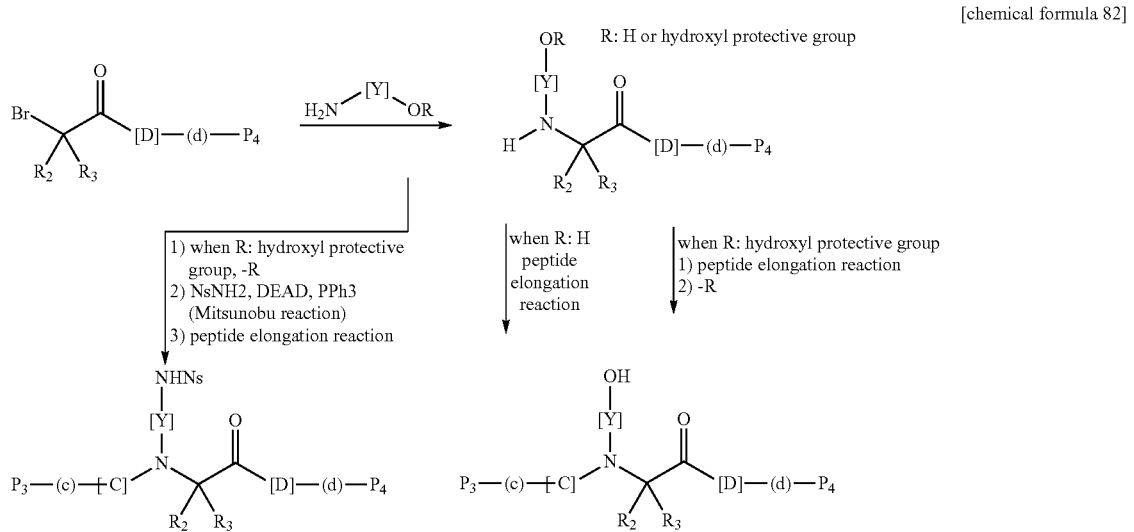

[chemical formula 82]

(The definitions are as described above.).

(3-2-1) One embodiment in which Y is the above-described compound Y1-1:

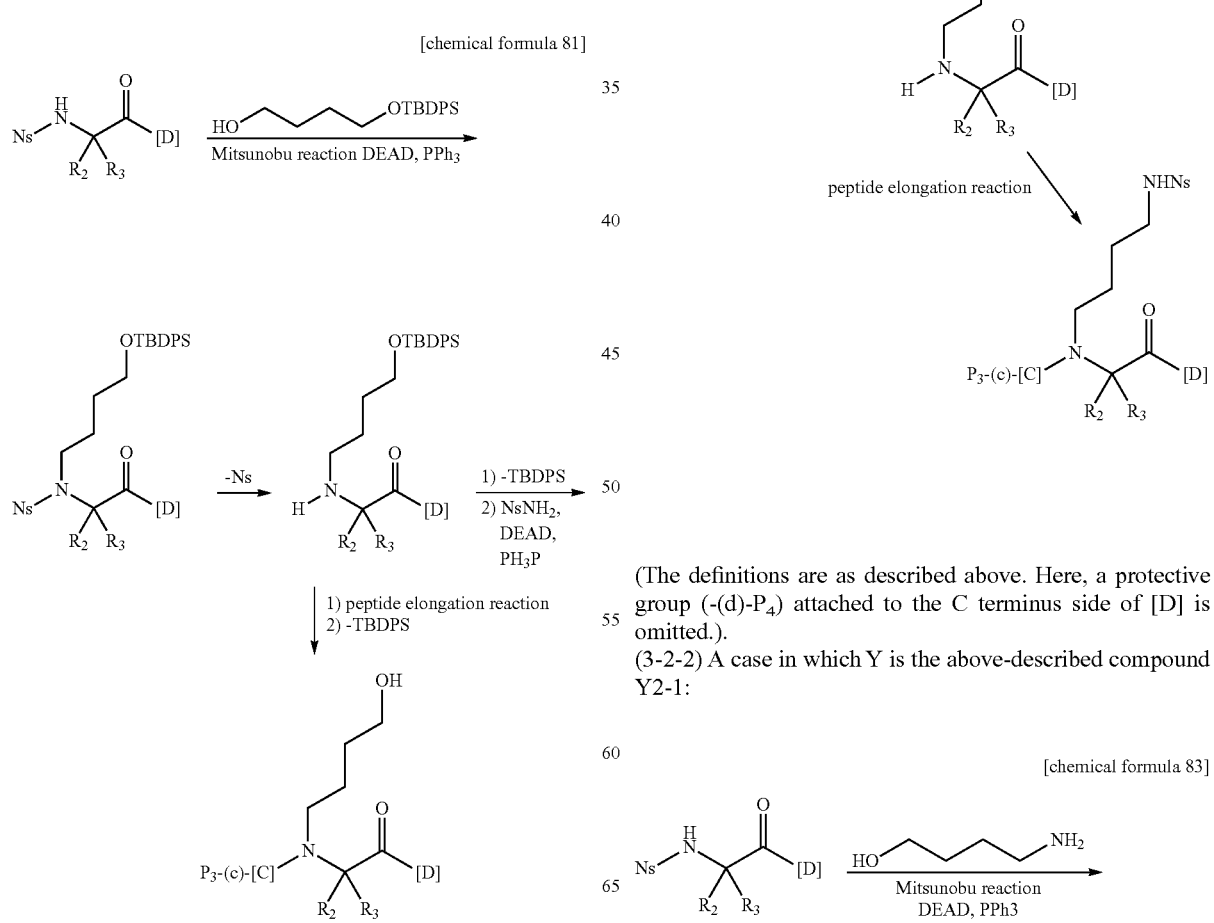

[chemical formula 81]

(The definitions are as described above. Here, a protective group (-(d)-$P_4$) attached to the C terminus side of [D] is omitted.).

(3-2-2) A case in which Y is the above-described compound Y2-1:

[chemical formula 83]

47
-continued
48
-continued
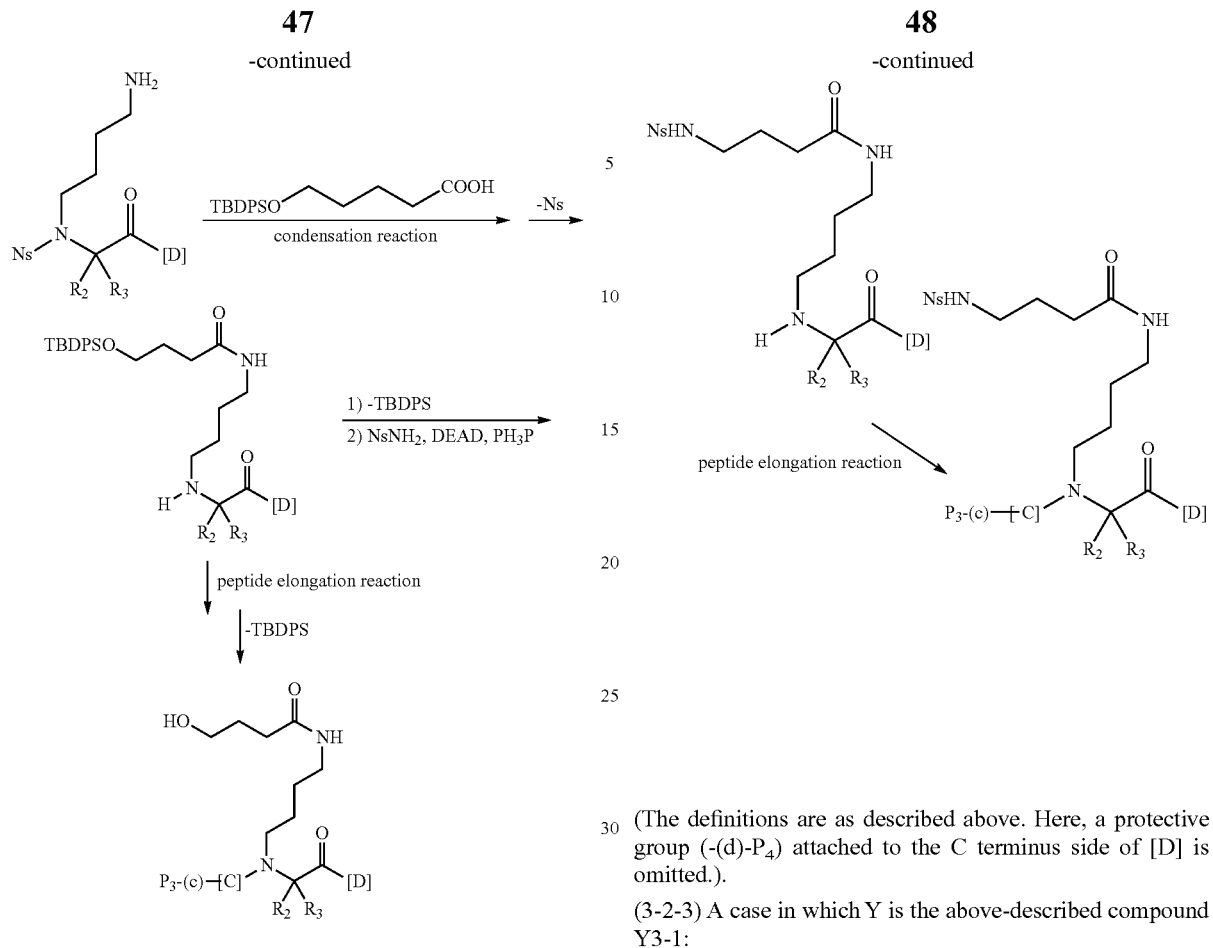
(The definitions are as described above. Here, a protective group (-(d)-$P_4$) attached to the C terminus side of [D] is omitted.).
(3-2-3) A case in which Y is the above-described compound Y3-1:
[chemical formula 84]
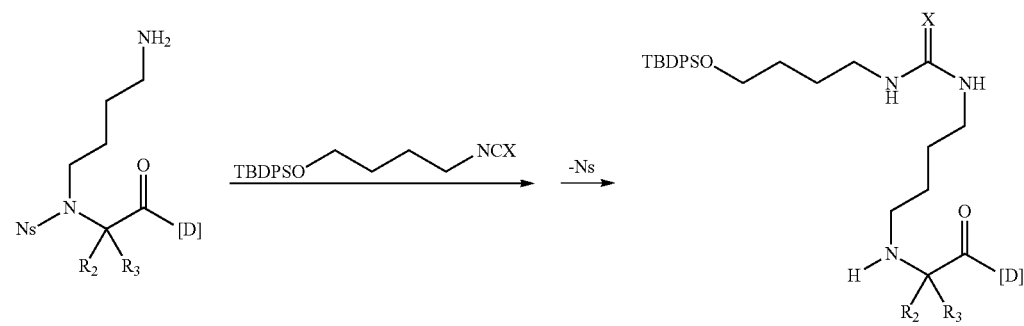

49
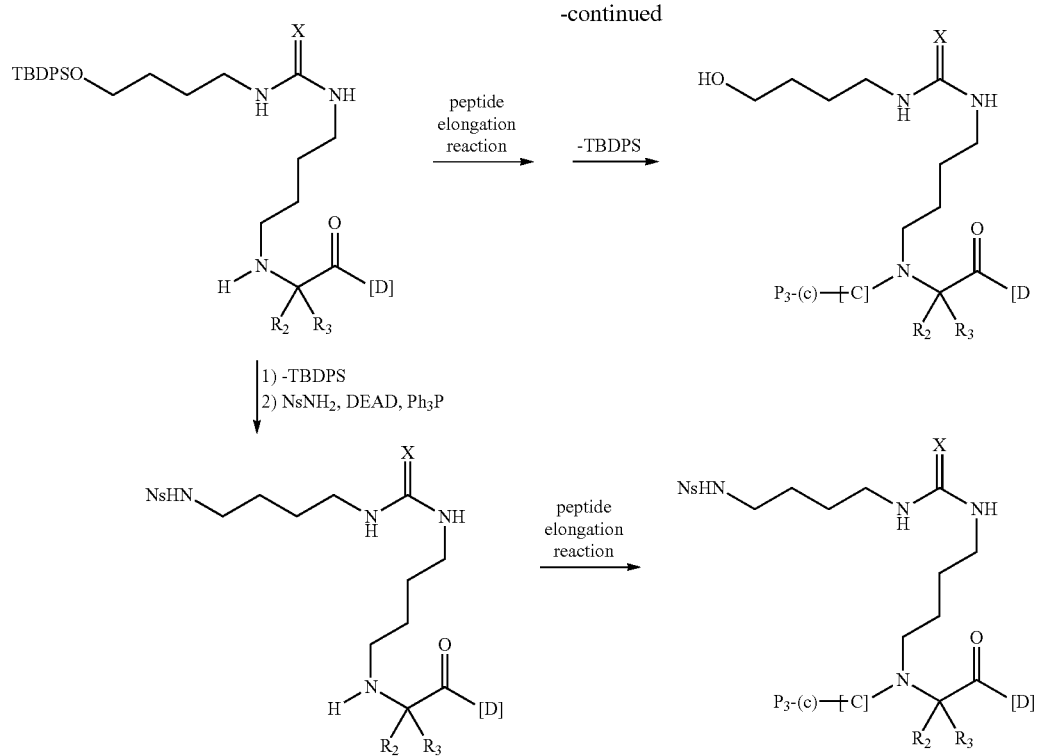
50
(The definitions are as described above, Here, a protective group (-(d)-$P_4$) attached to the C terminus side of [D] is omitted.).
(3-2-4) A case in which Y is the above-described compound Y4-1:
[chemical formula 85]
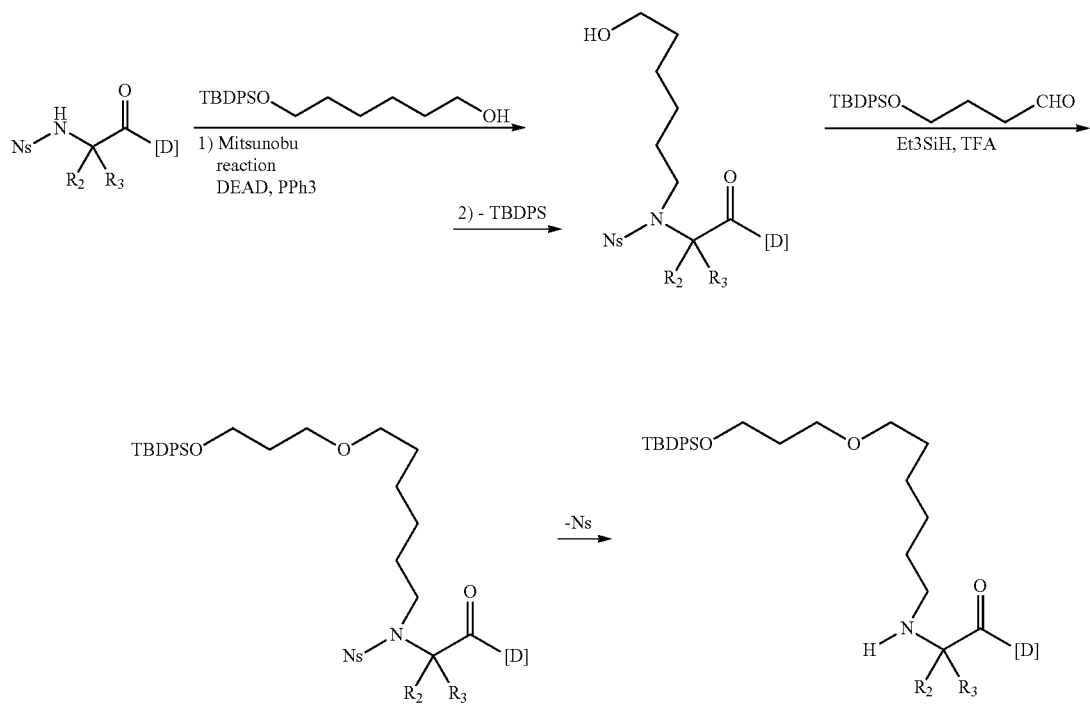

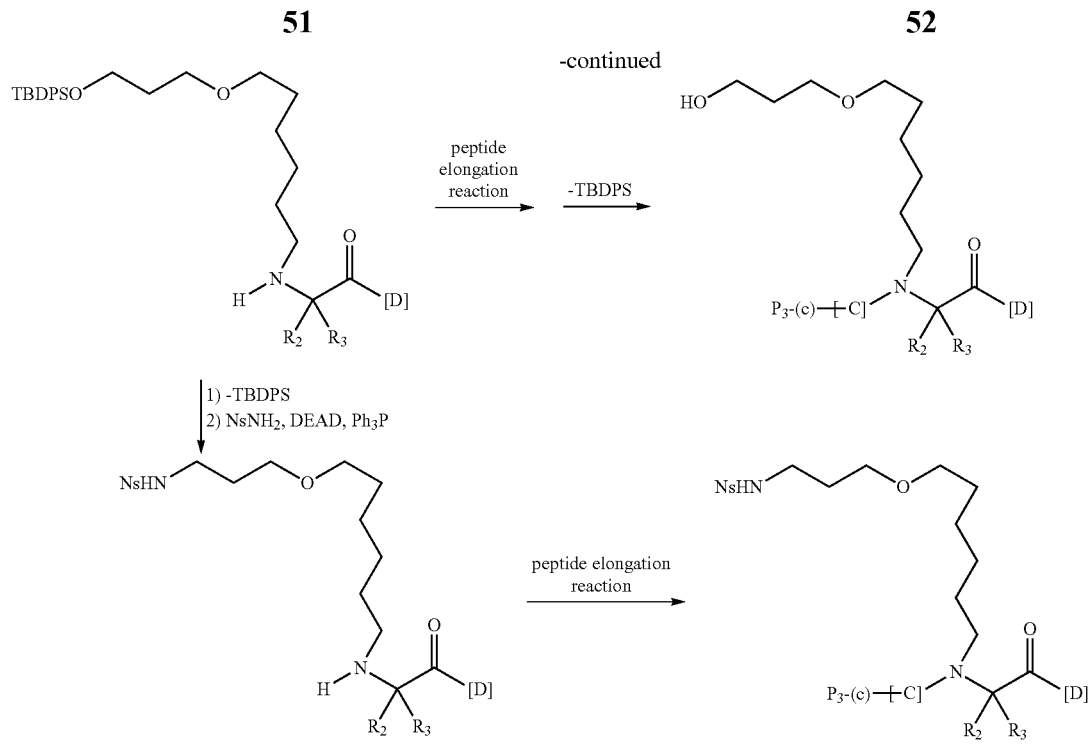
(The definitions are as described above. Here, a protective group (-(d)-$P_4$) attached to the C terminus side of [D] is omitted.).
(3-2-5) A case in which Y is the above-described compound Y5:
[chemical formula 86]
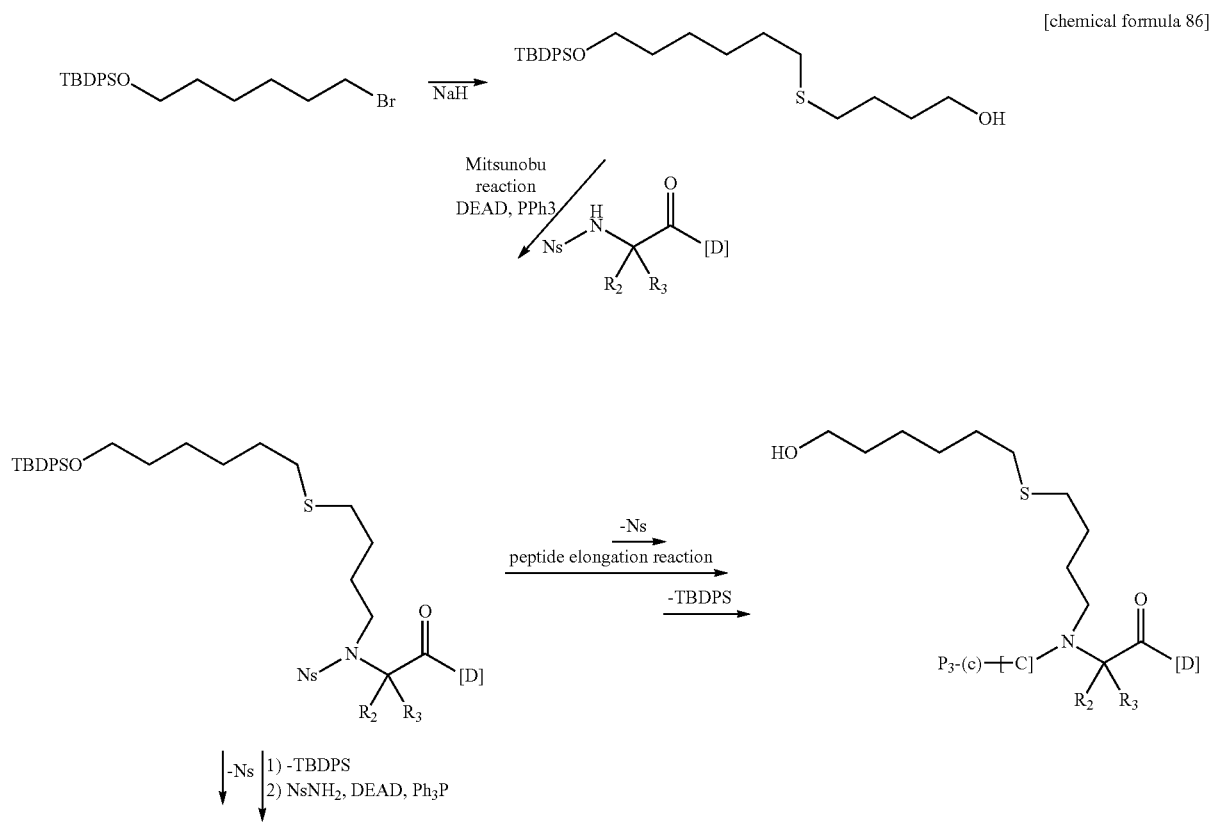

53

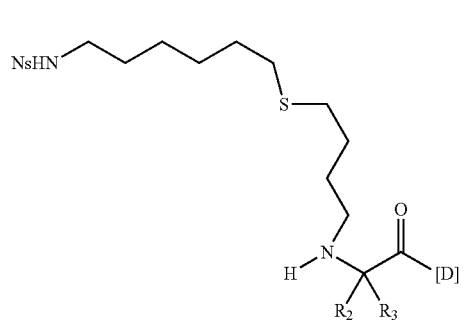

general formula

54

-continued

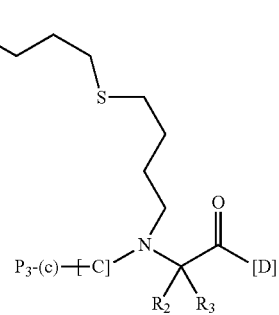

peptide elongation reaction

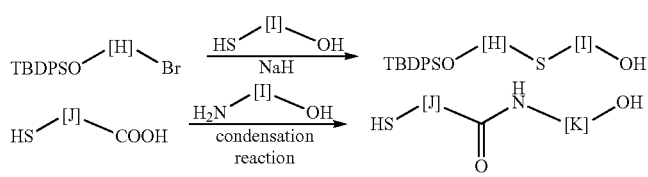

(The definitions are as described above. Here, a protective group (-(d)-P$_4$) attached to the C terminus side of [D] is omitted.).

(3-3. Step of Converting Functional Group)

If necessary, it is also possible, in preparation of a first component or a second component, to convert the functional group of a linker contained therein into a form with which the linker can be subjected to the subsequent cross-linkage forming reaction. As the method of converting a functional group, known methods can be used, and, for example, when deprotecting a TBDPS group, it can be carried out with tetrabutylammonium fluoride, and when converting a hydroxyl group into an aldehyde, it can be carried out by the Dess-Martin oxidation reaction.

(3-4. Synthesis of Intermediate)

Next, the intermediate (M-1) of the present invention can be synthesized by linking an X side component and a Y side component. The condensation reaction can be carried out by a method known to those skilled in the art, and examples thereof include, but not limited to, the Mitsunobu reaction, a reductive amination reaction or the Aza-Wittig reaction and the subsequent reduction reaction. Particularly, the Mitsunobu reaction is preferable. By this, an intermediate can be synthesized having a structure in which a first component and a second component are linked via a secondary amine or a tertiary amine. Examples of synthesis of an intermediate include, but not limited to, reactions described below, and those skilled in the art can make various changes using known technologies.

pattern 1

[chemical formula 87]

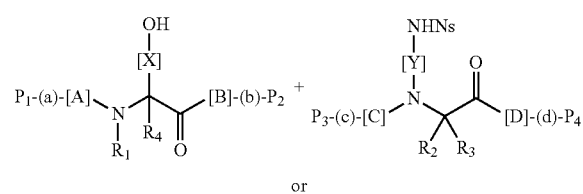

or pattern 2

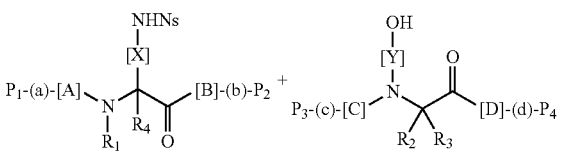

Mitsunobu reaction
DEAD, PPh3

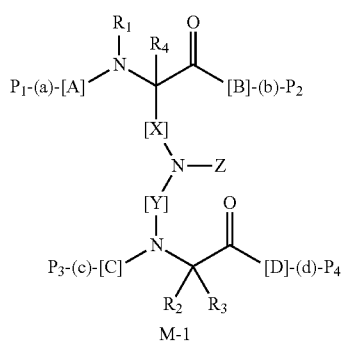

M-1

(wherein, the definitions of marks are as described above.)

In the above-described reaction, it is necessary for the X side component and the Y side component that one of their ends pointing to the cross-linkage center of the cross-linked peptide to be synthesized is —NHNs and the other is —OH.

An example of synthesis of an intermediate using a reductive amination reaction or the Aza-Wittig reaction and the subsequent reduction reaction will be illustrated below, as another embodiment of the condensation reaction.

[chemical formula 88]

pattern 1

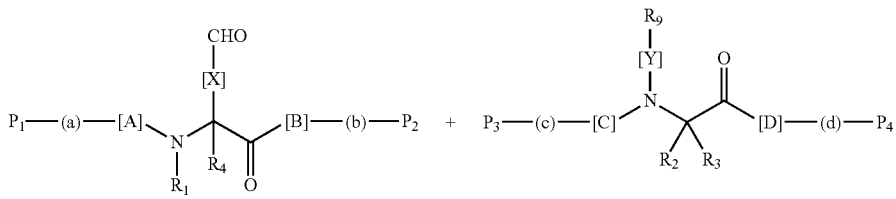

or pattern 2

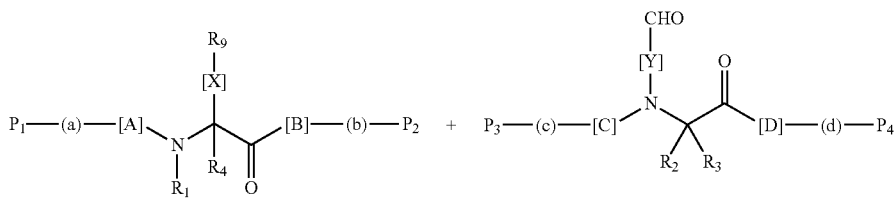

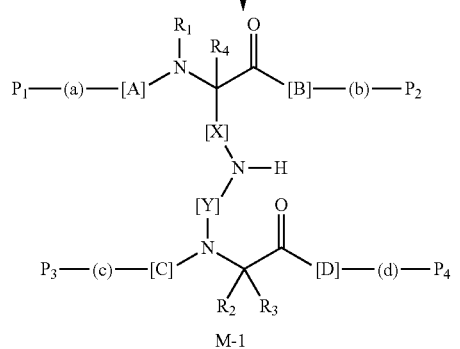

(wherein, the definitions of marks are as described above. Here, $R_9$ represents a $NH_2$ group or a $N_3$ group.).

In the above-described reaction, it is necessary for the X side component and the Y side component that one of their ends pointing to the cross-linkage center of the cross-linked peptide to be synthesized is —$NH_2$ or —$N_3$ and the other is —CHO.

The intermediate (M-4) of the present invention can be synthesized by mutually reacting X side components, for example, using the Mitsunobu reaction, but the synthesis method is not limited to this. For example, the intermediate can be synthesized by the following reaction, but the synthesis method is not limited to the following reaction, and those skilled in the art can make various changes using known technologies.

[chemical formula 89]

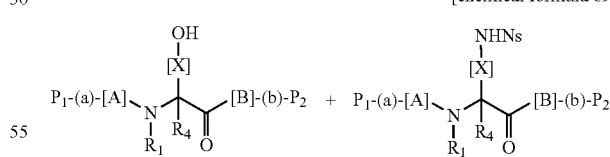

Mitsunobu reaction
DEAD, PPh3

-continued

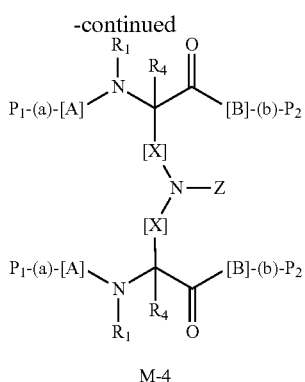

M-4

(wherein, the definitions of marks are as described above, however, those represented by the same mark in the formula may be the same or different.).

The intermediate (M-5) of the present invention can be synthesized by mutually reacting Y side components, for example, using the Mitsunobu reaction, but the synthesis method is not limited to this. For example, the intermediate can be synthesized by the following reaction, but the synthesis method is not limited to the following reaction, and those skilled in the art can make various changes using known technologies.

[chemical formula 90]

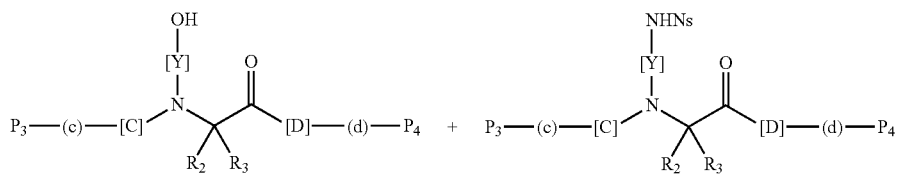

Mitsunobu reaction
DEAD, PPh3

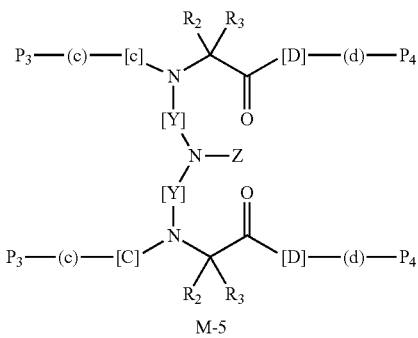

M-5

(wherein, the definitions of marks are as described above, however, those represented by the same mark in the formula may be the same or different.).

4. Method of Synthesis of Cross-Linked Peptide of the Present Invention

Synthesis of a cross-linked peptide as one embodiment of the present invention can be carried out via the following steps:

(a) a step of synthesizing a first component having a structure described below (X side component):

[chemical formula 91]

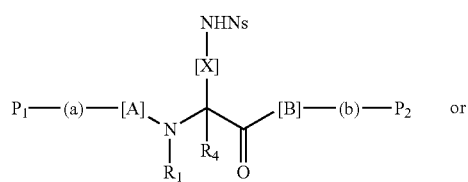

or

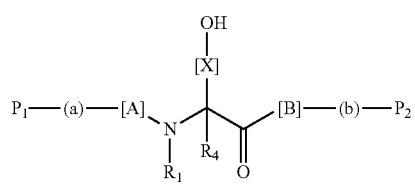

(The definitions are as described above.), (b) a step of synthesizing a second component having a structure described below (Y side component):

[chemical formula 92]

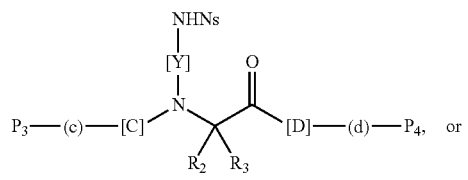

or

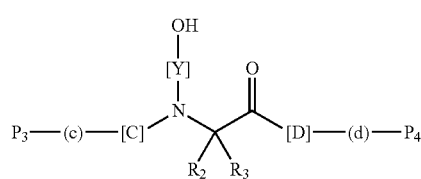

(The definitions are as described above.), (c) a step of reacting the above-described first component (X side component) and the above-described second component (Y side component) to synthesize an intermediate described below:

[chemical formula 93]

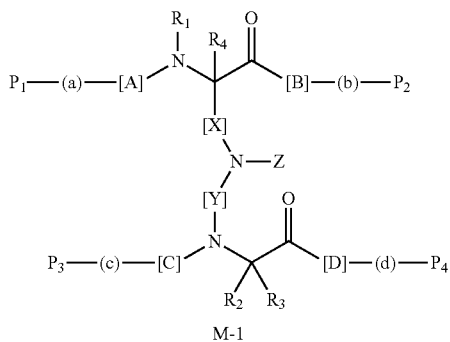

M-1

(The definitions are as described above.), and (d) a step of synthesizing a cross-linked peptide described below from the above-described intermediate, by a condensation reaction:

[chemical formula 94]

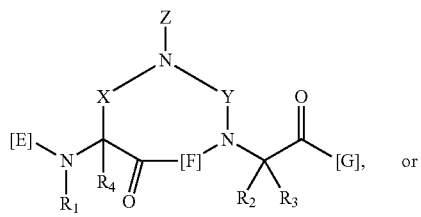

P-1

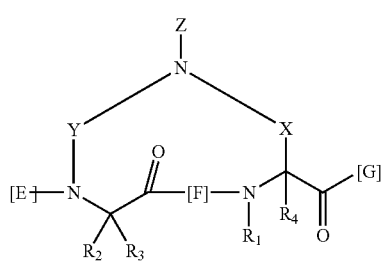

P-2

That is, the method of synthesizing a cross-linked peptide as one embodiment of the present invention can be carried out by a step containing the following steps (a) to (g):

(a) a step of preparing a first component (component A), comprising the following steps, (a-1) a step of, if necessary, condensing a carboxyl protective group with amino acids or a peptide constituting a partial peptide sequence of the cross-linked peptide, and further, if necessary, elongating the condensed group, (a-2) a step of reacting the N-terminus side of the peptide or amino acid synthesized or the carboxyl protective group with an amino acid derivative containing in the side chain a linker forming part of a cross-linkage of the cross-linked peptide, to synthesize the peptide having the linker in the side chain or the amino acid derivative having the carboxyl group protected, (a-3) a step of, if necessary, further performing a peptide elongation reaction to elongate the peptide, and (a-4) a step of, if necessary (that is, when the linker end is not reactive), converting the functional group of the linker into a form with which the linker can be subjected to the subsequent cross-linkage forming reaction, (b) a step of preparing a second component (component B), comprising the following steps,
- (b-1) a step of condensing a carboxyl protective group with amino acids or a peptide constituting a partial peptide sequence of the cross-linked peptide, and if necessary, elongating the condensed group,
- (b-2) a step of reacting the N-terminus of the peptide or a reaction site (for example, N-terminus) of the amino acid derivative synthesized with a compound containing a linker forming part of a cross-linkage of the cross-linked peptide, to synthesize a peptide or an amino acid derivative having a secondary amine at the N-terminus containing the linker,
- (b-3) a step of, if necessary, further performing a peptide elongation reaction to elongate the peptide, and
- (b-4) a step of, if necessary (that is, when the linker end is not reactive), converting the functional group of the linker into a form with which the linker can be subjected to the subsequent cross-linkage forming reaction,
- (c) a step of linking the first component (A) and the second component (B) by the Mitsunobu reaction, a reductive amination reaction or the Aza-Wittig reaction and the subsequent reduction reaction, to prepare an intermediate having a structure in which the first component and the second component are linked via a secondary amine or a tertiary amine,
- (d-1) a step of, if necessary, deprotecting a protective group at the peptide N-terminus of the first component (A) or the second component (B),
- (d-2) a step of, if necessary, deprotecting a protective group at the peptide C-terminus of the first component (A) or the second component (B),
- (e) a step of condensing the peptide N- or C-terminus of the first component (A) with the peptide C- or N-terminus of the second component (B) to form a cross-linkage,
- (f) a step of, if necessary, post-processing the cross-linked peptide by any method known to those skilled in the art, and
- (g) a step of, if necessary, deprotecting the protective group.

Synthesis of a cross-linked peptide described below as another embodiment of the present invention can be carried out by a step comprising the following steps (a) to (g):

[chemical formula 95]

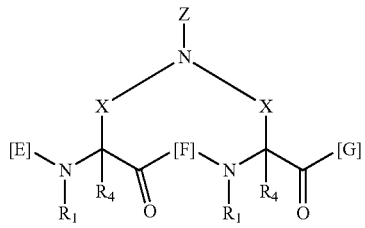

P-3

(a) a step of preparing a first component (component A1), comprising the following steps,
- (a-1) a step of, if necessary, condensing a carboxyl protective group with amino acids or a peptide constituting a partial peptide sequence of the cross-linked peptide, and further, if necessary, elongating the condensed group,
- (a-2) a step of reacting the N-terminus side of the peptide or amino acid synthesized or the carboxyl protective group with an amino acid derivative containing in the side chain a linker forming part of a cross-linkage of the cross-linked peptide, to synthesize the peptide having the linker in the side chain or the amino acid derivative having the carboxyl group protected,
- (a-3) a step of, if necessary, further performing a peptide elongation reaction to elongate the peptide, and
- (a-4) a step of, if necessary (that is, when the linker end is not reactive), converting the functional group of the linker into a form with which the linker can be subjected to the subsequent cross-linkage forming reaction,
- (b) a step of preparing a second component (component A2), comprising the following steps,
  - (b-1) a step of, if necessary, condensing a carboxyl protective group with amino acids or a peptide constituting a partial peptide sequence of the cross-linked peptide, and further, if necessary, elongating the condensed group,
  - (b-2) a step of reacting the N-terminus side of the peptide or amino acid synthesized or the carboxyl protective group with an amino acid derivative containing in the side chain a linker forming part of a cross-linkage of the cross-linked peptide, to synthesize the peptide containing the linker in the side chain or the amino acid derivative having the carboxyl group protected,
  - (b-3) a step of, if necessary, further performing a peptide elongation reaction to elongate the peptide, and
  - (b-4) a step of, if necessary (that is, when the linker end is not reactive), converting the functional group of the linker into a form with which the linker can be subjected to the subsequent cross-linkage forming reaction,
- (c) a step of linking the first component (A1) and the second component (A2) by the Mitsunobu reaction, a reductive amination reaction or the Aza-Wittig reaction and the subsequent reduction reaction, to prepare an intermediate having a structure in which the first component (A1) and the second component (A2) are linked via a secondary amine or a tertiary amine,
- (d-1) a step of, if necessary, deprotecting a protective group at the peptide N-terminus of the first component (A1) or the second component (A2),
- (d-2) a step of, if necessary, deprotecting a protective group at the peptide C-terminus of the first component (A1) or the second component (A2),
- (e) a step of condensing the peptide N- or C-terminus of the first component (A1) with the peptide C- or N-terminus of the second component (A2) to form a cross-linkage,
- (f) a step of, if necessary, post-processing the cross-linked peptide by any method known to those skilled in the art, and
- (g) a step of, if necessary, deprotecting the protective group.

Synthesis of a cross-linked peptide described below as still another embodiment of the present invention can be carried out by a step comprising the following steps (a) to (g):

[chemical formula 96]

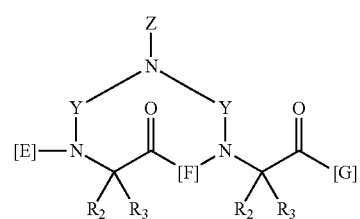

P-4

(a) a step of preparing a first component (component B1), comprising the following steps,
- (a-1) a step of condensing a carboxyl protective group with amino acids or a peptide constituting a partial peptide sequence of the cross-linked peptide, and if necessary, elongating the condensed group,
- (a-2) a step of reacting the N-terminus of the peptide or a reaction site (for example, N-terminus) of the amino acid derivative synthesized with a compound containing a linker forming part of a cross-linkage of the cross-linked peptide, to synthesize a peptide or an amino acid derivative having a secondary amine at the N-terminus containing the linker,
- (a-3) a step of, if necessary, further performing a peptide elongation reaction to elongate the peptide, and
- (a-4) a step of, if necessary (that is, when the linker end is not reactive), converting the functional group of the linker into a form with which the linker can be subjected to the subsequent cross-linkage forming reaction, (b) a step of preparing a second component (component B2), comprising the following steps,
- (b-1) a step of condensing a carboxyl protective group with amino acids or a peptide constituting a partial peptide sequence of the cross-linked peptide, and if necessary, elongating the condensed group,
- (b-2) a step of reacting the N-terminus of the peptide or the amino acid derivative synthesized with a compound containing a linker forming part of a cross-linkage of the cross-linked peptide, to synthesize a peptide or an amino acid derivative having a secondary amine at the N-terminus containing the linker,
- (b-3) a step of, if necessary, further performing a peptide elongation reaction to elongate the peptide, and
- (b-4) a step of, if necessary (that is, when the linker end is not reactive), converting the functional group of the linker into a form with which the linker can be subjected to the subsequent cross-linkage forming reaction, (c) a step of linking the first component (B1) and the second component (B2) by the Mitsunobu reaction, a reductive amination reaction or the Aza-Wittig reaction and the subsequent reduction reaction, to prepare an intermediate having a structure in which the first component and the second component are linked via a secondary amine or a tertiary amine, (d-1) a step of, if necessary, deprotecting a protective group at the peptide N-terminus of the first component (B1) or the second component (B2), (d-2) a step of, if necessary, deprotecting a protective group at the peptide C-terminus of the first component (B1) or the second component (B2), (e) a step of condensing the peptide N- or C-terminus of the first component with the peptide C- or N-terminus of the second component to form a cross-linkage, (f) a step of, if necessary, post-processing the cross-linked peptide by any method known to those skilled in the art, and (g) a step of, if necessary, deprotecting the protective group.

A cross-linked peptide represented by (P-1) as one embodiment of the present invention is used by way of example and steps thereof will be illustrated more specifically below.

4-1. Synthesis of a first component (X side component) comprises the following step:
that is, a step of fabricating a first component containing a linker introduced, by a method comprising
- (1-1) a step of preparing any amino acid in which the C-terminus is protected with a hydrophobic carrier,
- (1-2) a step of elongating a peptide using a condensation reaction and a deprotection method usually known,
- (1-3) a step of introducing a linker, by protecting an amino group of an amino acid side chain acting as a linker with a nosyl group or condensing an amino acid having a nosyl-protected amino group in the side chain or an amino acid having a protected hydroxyl group in the side chain,
- (1-4) a step of, if necessary, introducing an alkylene chain acting as a cross-link portion onto a hydroxyl group,
- (1-5) a step of, if necessary, further continuing a condensation reaction to elongate the peptide,
- (1-6) a step of, if necessary, converting the functional group of the linker into a form with which the linker can be subjected to the subsequent cross-linkage forming reaction, and
- (1-7) a step of, if necessary, introducing a —NHNs group to the linker.

By the above-described method, a first component (X side component) can be synthesized in which the linker is an OH group or a protected OH group or the end is an NHNs group.

As the above-described hydrophobic carrier used for peptide synthesis of a first component, any of carriers for solid phase synthesis and carriers for liquid phase synthesis can be used, and preferable are hydrophobic carriers which can be used for liquid phase synthesis. The above-described alkoxy-substituted benzyl groups Ka, Kb and Kc are particularly preferably used, though there is no specific restriction.

4-2. Synthesis of a second component (Y side component) comprises the following step:
that is, a step of fabricating a second component containing a linker introduced, by a method comprising
- (2-1) a step of preparing any amino acid in which the C-terminus is protected with a hydrophobic carrier,
- (2-2) a step of elongating a peptide using a condensation reaction and a de-protection method usually known,
- (2-3) a step of protecting an α-amino group of an amino acid as a site to which a linker is introduced with a nosyl group, or condensing an amino acid having a nosyl-protected α-amino group,
- (2-4) a step of introducing a protected OH group using the Mitsunobu reaction or other methods,
- (2-5) a step of, if necessary, further continuing a condensation reaction to elongate the peptide,
- (2-6) a step of, if necessary, converting the functional group of the linker into a form with which the linker can be subjected to the subsequent cross-linkage forming reaction, and
- (2-7) a step of, if necessary, introducing a —NHNs group to the end of the cross-link portion.

By the above-described method, a second component (Y side component) can be synthesized in which the linker is an OH group or a protected OH group or the end is an NHNs group.

As the above-described hydrophobic carrier used for peptide synthesis of a second component, any of carriers for solid phase synthesis and carriers for liquid phase synthesis can be used, and preferable are hydrophobic carriers which can be used for liquid phase synthesis. The above-described alkoxy-substituted benzyl groups Ka, Kb and Kc are particularly preferably used, though there is no specific restriction.

Next, a first component and a second component are reacted to synthesize an intermediate. Then, the resultant intermediate is condensed to fabricate a cross-linked peptide of the present invention. In such a case, Ka, Kb and Kc are preferably used to control which of the N-terminus and the C-terminus of the first and second components should be cyclized. Particularly, it is preferable that Ka or Kc is linked as a protective group to one end and Kb is linked as a protective group to the other end, since selective de-protection can be performed easily in this case.

4-3. Linking of a first component and a second component can be accomplished, for example, by combining a phosphine reagent such as triphenylphosphine and the like with a Mitsunobu reagent such as diethyl azodicarboxylate and the like and performing the Mitsunobu reaction to link a cross-link portion of the first component and a cross-link portion of the second component. They can also be linked (cross-linked) by a reductive amination reaction or the Aza-Wittig reaction and the subsequent reduction reaction.

4-4. The step of forming a peptide bond (peptide chain) by a condensation reaction can be accomplished by subjecting any one C-terminus and any one N-terminus of an intermediate to a condensation reaction known to those skilled in the art using a condensation agent such as HATU, HBTU or TBTU and the like.

The synthesis method of the present invention can include a denosylation step of cutting a nosyl group of a synthesized cross-linked peptide, using thiophenol and DBU.

The synthesis method of the present invention can include, if necessary, a step of performing suitable chemical modification before the global deprotection.

The synthesis method of the present invention can include a step of deprotecting a side chain protective group of an amino acid of a cross-linked peptide by an acid or reduction treatment, thereby fabricating a naked cross-linked peptide.

The synthesis method of the present invention can include, if necessary, a step of performing suitable chemical modification after the global deprotection.

The method of separately synthesizing two components, for example, an X side component and a Y side component has merits that a longer peptide can be easily synthesized, or the kinds and lengths of endocyclic and exocyclic peptides can be freely designed and synthesized, further, a linker portion can be determined freely. Further, such a method has merits that a cross-link portion (portion corresponding to X and Y) can be optionally selected and the length and the kind thereof can be easily adjusted.

As the condensation reaction used in the present invention, any method can be used providing it is a method usually known in the field of amino acid synthesis in a solid phase or a liquid phase.

As the de-protection reaction used in the present invention, any method can be used providing it is a method usually known or used in the field of amino acid synthesis, and examples thereof include a Fmoc method, a Boc method and a Z method.

The method of protecting an amino acid with nosyl used in the present invention can be carried out by, for example, a method of introducing nosylamide to a hydroxyl group by the Mitsunobu reaction or a method of reacting an amino group with nosyl chloride, however, the protecting method is not limited to them, and it can be carried out using a method usually known in the field of amino acid synthesis.

The nosyl-protected amino acid used in the present invention can be prepared, for example, by Fmoc-Lys-OH, however, the method is not limited to this, and it can be prepared using a method usually known.

As the method of protecting an OH functional group of a compound capable of constituting part of a cross-linkage used in the present invention, any method can be used providing it is a method usually known in the field of amino acid synthesis, and it can be carried out using, for example, TMS (trimethylsilyl), TIPS (triisopropylsilyl) or TBDPS (tert-butyldiphenylsilyl), and TBDPS is preferably used. The reaction can be carried out according to an ordinary method.

A compound constituting part of a cross-linkage in which an OH functional group is thus protected is introduced into a peptide. Examples of the introduction method include, but not specifically limited to, the Mitsunobu reaction, a reductive amination reaction and a condensation reaction, and the Mitsunobu reaction is preferably used.

Here, the kind and the length of the chemical structure constituting part of a cross-linkage can be optionally selected and not particularly restricted as described previously in the present specification, and examples thereof can include an alkylene chain, an alkyl chain, an ether chain, a thioether chain, an amide chain, a urethane chain, a thiourethane chain and a polyethylene glycol chain, and preferable are an alkylene chain, an alkyl chain, an ether chain and a polyethylene glycol chain. In the case of selection of a cross-linkage not containing a disulfide bond and an amide bond in the cross-linked structure, there is a merit of good resistance to enzymatic degradation, for example, excellent stability against a peptidase and the like, as compared with conventional cross-linked peptides having a disulfide bond and an amide bond.

EXAMPLES

Methods of synthesizing a cross-linked peptide of the present invention will be illustrated using byway of example a WP9QY (W9) peptide having a peptide sequence structure containing a cross-linkage shown below, but the present invention is not limited to them.

[chemical formula 97]

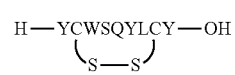

In the present specification and in the following examples, abbreviations shown below were used.

TABLE 1

Ac$_2$O: Acetic anhydride
Boc: tert-Butoxycarbonyl
CH$_2$Cl$_2$ (DCM): DichloromethaneCH$_3$CN: Acetonitrile
CHCl$_3$: Chloroform
DBU: 1,8-Diazabicyclo[5.4.0]undec-7-ene
DEAD: Diethyl azodicarboxylate
DIPCI: N,N'-Diisopropylcarbodiimide
DIPEA: N,N'-Diisopropylethylamine
DMAP: 4-Dimethylaminopyridine
DMF: N,N-Dimethylformamide
DMSO: Dimethyl sulfoxide
DMT-MM: 4-(4,6-Dimethoxv-1,3,5-triazin-2-yl)-4-methylmorpholinium chloride
EDT: Ethanedithiol
Et$_3$N: Triethylamine
EtOAc: Ethyl acetate
EtOH: Ethanol
Fmoc: 9-Fluorenylmethoxycarbonyl
HATU: O-(7-Azabenzotriazole-1-yl)1,1,3,3-tetramethyluronium hexafluorophosphate
HBTU: 2-(1H-Benzotriazole-1-yl)1,1,3,3-tetramethyluronium hexafluorophosphate
HOAt: 1-Hydroxy-7-azabenzotriazole
HOBt: 1-Hydroxybenzotriazole
IPE: Diisopropyl Ether
Ka: 3,4,5-Tri-octadesylbenzyl
Kb: 2,4-Di-docosyloxybenzyl
MCA: Chloroacetyl
MeOH: Methanol
Mmt: p-Methoxytrityl
Mtt: p-Methyltrityl

TABLE 1-continued

Myr: Myristyl
Ns-: 2-Nitrobenzenesulfonyl
NsCl: 2-Nitrobenzenesulfonyl chloride
Pbf: 2,2,4,6,7-Pentamethyldihydrobenzofuran-5-sulfonyl
PEG: Polyethyleneglycol
PhSH: Thiophenol
PhSMe: Thioanisole
PPh$_3$: Triphenylphosphine
TBDPS-: tert-Butyldiphenylsilyl
tBu: tert-Butyl
TFA: Trifluoroacetic acid
TFE: 2,2,2-Trifluoroethanol
THF: Tetrahydrofuran
TIS: Triisopropulsilane
Trt: Trityl Synthesis of Cross-Linked Peptide According to the synthesis scheme shown in FIG. 1 and FIG. 2, a cross-linked peptide (Bdev-7) as a peptide mimic of the W9 peptide, having —(CH$_2$)$_4$—NH—(CH$_2$)$_4$— instead of a disulfide bond as the cross-linked structure, was synthesized.

Figure 2:
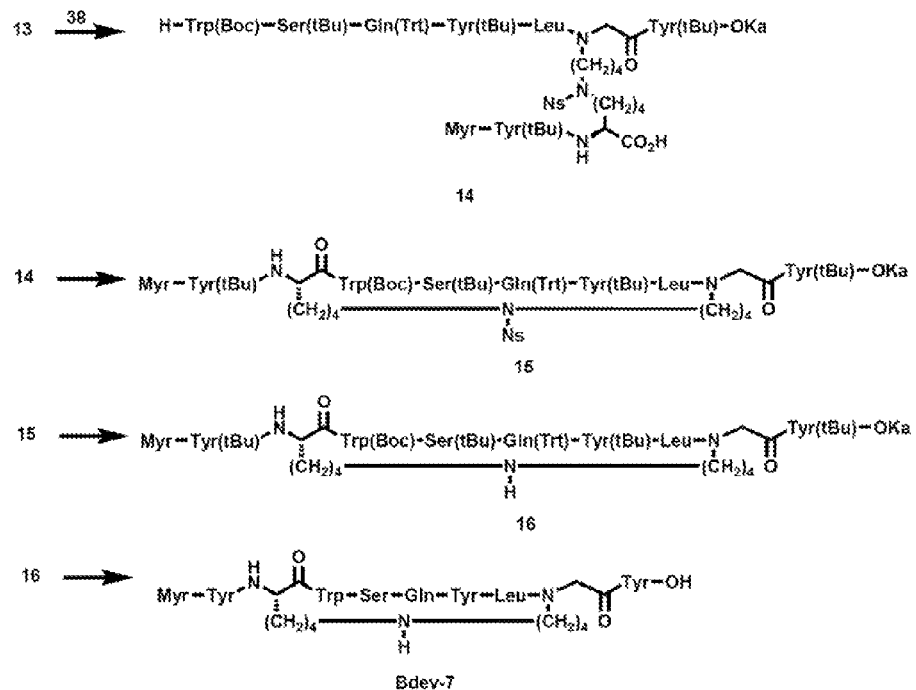
FIG. 2 shows a schematic view of a synthesis example of a W9 cross-linked peptide mimic as a cross-linked peptide of the present invention from an intermediate of the present invention.

FIG. 1 is a schematic view of a synthesis route of a Y side component. FIG. 2 is a schematic view of a synthesis route in which an X side component separately synthesized is linked to a Y side component by the Mitsunobu reaction to synthesize an intermediate (compound 14 in the figure), then, a cross-linked peptide (Bdev-7) of the present invention is synthesized by a condensation reaction. FIG. 1 and FIG. 2 only illustrate one route of synthesizing Bdev-7, and it is, possible to make various alterations and interchange synthesis routes within the scope of the present invention.

Each step will be illustrated in detail below.

Example 1

Synthesis of Intermediate (Compound 13)

Synthesis of Compound 1

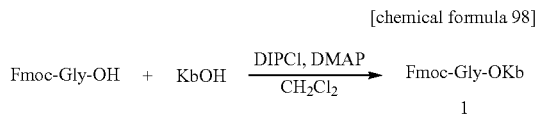

[chemical formula 98]

2,4-didocosoxy benzyl alcohol (denoted as "KbOH") (7.69 g, 10.1 mmol) was dissolved in CH$_2$Cl$_2$ (200 mL), and Fmoc-Gly-OH (4.52 g, 15.2 mmol, 1.5 equiv), DIPCI (3147 µL, 20.2 mmol, 2.0 equiv) and DMAP (12.3 mg, 0.101 mmol, 0.01 equiv) were added and the mixture was stirred at room temperature for 30 minutes. The precipitated material was filtrated, and the filtrate was evaporated under reduced pressure. To the residue was added MeOH to find deposition of a precipitated material, which was then filtrated, suspended and washed with MeOH twice and suspended and washed with CH$_3$CN, to obtain a compound 1 (10.1 g, 96.7%).

Synthesis of Compound 2

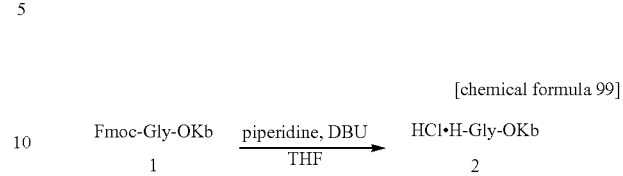

[chemical formula 99]

The compound 1 (10.1 g, 9.74 mmol) was dissolved in THF (200 mL), and piperidine (1863 µL, 17.5 mmol, 1.8 equiv) and DBU (1863 µL, 17.5 mmol, 1.8 equiv) were added and the mixture was stirred at room temperature for 5 minutes. Concentrated hydrochloric acid was added until pH of the reaction solution reached around 6, and the solvent was evaporated under reduced pressure. To the residue was added CH$_3$CN to find deposition of a precipitated material, which was then filtrated, suspended and washed with CH$_3$CN twice, to obtain a compound 2 (8.21 g, 98.7%).

Synthesis of Compound 3

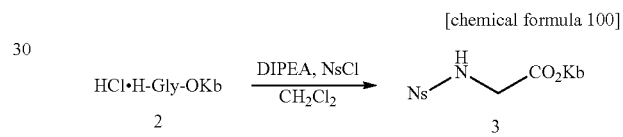

[chemical formula 100]

The compound 2 (7.60 g, 8.96 mmol) was dissolved in CH$_2$Cl$_2$ (180 mL), and DIPEA (3589 µL, 20.6 mmol, 2.3 equiv) and NsCl (2.59 g, 11.7 mmol, 1.3 equiv) were added and the mixture was stirred at room temperature. One hour after, DIPEA (359 µL, 2.06 mmol, 0.2 equiv) was additionally added and the mixture was stirred at room temperature for 19 minutes. To the reaction solution was added MeOH (30 mL), then, the solvent was evaporated under reduced pressure. To the residue was added CH$_3$CN to find deposition of a precipitated material, which was then filtrated, suspended and washed with CH$_3$CN twice, to obtain a compound 3 (8.95 g, 99.9%).

Synthesis of Compound 4

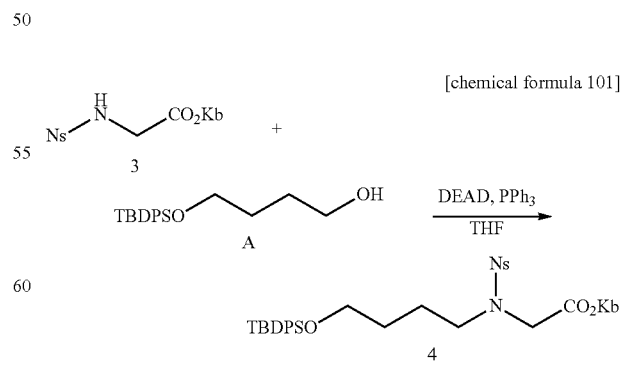

[chemical formula 101]

The compound 3 (4.70 g, 4.71 mmol) and the compound A [1] (3.11 g, 9.46 mmol, 2.0 equiv) were dissolved in THF (94 mL), PPh$_3$ (2.49 g, 9.50 mmol, 2.0 equiv) and DEAD (4272

μL, 9.42 mmol, 2.0 equiv) were added and the mixture was stirred at room temperature for 3 hours. PPh$_3$ (248 mg, 0.946 mmol, 0.2 equiv) and DEAD (427 μL, 0.942 mmol, 0.2 equiv) were added and the mixture was stirred for 1 hour. PPh$_3$ (245 mg, 0.934 mmol, 0.2 equiv) and DEAD (427 μL, 0.942 mmol, 0.2 equiv) were added and the mixture was stirred for 1 hour and 15 minutes, then, the solvent was evaporated under reduced pressure. To the residue was added CH$_3$CN to find deposition of a precipitated material, which was then filtrated, suspended and washed with CH$_3$CN twice, to obtain a compound 4 (6.12 g, 99.2%).

Synthesis of Compound 5

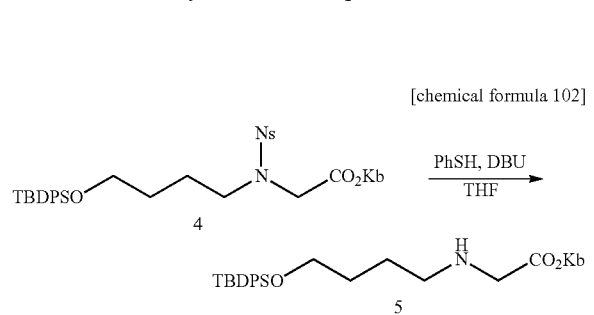

[chemical formula 102]

The compound 4 (5.65 g, 4.31 mmol) was dissolved in THF (40 mL), PhSH (1328 μL, 12.9 mmol, 3.0 equiv) and DBU (1934 μL, 12.9 mmol, 3.0 equiv) were added and the mixture was stirred at room temperature for 1 hour and 30 minutes. To the reaction solution was added CH$_3$CN (200 mL) to find deposition of a precipitated material, which was then filtrated, suspended and washed with CH$_3$CN twice, to obtain a compound 5 (4.77 g, 98.4%).

Synthesis of Compound 6

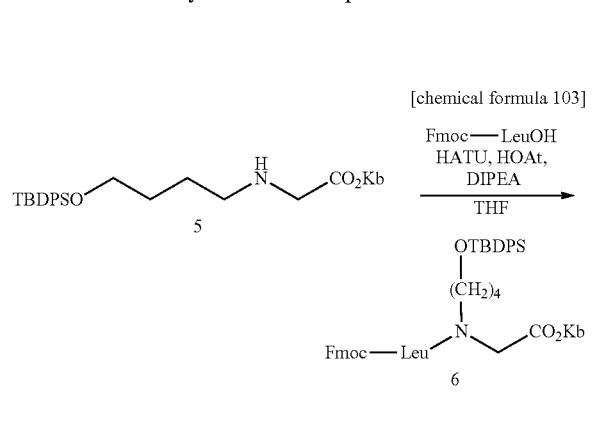

[chemical formula 103]

The compound 5 (7.49 g, 6.65 mmol) was dissolved in THF (70 mL), and Fmoc-Leu-OH (3.53 g, 9.98 mmol, 1.5 equiv), HOAt (2.27 g, 16.7 mmol, 2.5 equiv), HATU (6.32 g, 16.6 mmol, 2.5 equiv) and DIPEA (5800 μL, 33.3 mmol, 5.0 equiv) were added and the mixture was stirred at room temperature for 6 minutes. DIPEA (580 μL, 3.33 mmol, 0.5 equiv) was added and the mixture was stirred for 8 minutes. DIPEA (580 μL, 3.33 mmol, 0.5 equiv) was added and the mixture was stirred for 1 hour. The precipitated material was filtrated, and the filtrate was evaporated under reduced pressure. The same post treatment as in synthesis of the compound 4 was conducted to obtain a residue, which was then subjected to silica gel column chromatography (n-hexane/EtOAc=100:0-85:15), to obtain a compound 6 (9.10 g, 93.7%).

Synthesis of Compound 7

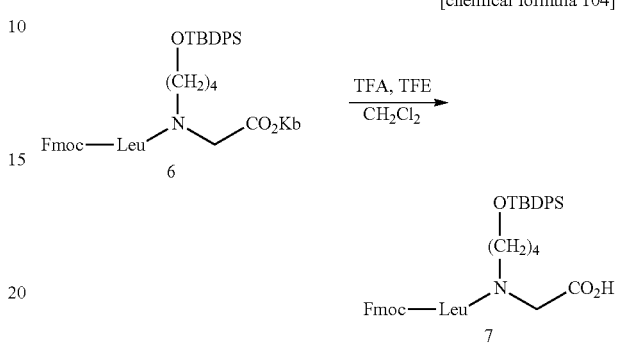

[chemical formula 104]

The compound 6 (1.05 g, 0.721 mmol) was dissolved in CH$_2$Cl$_2$ (36 mL), and TFE (3.6 mL) and TFA (360 μl) were added and the mixture was stirred at room temperature for 40 minutes. The precipitated material was filtrated, and the filtrate was evaporated under reduced pressure. To the residue was added CH$_2$Cl$_2$ and the mixture was washed with water three times, the organic layer was washed with saturated saline, dried over anhydrous MgSO$_4$, filtrated and the filtrate was evaporated under reduced pressure. The residue was subjected to silica gel column chromatography (CH$_2$Cl$_2$/MeOH, 100:0-90:10), to obtain a compound 7 (478 mg, 92.2%).

Synthesis of Compound 8

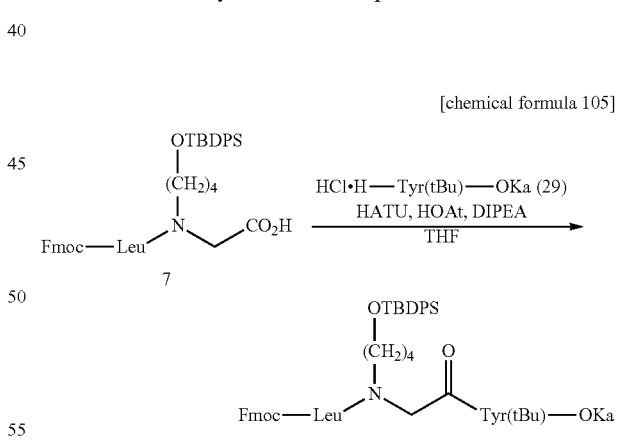

[chemical formula 105]

The compound 7 (4.08 g, 5.66 mmol, 1.2 equiv) was dissolved in THF (70 mL), and the compound 29 (synthesis method is described later) (5.52 g, 4.72 mmol), DIPCI (1104 μL, 7.09 mmol, 1.5 equiv), HOAt (963 mg, 7.08 mmol, 1.5 equiv) and DIPEA (4940 μL, 28.4 mmol, 6.0 equiv) were added and the mixture was stirred at room temperature for 3 hours. HOAt (325 mg, 2.39 mmol, 0.5 equiv) and DIPCI (368 μL, 2.36 mmol, 0.5 equiv) were added and the mixture was stirred for 2 hours. The solvent was evaporated under reduced pressure, then, the same post treatment as in synthesis of the compound 1 was conducted, to obtain a compound 8 (8.54 g, 98.5%).

Synthesis of Compound 9

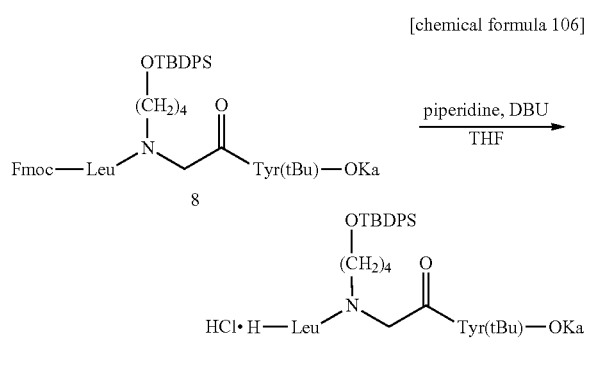

The compound 8 (8.54 g, 4.65 mmol) was dissolved in THF (93 mL), and piperidine (891 μL, 8.37 mmol, 1.8 equiv) and DBU (904 μL, 6.04 mmol, 1.3 equiv) were added and the mixture was stirred at room temperature for 5 minutes. The same post treatment as in synthesis of the compound 2 was conducted, to obtain a de-Fmoc form (8.31 g).

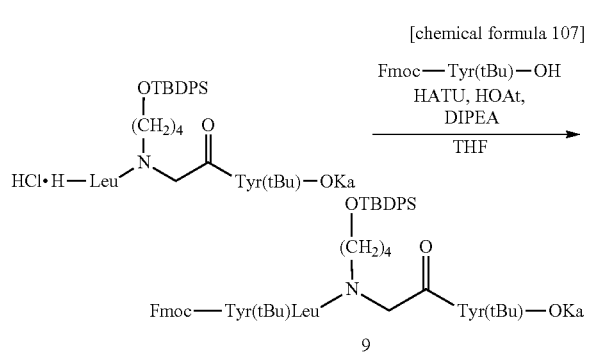

The de-Fmoc form (8.31 g) was dissolved in THF (93 mL), and Fmoc-Tyr(tBu)-OH (3.21 g, 6.99 mmol, 1.5 equiv), HOAt (1.59 g, 11.7 mmol, 2.5 equiv), HATU (4.42 g, 11.6 mmol, 2.5 equiv) and DIPEA (4860 μL, 27.9 mmol, 6.0 equiv) were added and the mixture was stirred at room temperature for 40 minutes. The same post treatment as in synthesis of the compound 6 was conducted, to obtain a compound 9 (9.05 g, 94.7%).

Synthesis of Compound 10

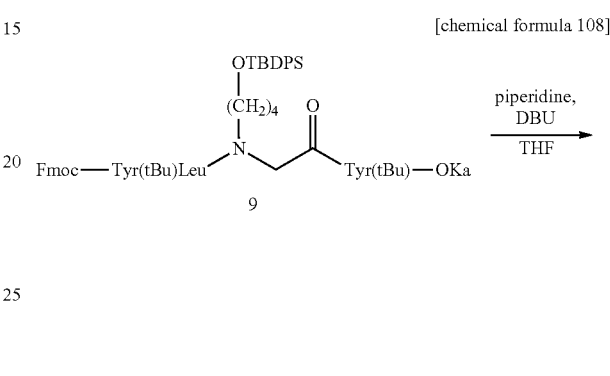

The compound 9 (4.17 g, 2.03 mmol) was dissolved in THF (41 mL), and piperidine (389 μL, 3.65 mmol, 1.8 equiv) and DBU (395 μL, 2.63 mmol, 1.3 equiv) were added and the mixture was stirred at room temperature for 5 minutes. The same post treatment as in synthesis of the compound 2 was conducted, to obtain a de-Fmoc form (3.92 g).

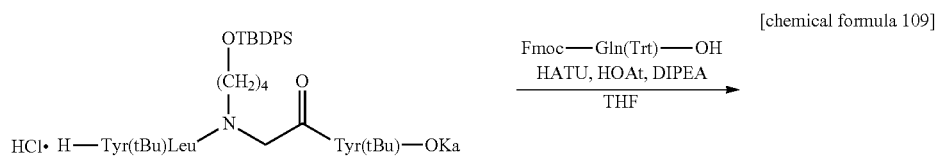

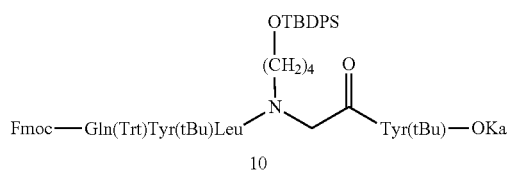

The de-Fmoc form (3.92 g) was dissolved in THF (41 mL), and Fmoc-Gln(Trt)-OH (1.86 g, 3.04 mmol, 1.5 equiv), HATU (1.93 g, 5.07 mmol, 2.5 equiv), HOAt (691 mg, 5.07 mmol, 2.5 equiv) and DIPEA (2120 μL, 12.2 mmol, 6.0 equiv) were added and the mixture was stirred at room temperature for 30 minutes. The same post treatment as in synthesis of the compound 4 was conducted, to obtain a compound 10 (4.83 g, 98.0%).

Synthesis of Compound 11

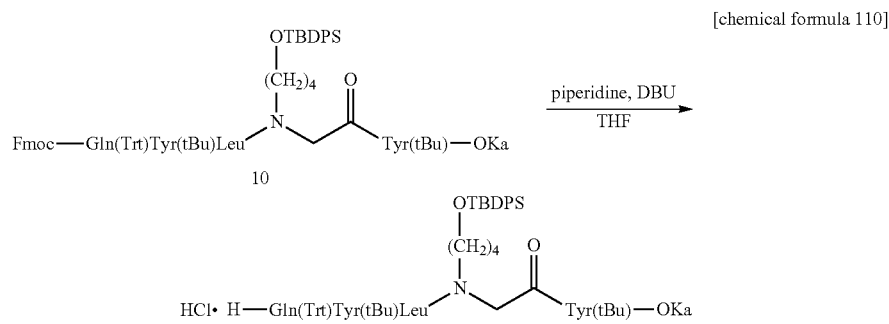

[chemical formula 110]

The compound 10 (4.83 g, 1.99 mmol) was dissolved in THF (40 mL), and piperidine (382 μL, 3.59 mmol, 1.8 equiv) and DBU (388 μL, 2.59 mmol, 1.3 equiv) were added and the mixture was stirred at room temperature for 5 minutes. The same post treatment as in synthesis of the compound 2 was conducted, to obtain a de-Fmoc form (4.63 g).

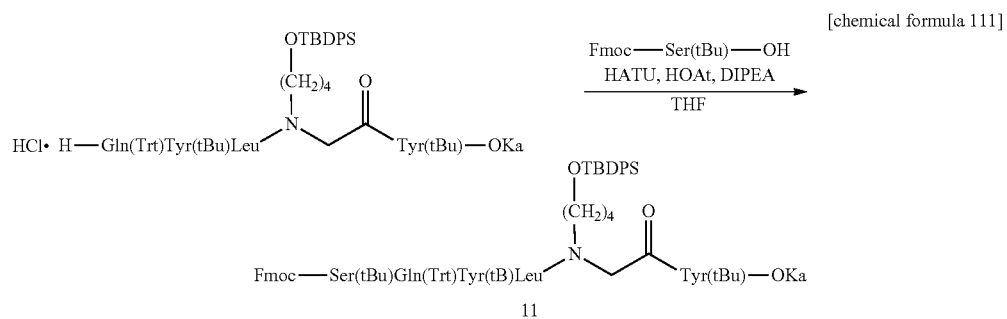

[chemical formula 111]

The de-Fmoc form (4.63 g) was dissolved in THF (40 mL), and Fmoc-Ser(tBu)-OH (1.15 g, 2.99 mmol, 1.5 equiv), HATU (1.89 g, 4.98 mmol, 2.5 equiv), HOAt (676 mg, 4.98 mmol, 2.5 equiv) and DIPEA (2082 μL, 11.9 mmol, 6.0 equiv) were added and the mixture was stirred at room temperature for 45 minutes. The same post treatment as in synthesis of the compound 4 was conducted, to obtain a compound 11 (5.49 g).

Synthesis of Compound 12

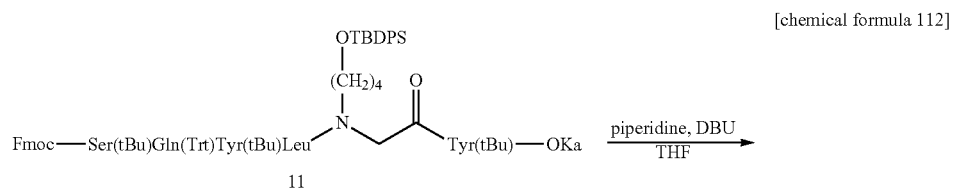

[chemical formula 112]

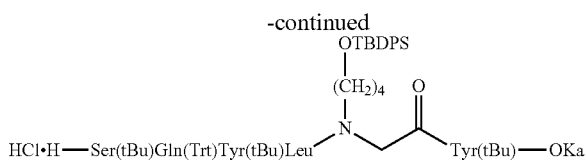

The compound 11 (5.49 g) was dissolved in THF (40 mL), and piperidine (382 μL, 3.59 mmol, 1.8 equiv) and DBU (388 μL, 2.59 mmol, 1.3 equiv) were added and the mixture was stirred at room temperature for 5 minutes. The same post treatment as in synthesis of the compound 2 was conducted, to obtain a de-Fmoc form (4.65 g, 98.0% from compound 10).

[chemical formula 113]

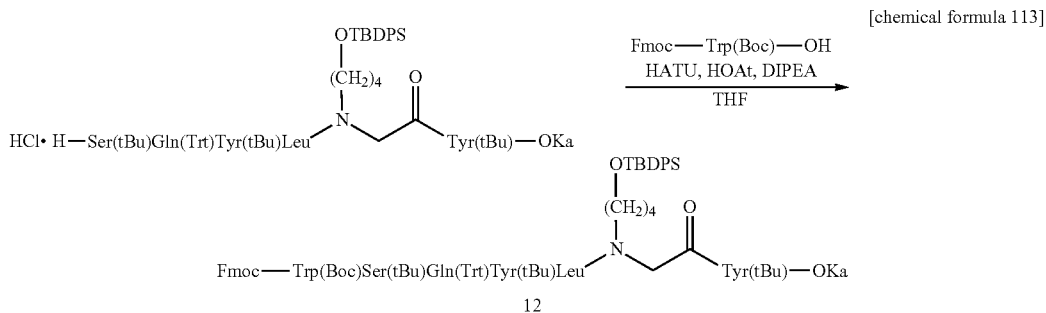

The de-Fmoc form (4.65 g, 1.95 mmol) was dissolved in THF (39 mL), and Fmoc-Trp(Boc)-OH (1.54 g, 2.92 mmol, 1.5 equiv), HOAt (398 mg, 2.92 mmol, 1.5 equiv), HATU (1.11 g, 2.92 mmol, 1.5 equiv) and DIPEA (1698 μL, 9.75 mmol, 5.0 equiv) were added and the mixture was stirred at room temperature for 70 minutes. The same post treatment as in synthesis of the compound 4 was conducted, to obtain a compound 12 (5.32 g, 95.4%).

Synthesis of Compound 13

[chemical formula 114]

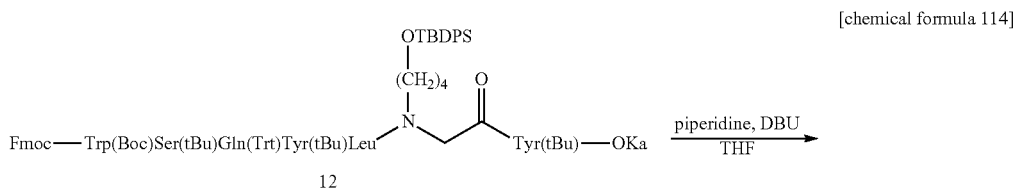

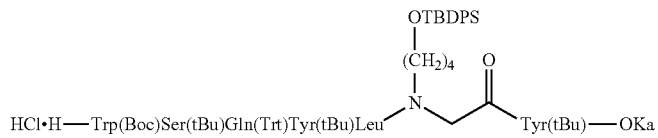

The compound 12 (5.32 g, 1.86 mmol) was dissolved in THF (37.2 mL), and piperidine (372 μL, 3.50 mmol, 1.9 equiv) and DBU (372 μL, 2.49 mmol, 1.3 equiv) were added and the mixture was stirred at room temperature for 5 minutes. The same post treatment as in synthesis of the compound 2 was conducted, to obtain a de-Fmoc form (4.96 g).

Fmoc-Tyr(tBu)-OH (15.2 g, 33.0 mmol, 1.5 equiv), DIPCI (6856 μL, 44.0 mmol, 2.0 equiv) and DMAP (26.9 mg, 0.220 mmol, 0.01 equiv) were added and the mixture was stirred at room temperature for 35 minutes. The same post treatment as in synthesis of the compound 1 was conducted, to obtain a compound 28 (29.9 g, q. y.).

[chemical formula 115]

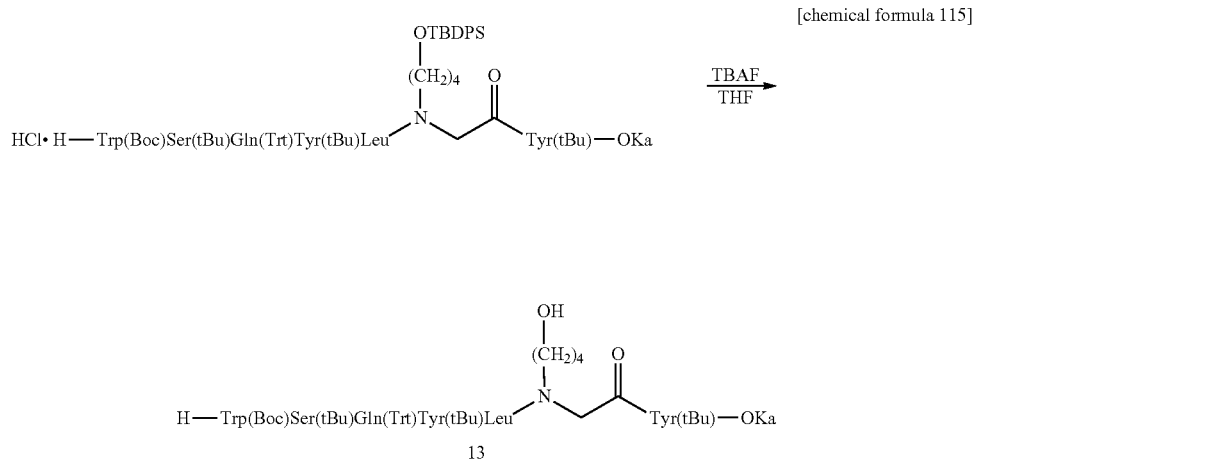

The de-Fmoc form (4.96 g) was dissolved in THF (12.6 mL), and TBAF (1.0 M solution in THF, 6.0 mL, 6.00 mmol, 3.2 equiv) was added and the mixture was stirred at room temperature for 19 hours. The solvent was evaporated under reduced pressure, then, to the residue was added $CH_2Cl_2$ and the mixture was washed with 1 N HCl, water and saturated saline, the organic layer was dried over anhydrous $MgSO_4$, filtrated, then, the filtrate was evaporated under reduced pressure. The residue was subjected to silica gel column chromatography ($CH_2Cl_2$/THF, 100:0-75:25), to obtain a compound 13 (2.02 g, 45.3%).

The compound 13 is a component in which [C] is Trp-Ser-Gln-Tyr-Leu and [D] is Tyr.

Synthesis of Compound 29

[chemical formula 117]

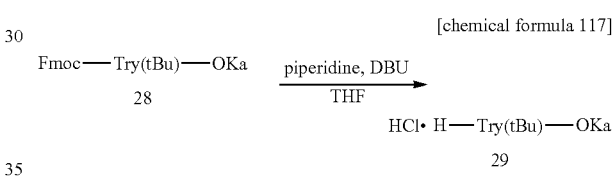

The compound 28 (9.58 g, 7.07 mmol) was dissolved in THF (141 mL), and piperidine (1260 μL, 12.7 mmol, 1.8 equiv) and DBU (1374 μL, 9.19 mmol, 1.3 equiv) were added and the mixture was stirred at room temperature for 5 minutes. After confirmation of disappearance of raw materials by TLC, the same post treatment as described above (synthesis of compound 2) was conducted, to obtain a compound 29 (8.28 g, q. y.).

Example 2

Synthesis of Intermediate (Compound 38)

Synthesis of First Component

The compound 38 as a first component (X side component) was synthesized by the following step.

Synthesis of Compound 30

[chemical formula 116]

Fmoc—Try(tBu)—OH + KaOH $\xrightarrow{\text{DIPCI, DMAP}}{CH_2Cl_2}$ Fmoc—Try(tBu)—OKa
28

[chemical formula 118]

Fmoc—Lys(Mtt)—OH + KaOH $\xrightarrow{\text{DIPCI, DMAP}}{CH_2Cl_2}$ Fmoc—Lys(Mtt)—OKa
30

3,4,5-trioctadecyloxybenzyl alcohol (denoted as "KaOH") (20.1 g, 22.0 mmol) was dissolved in $CH_2Cl_2$ (220 mL), and 3,4,5-trioctadecyloxybenzyl alcohol (hereinafter, denoted as "KaOH") (3.00 g, 3.28 mmol) was dissolved in $CH_2Cl_2$ (32.8 mL), and Fmoc-Lys(Mtt)-OH (3.08 g, 4.93 mmol, 1.5 equiv), DIPCI (1023 μL, 6.57 mmol, 2.0 equiv) and DMAP (4.0 mg, 0.0328 mmol, 0.01 equiv) were added and the mixture was stirred at room temperature for 42 minutes. The same post treatment as in synthesis of the compound 1 was conducted, to obtain a compound 30 (5.32 g).

Synthesis of Compound 31

[chemical formula 119]

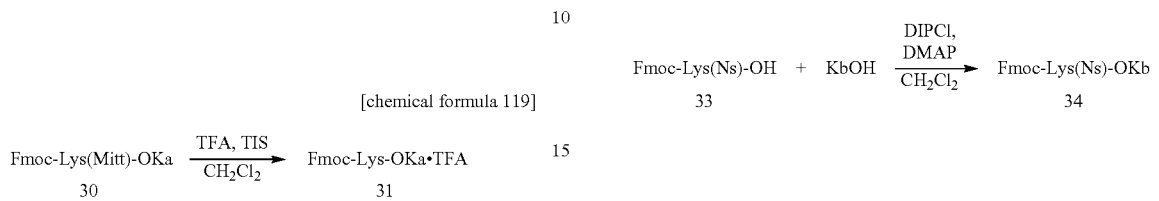

The compound 30 (5.32 g) was dissolved in $CH_2Cl_2$ (32.8 mL), and TIS (3284 μL) and TFA (985.2 μL) were added and the mixture was stirred at room temperature for 12 minutes. TIS (3284 μl) was additionally added and the mixture was further stirred for 53 minutes. TFA (985.2 μL) was additionally added and the mixture was further stirred for 16 minutes. The same post treatment as in synthesis of the compound 4 was conducted, to obtain a compound 31 (4.48 g).

Synthesis of Compound 32

[chemical formula 120]

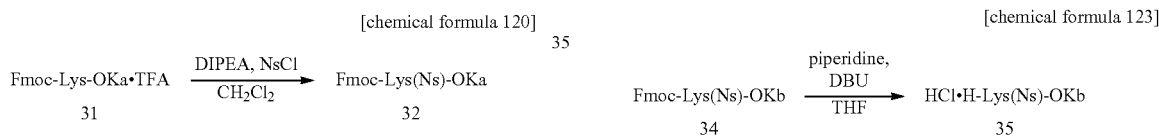

The compound 31 (4.48 g) was dissolved in $CH_2Cl_2$ (65.7 mL), and DIPEA (1258 μL, 7.22 mmol, 2.2 equiv) and NsCl (873 mg, 3.94 mmol, 1.2 equiv) were added and the mixture was stirred at room temperature for 37 minutes. The same post treatment as in synthesis of the compound 3 was conducted, to obtain a compound 32 (4.75 g, q. y.).

Synthesis of Compound 33

[chemical formula 121]

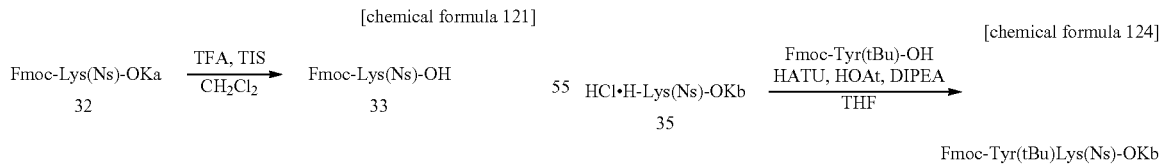

The compound 32 (4.38 g, 3.02 mmol) was dissolved in $CH_2Cl_2$ (27 mL), and TIS (6.0 mL) and TFA (27 mL) were added and the mixture was stirred at room temperature for 2 hours. The solvent was evaporated under reduced pressure, to the residue was added $CH_2Cl_2$ to give a diluted solution, which was then washed with water three times and saturated saline, and the organic layer was dried over anhydrous $MgSO_4$, filtrated and the filtrate was evaporated under reduced pressure. The residue was subjected to silica gel column chromatography ($CH_2Cl_2$/MeOH, 100:0-85:15), to obtain a compound 33 (1.42 g, 84.8%).

Synthesis of Compound 34

[chemical formula 122]

$$\text{Fmoc-Lys(Ns)-OH} + \text{KbOH} \xrightarrow[CH_2Cl_2]{\text{DIPCl,} \atop \text{DMAP}} \text{Fmoc-Lys(Ns)-OKb}$$
$$\phantom{aaaaaaaaa}33\phantom{aaaaaaaaaaaaaaaaaaaaaaaaaa}34$$

2,4-didocosoxy benzyl alcohol (hereinafter, denoted as "KbOH") (2.09 g, 2.76 mmol) was dissolved in $CH_2Cl_2$ (27.6 mL), and the compound 33 (2.29 g, 4.14 mmol, 1.5 equiv), DIPCI (859 μL, 5.51 mmol, 2.0 equiv) and DMAP (3.4 mg, 0.0278 mmol, 0.01 equiv) were added and the mixture was stirred at room temperature for 45 minutes. The same post treatment as for the compound 1 was conducted, to obtain a compound 34 (4.13 g, q. y.).

Synthesis of Compound 35

[chemical formula 123]

$$\text{Fmoc-Lys(Ns)-OKb} \xrightarrow[THF]{\text{piperidine,} \atop \text{DBU}} \text{HCl·H-Lys(Ns)-OKb}$$
$$\phantom{aaaaaa}34\phantom{aaaaaaaaaaaaaaaaaaaaaaaa}35$$

The compound 34 (4.13) was dissolved in THF (55.1 mL), and piperidine (491 μL) and DBU (536 μL) were added and the mixture was stirred at room temperature for 5 minutes. After confirmation of disappearance of starting materials by TLC, the same post treatment as in synthesis of the compound 2 was conducted, to obtain a compound 35 (3.00 g, 98.2%).

Synthesis of Compound 36

[chemical formula 124]

$$\text{HCl·H-Lys(Ns)-OKb} \xrightarrow[THF]{\text{Fmoc-Tyr(tBu)-OH} \atop \text{HATU, HOAt, DIPEA}}$$
$$\phantom{aaaaaa}35$$
$$\phantom{aaaaaaaaaaaaaaaaaa}\text{Fmoc-Tyr(tBu)Lys(Ns)-OKb}$$
$$\phantom{aaaaaaaaaaaaaaaaaaaaaaaaaa}36$$

The compound 35 (332 mg, 0.300 mmol) was dissolved in THF (6 mL), and Fmoc-Tyr(tBu)-OH (207 mg, 0.450 mmol, 1.5 equiv), HOAt (61.3 mg, 0.450 mmol, 1.5 equiv), HATU (171 mg, 0.450 mmol, 1.5 equiv) and DIPEA (261 μL, 1.50 mmol, 5.0 equiv) were added and the mixture was stirred at room temperature for 53 minutes. The same post treatment as in synthesis of the compound 4 was conducted, to obtain a compound 36 (441 mg, 97.3%).

Synthesis of Compound 37

[chemical formula 125]

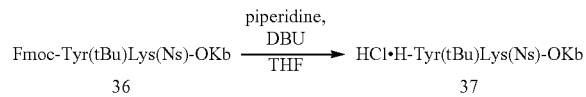

The compound 36 (2.73 g, 1.81 mmol) was dissolved in THF (36.1 mL), and piperidine (322 μL) and DBU (351 μL) were added and the mixture was stirred at room temperature for 5 minutes. After confirmation of disappearance of starting materials by TLC, the same post treatment as in synthesis of the compound 2 was conducted, to obtain a compound 37 (2.25 g, 94.1%).

Synthesis of Compound 38

[chemical formula 126]

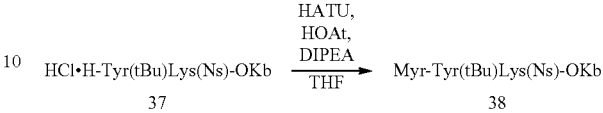

The compound 37 (266 mg, 0.201 mmol) was dissolved in THF (4 mL), and myristic acid (68.9 mg, 0.302 mmol, 1.5 equiv), HOAt (41.4 mg, 0.304 mmol, 1.5 equiv), HATU (114 mg, 0.301 mmol, 1.5 equiv) and DIPEA (174 μL, 0.999 mmol, 5.0 equiv) were added and the mixture was stirred at room temperature for 1 hour and 50 minutes. The same post treatment as in synthesis of the compound 4 was conducted, to obtain a compound 38 (289 mg, 95.5%).

The compound 38 is a component in which [A] is Tyr and [B] is a single bond.

Synthesis of Intermediate

Synthesis of Compound 14

[chemical formula 127]

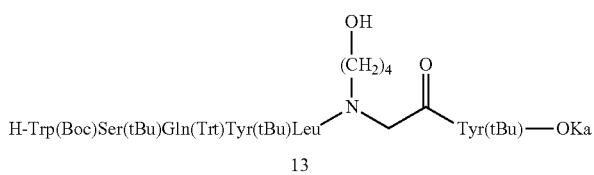

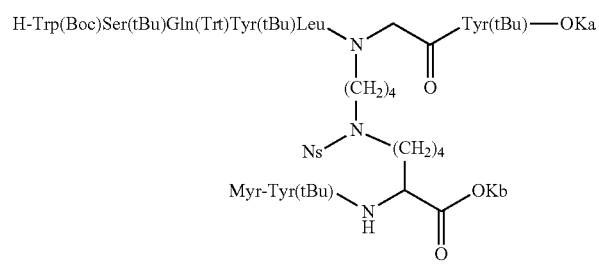

The compound 13 (265 mg, 0.111 mmol), the compound 38 (289 mg, 0.192 mmol, 1.7 equiv) and PPh$_3$ (118 mg, 0.450 mmol, 4.1 equiv) were dissolved in THF (11 mL), and DEAD (201 μL, 0.443 mmol, 4.0 equiv) was added and the mixture was stirred at room temperature for 61 minutes. PPh$_3$ (121 mg, 0.461 mmol, 4.2 equiv) and DEAD (201 μL, 0.443 mmol, 4.0 equiv) were added and the mixture was stirred for 59 minutes. The same post treatment as in synthesis of the compound 4 was conducted to obtain a residue, which was then subjected to silica gel column chromatography (CH$_2$CH$_2$/THF, 100:0-88:12), to obtain a Mitsunobu reaction product (132 mg, 30.6%).

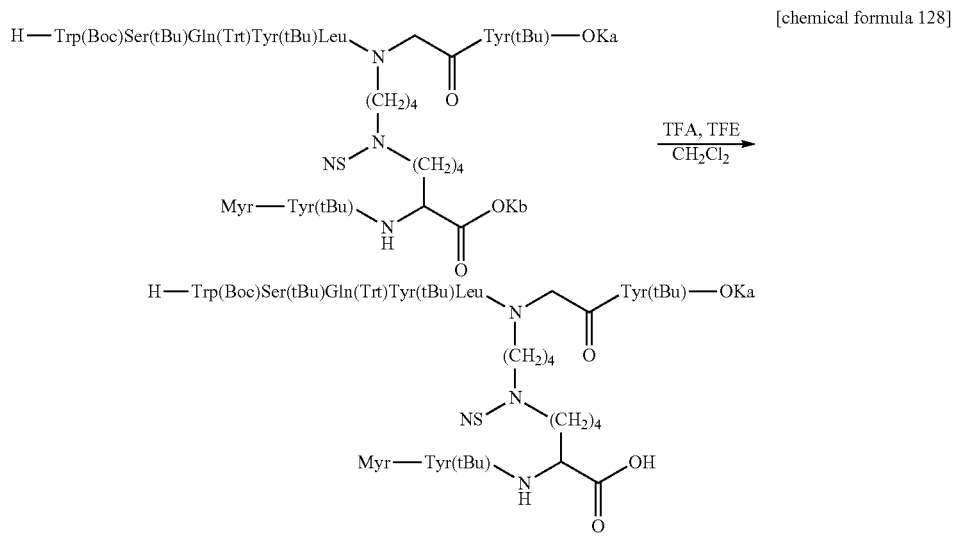

[chemical formula 128]

The Mitsunobu reaction product (132 mg, 0.0340 mmol) was dissolved in CH$_2$Cl$_2$ (3.4 mL), and TFE (340 μL) and TFA (34.0 μL) were added and the mixture was stirred at room temperature for 70 minutes. The precipitated material was filtrated through Celite, and the solvent was evaporated under reduced pressure. The same post treatment as in synthesis of the compound 4 was conducted to obtain a residue, which was then subjected to silica gel column chromatography (CHCl$_3$/MeOH, 100:0-95:5), to obtain a compound 14 (75.1 mg, 70.3%) as an intermediate of the present invention.

Example 3

Synthesis of Cross-Linked Peptide (Bdev-7)

Synthesis of Compound 15

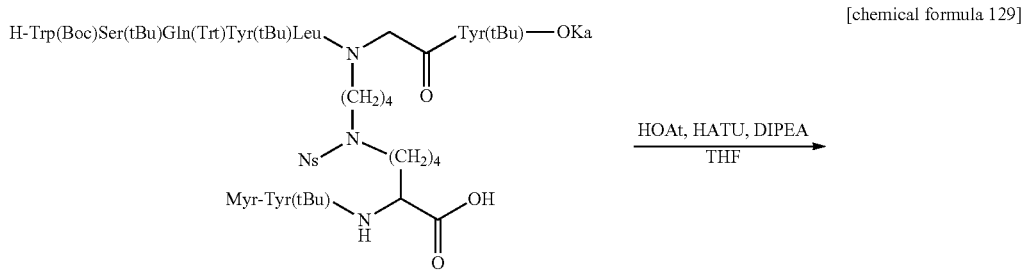

[chemical formula 129]

-continued
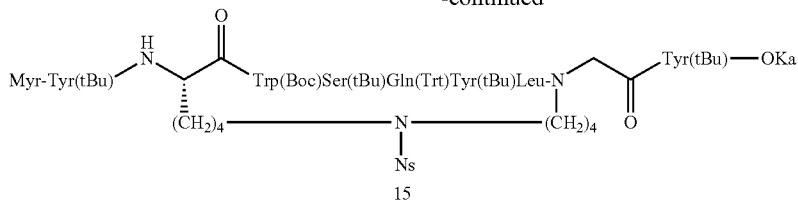
The compound 14 (75.1 mg, 0.0239 mmol), HOAt (4.2 mg, 0.0309 mmol, 1.3 equiv) and HATU (11.2 mg, 0.0295 mmol, 1.2 equiv) were dissolved in THF (4780 μL), and DIPEA (20.8 μL, 0.119 mmol, 5.0 equiv) was added and the mixture was stirred at room temperature for 17 hours and 40 minutes.
The same post treatment as in synthesis of the compound 4 was conducted, to obtain a compound 15 (64.5 mg, 86.6%).
Synthesis of Compound 16
[chemical formula 130]
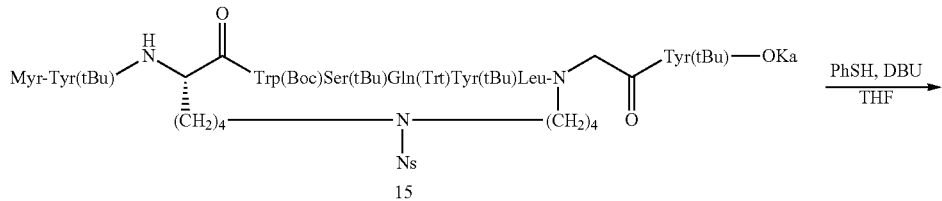
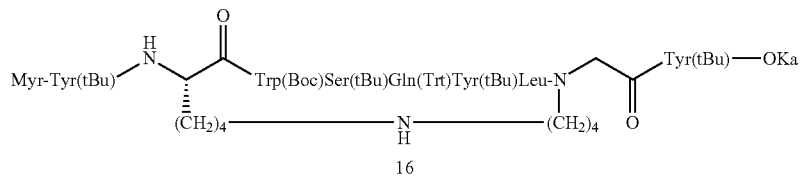

The compound 15 (64.5 mg, 0.0207 mmol) was dissolved in THF (414 μL), and PhSH (6.38 μL, 0.0621 mmol, 3.0 equiv) and DBU (9.29 μL, 0.0621 mmol, 3.0 equiv) were added and the mixture was stirred at room temperature for 1 hour and 38 minutes. PhSH (6.38 μL, 0.0621 mmol, 3.0 equiv) and DBU (9.29 μL, 0.0621 mmol, 3.0 equiv) were added and the mixture was stirred at room temperature for 3 hours and 29 minutes. To the reaction solution was added concentrated hydrochloric acid (10 μL) and the solvent was evaporated under reduced pressure. The same post treatment as in synthesis of the compound 4 was conducted, to obtain a compound 16 (55.6 mg, 91.3%).

Synthesis of Cross-Linked Peptide (Bdev-7)

[chemical formula 131]

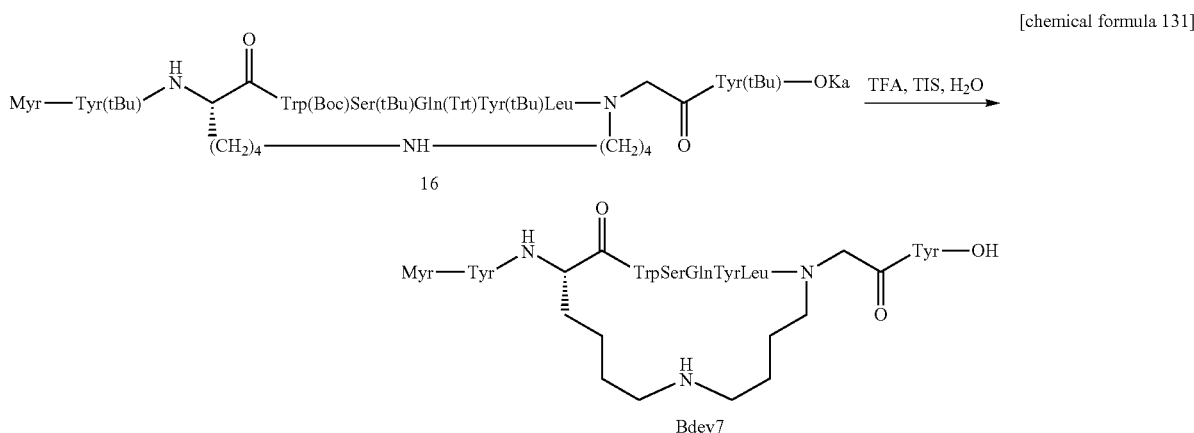

To the compound 16 (21.8 mg, 0.0743 mmol) was added a solution (743 μL) of TFA/TIS/H$_2$O=95:5:5 and the mixture was stirred at room temperature for 3 hours. The precipitated material was filtrated, and the filtrate was evaporated under reduced pressure. To the residue was added IPE to find deposition of a precipitated material, which was centrifugally separated to give a residue, and the residue was purified by HPLC, to obtain a cross-linked peptide of the present invention (Bdev-7) (2.8 mg, 2.6%). HRMS m/z [M+H]$^+$: calcd for C$_{78}$H$_{111}$N$_{12}$O$_{16}$: 1471.8241. found 1472.1734.

Cross-linked peptides as other W9 peptide mimics having the following peptide sequence structures were synthesized. The structure patterns and Z$_1$ to Z$_3$ substitution patterns of the compounds synthesized are as described in Table 2 below.

[chemical formula 132]

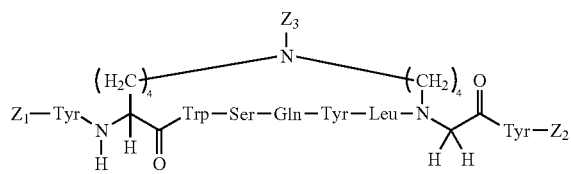
(P-1)

[chemical formula 133]

(P-2)

[chemical formula 134]

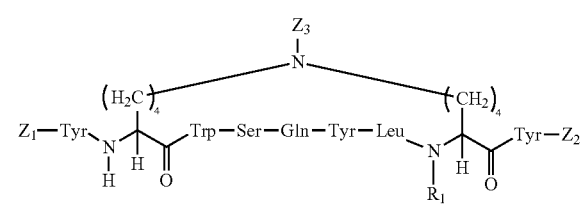
(P-3)

-continued

[chemical formula 135]

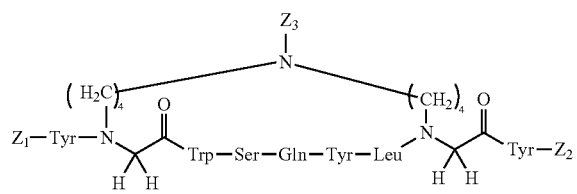

(P-4)

TABLE 2

| compound number | structure pattern | substitution pattern | | |
|---|---|---|---|---|
| | | $Z_1$ | $Z_3$ | $Z_2$ |
| Bdev-2 | P-1 | H | Ac | OH |
| Bdev-3 | P-1 | Ac | $PEG_{2000}$ | OH |
| Bdev-4 | P-1 | H | Myr | OH |
| Bdev-5 | P-1 | Ac | Ac | OH |
| Bdev-6 | P-1 | Ac | H | OH |
| Bdev-7*[1] | P-1 | Myr | H | OH |
| Bdev-8 | P-1 | H | H | OH |
| Bdev-10 | P-1 | $PEG_{2000}$ | Ac | OH |
| Bdev-12 | P-1 | Ac | Myr | OH |
| Bdev-13 | P-1 | Ac | Ac | $NH-PEG_{2000}$ |
| Bdev-14 | P-1 | H | $PEG_{2000}$ | OH |
| Bdev-19 | P-2 | H | Ac | OH |
| Bdev-20 | P-2 | H | $PEG_{2000}$ | OH |
| Bdev-21 | P-3 | H | Ac | OH |
| Bdev-25 | P-4 | H | Ac | OH |
| Bdev-27 | P-1 | H | EtC(O) | OH |
| Bdev-28 | P-1 | H | n-BuC(O) | OH |
| Bdev-29 | P-1 | H | mPEG3 | OH |
| Bdev-30 | P-1 | H | mPEG7 | OH |

*[1] compound synthesized in Example 2

Example 4

Synthesis of Intermediate (Compound 19) for Synthesis of Bdev-3, -5, -6, -12 and -13

Synthesis of an intermediate for synthesis of Bdev-3, -5, -6, -12 and -13 was carried out as described below.

Synthesis of Compound 39

[chemical formula 136]

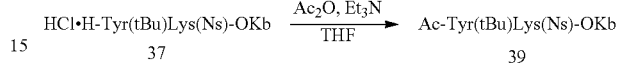

The compound 37 (746 mg, 0.562 mmol) was dissolved in $CH_2Cl_2$ (11 mL), and $Et_3N$ (160 μL, 1.14 mmol, 2.0 equiv) and $Ac_2O$ (100 μL, 1.06 mmol, 1.9 equiv) were added and the mixture was stirred at room temperature for 52 minutes. The same post treatment as described above (synthesis of compound 3) was conducted, to obtain a compound 39 (698 mg, 0.524 mmol, 93.2%).

Synthesis of Compound 40

[chemical formula 137]

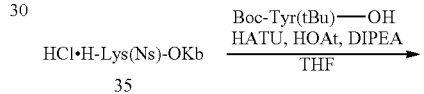

The compound 35 (775 mg, 0.700 mmol) was dissolved in THF (14 mL), and Boc-Tyr(tBu)-OH (354 mg, 1.05 mmol, 1.5 equiv), HOAt (143 mg, 1.05 mmol, 1.5 equiv), HATU (399 mg, 1.05 mmol, 1.5 equiv) and DIPEA (610 μL, 3.50 mmol, 5.0 equiv) were added and the mixture was stirred at room temperature for 42 minutes. The same post treatment as in synthesis of the compound 4 was conducted, to obtain a compound 40 (935 mg, 96.1%).

Synthesis of Compound 17

[chemical formula 138]

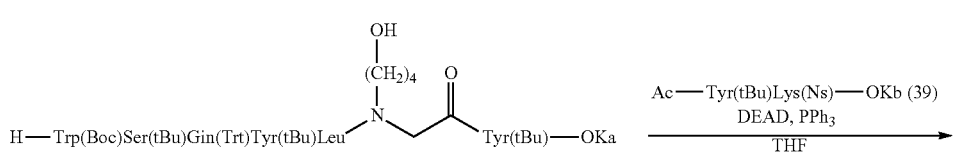

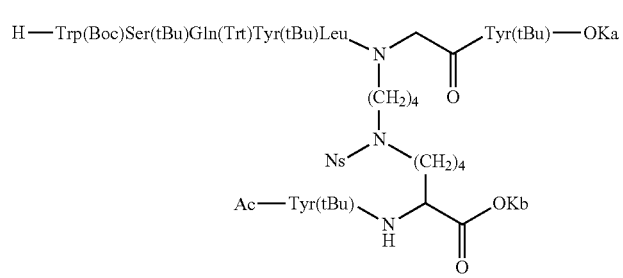

The compound 13 (944 mg, 0.394 mmol), the compound 39 (635 mg, 0.477 mmol, 1.2 equiv) and PPh₃ (211 mg, 0.804 mmol, 2.0 equiv) were dissolved in THF (40 mL), and DEAD (357 μL, 0.787 mmol, 2.0 equiv) was added and the mixture was stirred at room temperature for 3 hours and 7 minutes. PPh₃ (208 mg, 0.793 mmol, 2.0 equiv) was added and the mixture was stirred for 33 minutes. DEAD (357 μL, 0.787 mmol, 2.0 equiv) was added and the mixture was stirred or 1 hour and 50 minutes. The same post treatment as in synthesis of the compound 4 was conducted to obtain a residue (1.573 g), which was used in the subsequent reaction.

[chemical formula 139]

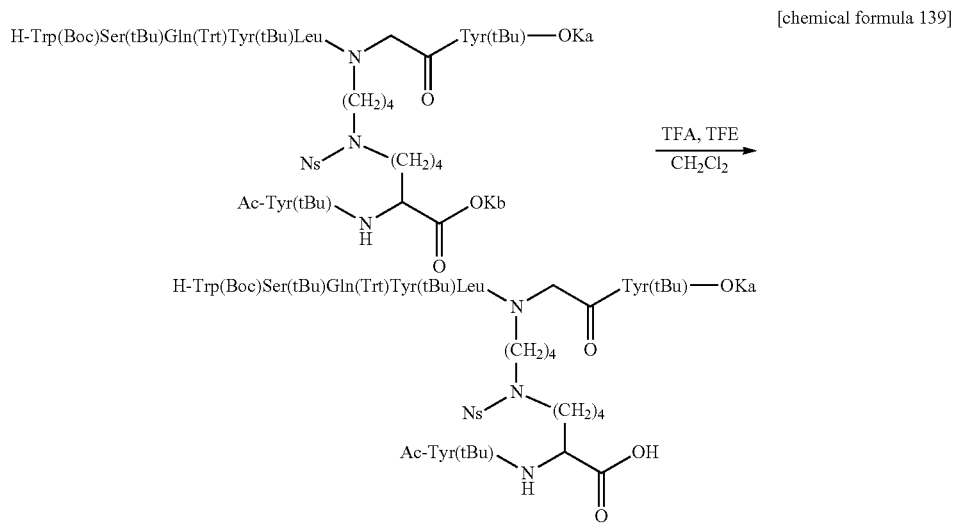

The residue (1.573 g) was dissolved in CH₂Cl₂ (47.7 mL), and TFE (4770 μL) and TFA (477 μL) were added and the mixture was stirred at room temperature for 1 hour. The precipitated material was filtrated through Celite, and to the filtrate was added DIPEA (1050 μL), then, the solvent was evaporated under reduced pressure. The same post treatment as in synthesis of the compound 4 was conducted to obtain a residue, which was then subjected to silica gel column chromatography (CHCl₃/MeOH, 100:0-90:10 and CHCl₃/EtOH, 100:0-93:7), to obtain a compound 17 (651 mg, 55.7%) as an intermediate of the present invention.

Synthesis of Compound 18

[chemical formula 140]

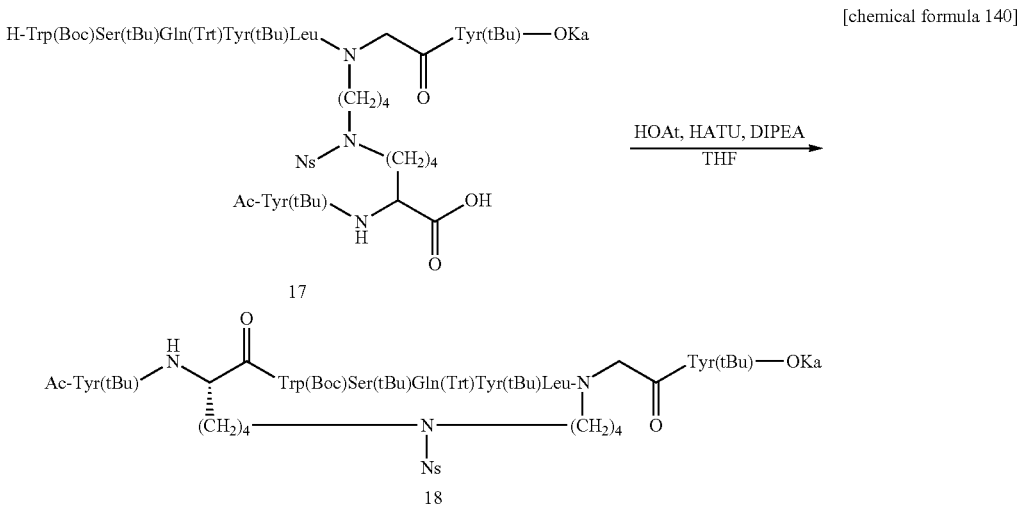

The compound 17 (485 mg, 0.163 mmol), HOAt (26.8 mg, 0.197 mmol, 1.2 equiv) and HATU (74.8 mg, 0.197 mmol, 1.2 equiv) were dissolved in THF (32.6 mL), and DIPEA (142 μL, 0.815 mmol, 5.0 equiv) was added and the mixture was stirred at room temperature for 3 hours and 30 minutes. The same post treatment as in synthesis of the compound 4 was conducted, to obtain a compound 18 (462 mg, 96.3%).

Synthesis of Compound 19

[chemical formula 141]

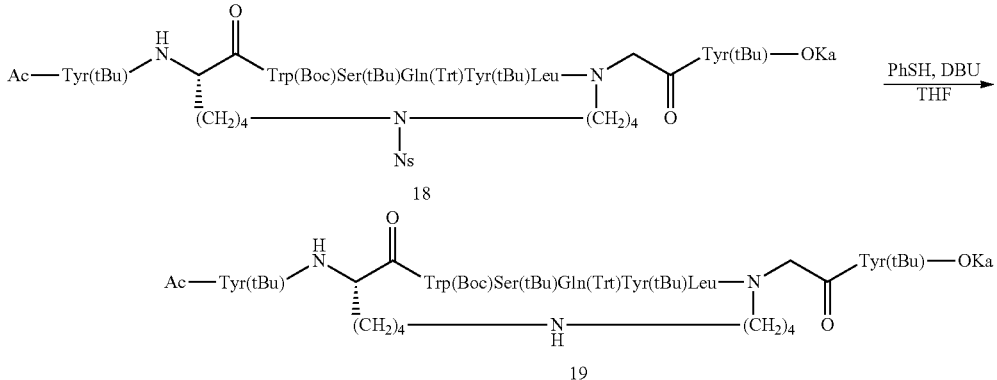

The compound 40 (462 mg, 0.157 mmol) was dissolved in THF (1560 μL), and PhSH (16.0 μL, 0.156 mmol, 1.0 equiv) and DBU (70.0 μL, 0.468 mmol, 3.0 equiv) were added and the mixture was stirred at room temperature for 50 minutes. PhSH (32.0 μL, 0.312 mmol, 2.0 equiv) was added and the mixture was stirred for 1 hour and 11 minutes. PhSH (48.0 μL, 0.467 mmol, 3.0 equiv) and DBU (70.0 μL, 0.468 mmol, 3.0 equiv) were added and the mixture was stirred at room temperature for 50 minutes. To the reaction solution was added concentrated hydrochloric acid (78.0 μL) and the solvent was evaporated under reduced pressure. The same post treatment as in synthesis of the compound 16 was conducted, to obtain a compound 19 (416 mg, 96.2%).

Example 5

Synthesis of Bdev-3, -5, -6, -12 and -13

(1) Synthesis of Bdev-6

Bdev-6 was synthesized as described below.

[chemical formula 142]

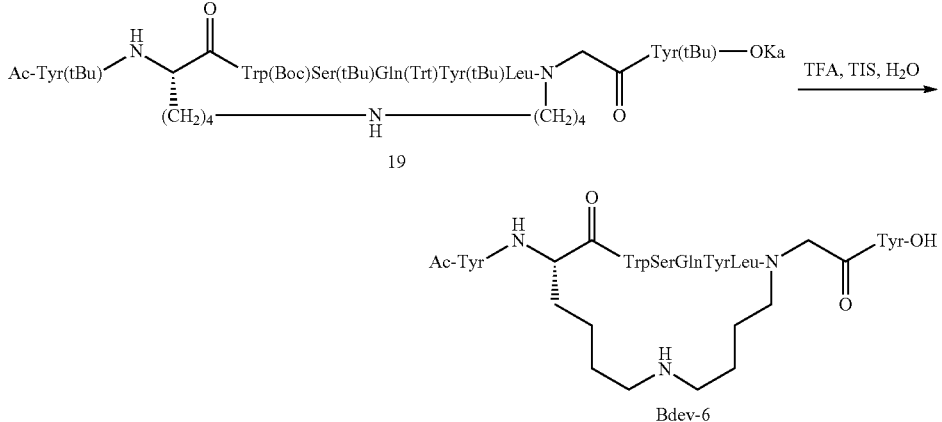

To the compound 19 (48.2 mg, 0.0174 mmol) was added a solution (1740 μL) of TFA/TIS/H$_2$O=95:5:5 and the mixture was stirred at room temperature for 3 hours. The same post treatment and HPLC purification as in synthesis of Bdev-7 were conducted, to obtain Bdev-6 (5.3 mg, 23.4%). HRMS m/z [M+H]$^+$: calcd for C$_{66}$H$_{87}$N$_{12}$O$_{16}$: 1303.6363. found 1303.9331.

(2) Synthesis of Bdev-12

Bdev-12 was synthesized as described below.

Synthesis of Compound 20

[chemical formula 143]

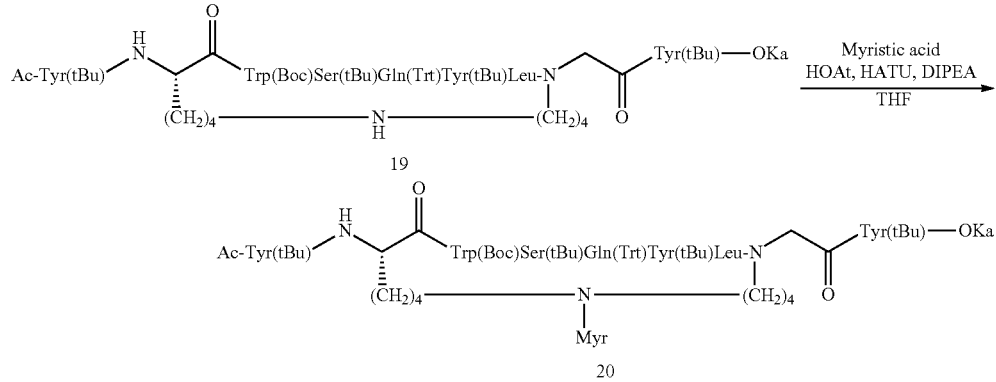

The compound 19 (149 mg, 0.0540 mmol), myristic acid (18.7 mg, 0.0819 mmol, 1.5 equiv), HOAt (11.1 mg, 0.0816 mmol, 1.5 equiv) and HATU (31.0 mg, 0.0815 mmol, 1.5 equiv) were dissolved in THF (1080 μL), and DIPEA (47.0 μL, 0.270 mmol, 5.0 equiv) was added and the mixture was stirred at room temperature for 3 hours. The same post treatment as in synthesis of the compound 4 was conducted, to obtain a compound 20 (147 mg, 91.5%).

Synthesis of Bdev-12

[chemical formula 144]

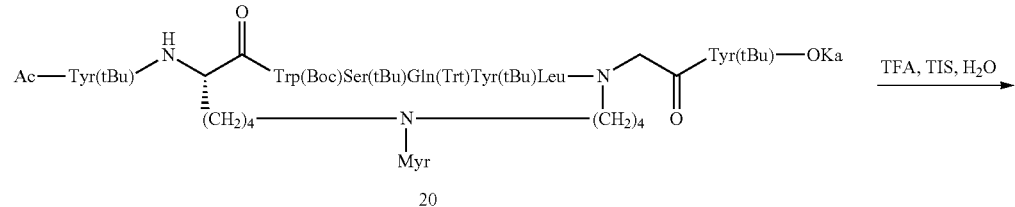

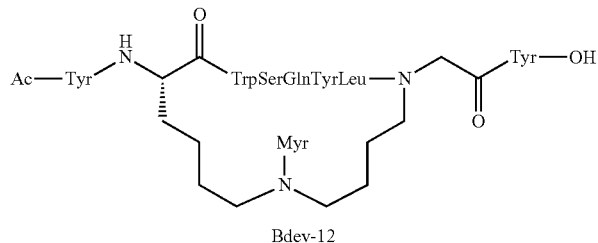

To the compound 20 (147 mg, 0.0494 mmol) was added a solution (5 mL) of TFA/TIS/H$_2$O=95:5:5 and the mixture was stirred at room temperature for 3 hours. The same post treatment and HPLC purification as in synthesis of Bdev-7 were conducted, to obtain Bdev-12 (28.0 mg, 37.4%). HRMS m/z [M+H]$^+$: calcd for C$_{80}$H$_{113}$N$_{12}$O$_{17}$: 1513.8347. found 1514.2531.

(3) Synthesis of Bdev-3

Bdev-3 was synthesized as described below.

Synthesis of Compound 21

[chemical formula 145]

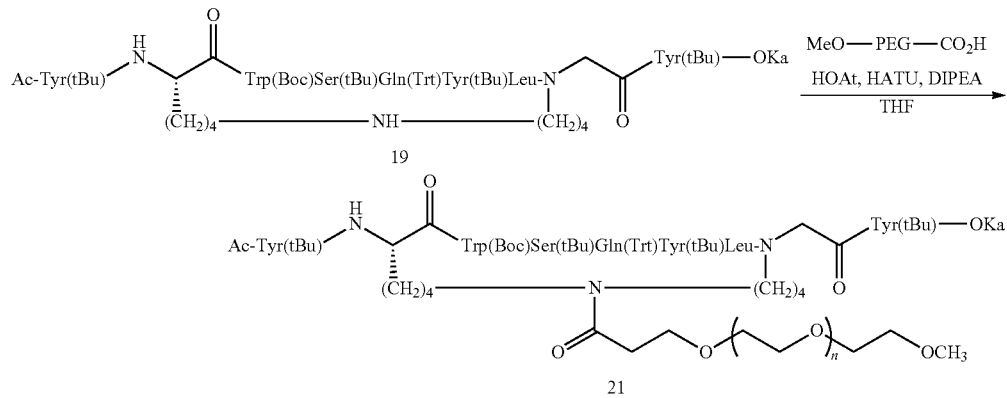

The compound 19 (111 mg, 0.0400 mmol), MeO-PEG-CO$_2$H (121 mg, 0.0600 mmol, 1.5 equiv), HOAt (6.5 mg, 0.0480 mmol, 1.2 equiv) and HATU (18.3 mg, 0.0480 mmol, 1.2 equiv) were dissolved in THF (2 mL), and DIPEA (34.8 µL, 0.200 mmol, 5.0 equiv) was added and the mixture was stirred at room temperature for 53 minutes. DIPEA (34.8 µL, 0.200 mmol, 5.0 equiv) was added and the mixture was stirred for 56 minutes. MeO-PEG-CO$_2$H (121 mg, 0.0600 mmol, 1.5 equiv), HATU (22.8 mg, 0.0600 mmol, 1.5 equiv) and DIPEA (17.4 mL, 0.0999 mmol, 2.5 equiv) were added and the mixture was stirred for 2 hours and 9 minutes. The solvent was evaporated under reduced pressure, and the residue was subjected to silica gel column chromatography (CH$_2$Cl$_2$/MeOH, 100:0-90:10), to obtain a compound 21 (313 mg) as a crude product.

Synthesis of Bdev-3

[chemical formula 146]

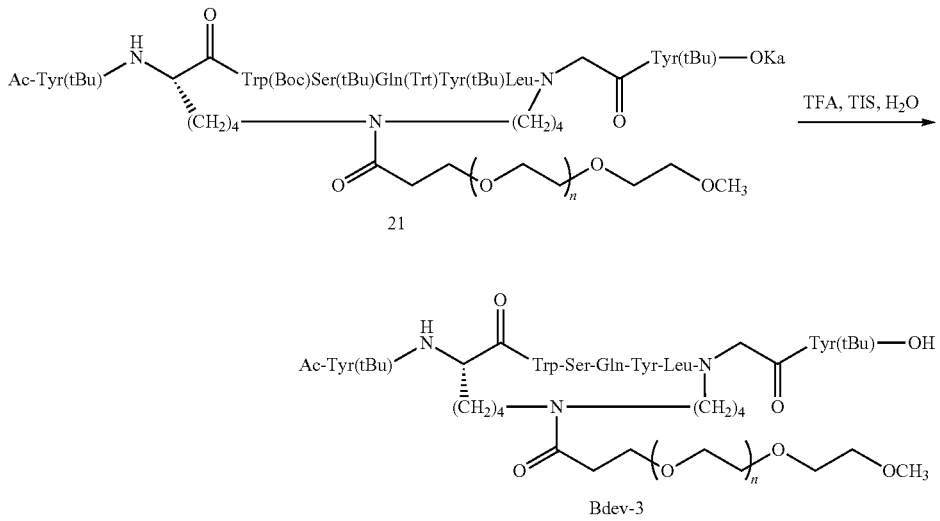

To the compound 21 (147 mg, 0.0494 mmol) was added a solution (5 mL) of TFA/TIS/H$_2$O=95:5:5 and the mixture was stirred at room temperature for 3 hours. The same post treatment and HPLC purification as in synthesis of Bdev-7 were conducted, to obtain Bdev-3 (28.0 mg, 37.4%). The structure of the targeted substance was identified based on detection of mono-valent ions at 44-amu interval around m/z 3140 and divalent ions at 22-amu interval around m/z 1640 by MS measurement.

(4) Synthesis of Bdev-5

Bdev-5 was synthesized as described below.

Synthesis of Compound 22

[chemical formula 147]

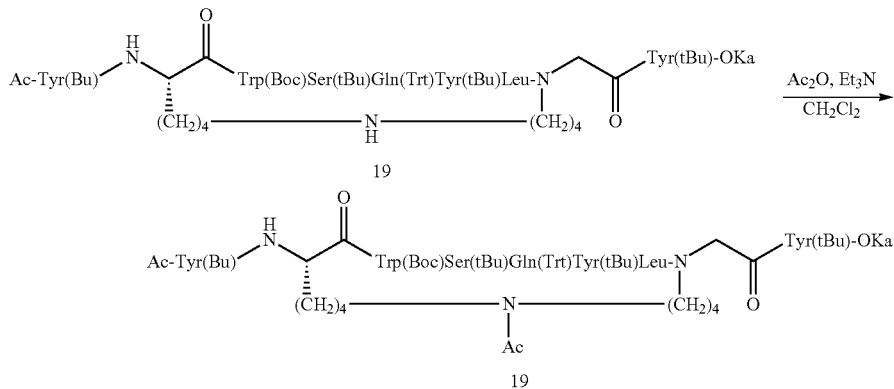

The compound 19 (161 mg, 0.0580 mmol) was dissolved in CH$_2$Cl$_2$ (1160 μL), and Et$_3$N (15.8 μL, 0.112 mmol, 1.9 equiv) and Ac$_2$O (11.0 μL, 0.116 mmol, 2.0 equiv) were added and the mixture was stirred at room temperature for 40 minutes. The same post treatment as in synthesis of the compound 4 was conducted, to obtain a compound 22 (143 mg, 87.6%).

Synthesis of Bdev-5

[chemical formula 148]

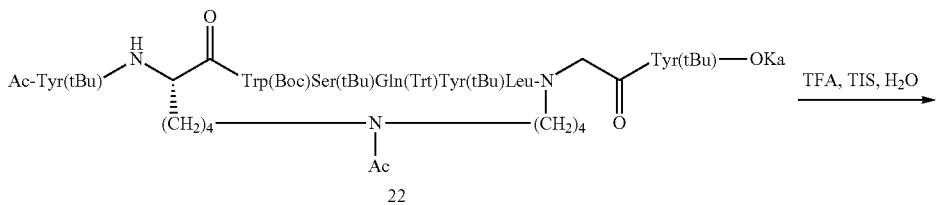

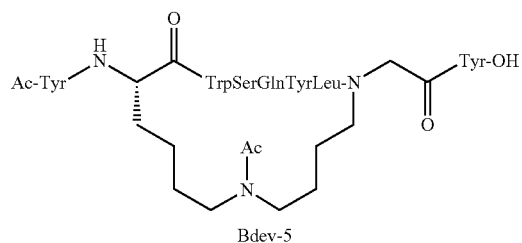

To the compound 22 (143 mg, 0.0508 mmol) was added a solution (5 mL) of TFA/TIS/H$_2$O=95:5:5 and the mixture was stirred at room temperature for 3 hours. The same post treatment and HPLC purification as in synthesis of Bdev-7 were conducted, to obtain Bdev-5 (25.6 mg, 37.4%). HRMS m/z [M+H]$^+$: calcd for C$_{68}$H$_{88}$N$_2$O$_{17}$: 1345.6499. found 1345.5516.

(5) Synthesis of Bdev-13

Bdev-13 was synthesized as described below.

[chemical formula 149]

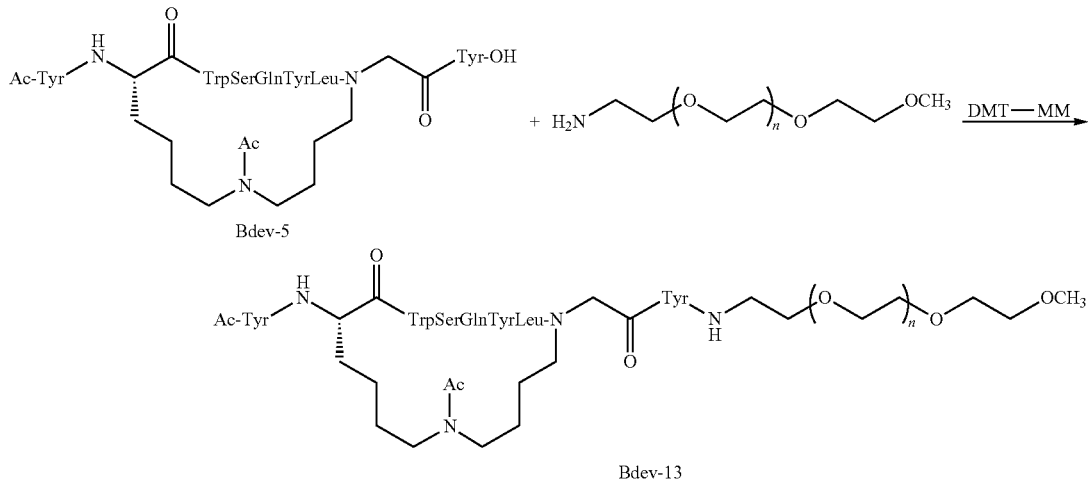

A mixture of Bdev-5 (10.1 mg, 0.00750 mmol, 1.5 equiv), MeO-PEG-NH$_2$ (MW: 2000 Da, manufactured by Iris Biotech) (10.4 mg, 0.00516 mmol) and DMT-MM (1.4 mg, 0.00506 mmol, 1.0 equiv) in THF (1100 μL) and MeOH (900 μL) was stirred at room temperature for 7 hours and 35 minutes. The solvent was evaporated under reduced pressure, then, to the residue were added PEG-NH$_2$ (10.4 mg, 0.00516 mmol), DMT-MM (5.7 mg, 0.0206 mmol) and DMF (1 mL) and the mixture was stirred at room temperature for 4 hours and 38 minutes. DMT-MM (14.2 mg, 0.0513 mmol) was added and the mixture was stirred for 1 hour and 20 minutes. Purification was performed by HPLC, to obtain Bdev-13 (3.6 mg, 14.5%). The structure of the targeted substance was identified based on detection of a group of divalent ions at 22-amu interval around m/z 1700, a group of tri-valent ions at 15-amu interval around m/z 1150 and a group of tetra-valent ions at 11-amu interval around m/z 900 by MS measurement.

Example 6

Synthesis of Intermediate for Synthesis of Bdev-2, -4, -8, and -10

Synthesis of an intermediate for synthesis of Bdev-2, -4, -8, and -10 was carried out as described below.

Synthesis of Compound 23

[chemical formula 150]

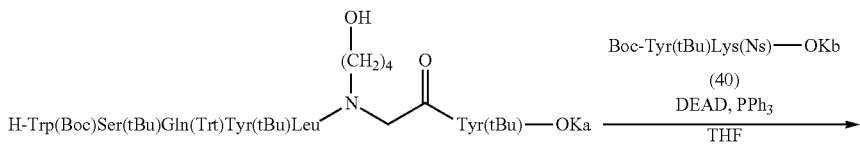

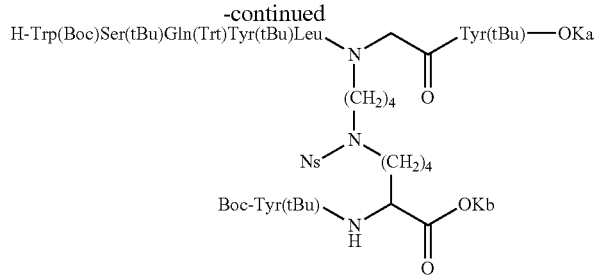

The compound 13 (890 mg, 0.372 mmol), the compound 40 (776 mg, 0.559 mmol, 1.5 equiv) and PPh₃ (147 mg, 0.559 mmol, 1.5 equiv) were dissolved in THF (8 mL), and DEAD (253 μL, 0.558 mmol, 1.5 equiv) was added and the mixture was stirred at room temperature for 54 minutes. PPh₃ (148 mg, 0.564 mmol, 1.5 equiv) was added and the mixture was stirred for 20 minutes. DEAD (84.4 μL, 0.186 mmol, 0.5 equiv) was added and the mixture was stirred for 2 hours and 20 minutes. PPh₃ (147 mg, 0.560 mmol, 1.5 equiv) was added and the mixture was stirred for 14 minutes. DEAD (33.7 μL, 0.0743 mmol, 0.2 equiv) was added and the mixture was stirred for 34 minutes. PPh₃ (44.8 mg, 0.171 mmol, 0.5 equiv) was added and the mixture was stirred for 2 minutes. DEAD (33.7 μL, 0.0743 mmol, 0.2 equiv) was added and the mixture was stirred for 3 hours and 15 minutes. DEAD (33.7 μL, 0.0743 mmol, 0.2 equiv) was added and the mixture was stirred for 21 minutes. The same post treatment as in synthesis of the compound 4 was conducted to obtain a residue, which was then subjected to silica gel column chromatography (CH₂CH₂/THF, 100:0-90:10), to obtain a Mitsunobu reaction product (1.05 g, 75.0%).

[chemical formula 151]

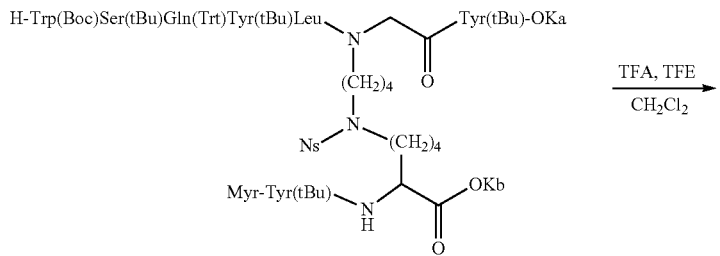

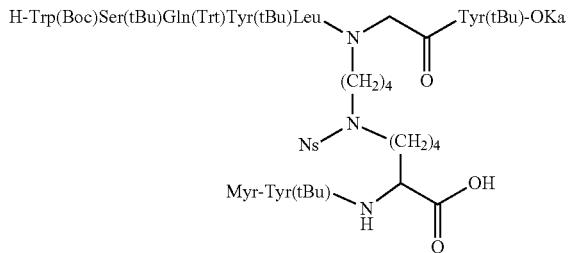

23

The Mitsunobu reaction product (637 mg, 0.169 mmol) was dissolved in CH$_2$Cl$_2$ (16.9 mL), and TFE (1690 μL) and TFA (169 μL) were added and the mixture was stirred at room temperature for 40 minutes. The precipitated material was filtrated through Celite, and the solvent was evaporated under reduced pressure. The same post treatment as in synthesis of the compound 4 was conducted to obtain a residue, which was then subjected to silica gel column chromatography (CHCl$_3$/EtOH, 100:0-95:5), to obtain a compound 23 (294 mg, 58.1%).

Synthesis of Compound 24

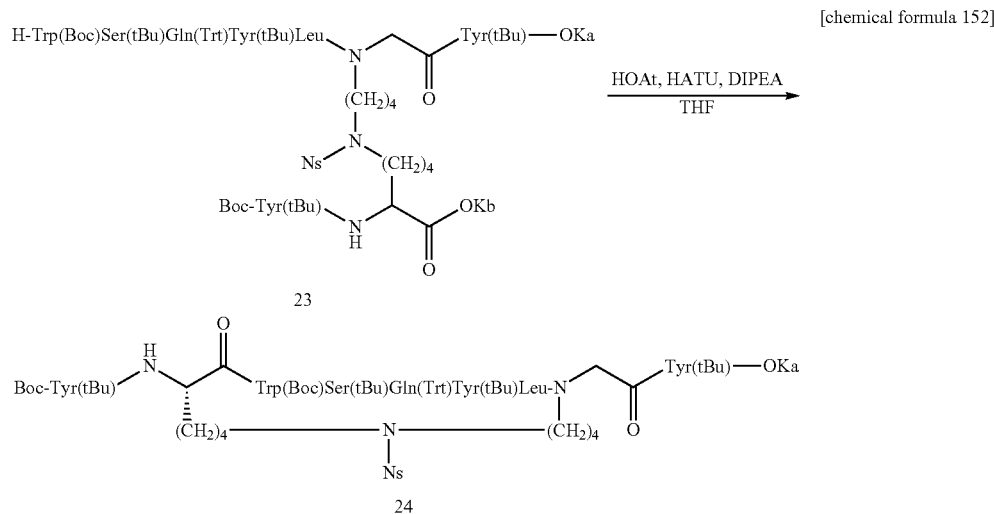

[chemical formula 152]

The compound 23 (294 mg, 0.0970 mmol), HOAt (15.8 mg, 0.116 mmol, 1.2 equiv) and HATU (44.7 mg, 0.118 mmol, 1.2 equiv) were dissolved in THF (19.4 mL), and DIPEA (84.5 μL, 0.485 mmol, 5.0 equiv) was added and the mixture was stirred at room temperature for 3 hours and 10 minutes. The same post treatment as in synthesis of the compound 4 was conducted, to obtain a compound 24 (284 mg, 97.2%).

Synthesis of Compound 25

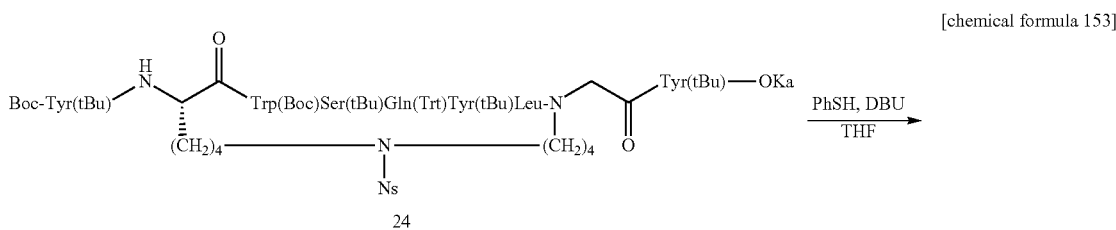

[chemical formula 153]

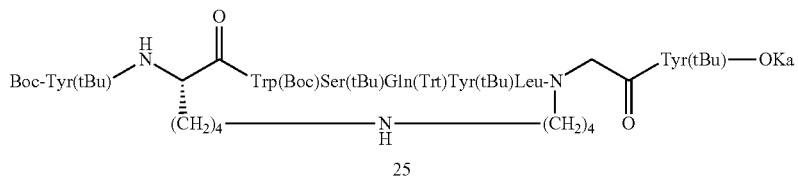

The compound 24 (284 mg, 0.0943 mmol) was dissolved in THF (943 μL), and PhSH (29.0 μL, 0.282 mmol, 3.0 equiv) and DBU (42.3 μL, 0.283 mmol, 3.0 equiv) were added and the mixture was stirred at room temperature for 2 hours and 30 minutes. The same post treatment as in synthesis of the compound 16 was conducted, to obtain a compound 25 (255 mg, 95.8%) as an intermediate for synthesis of Bdev-2, -4, -8 and -10.

Example 7

Synthesis of Bdev-2, -4, -8 and -10

(1) Synthesis of Bdev-8

Synthesis of Bdev-8 was carried out as described below.

[chemical formula 154]

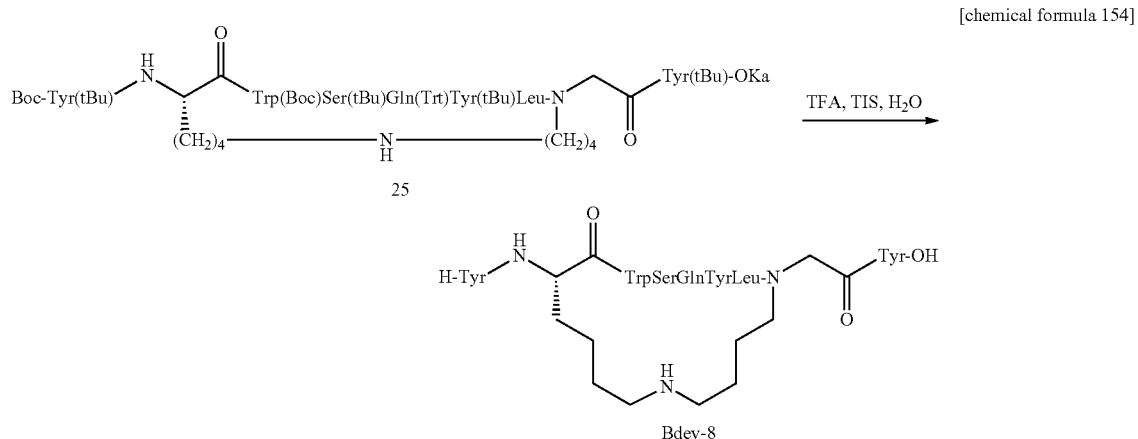

To the compound 25 (55.1 mg, 0.0181 mmol) was added a solution (1810 μL) of TFA/TIS/H$_2$O=95:5:5 and the mixture was stirred at room temperature for 3 hours. The same post treatment and HPLC purification as in synthesis of Bdev-7 were conducted, to obtain Bdev-8 (12.0 mg, 52.6%). HRMS m/z [M+H]$^+$: calcd for $C_{64}H_{85}H_{12}O_{15}$: 1261.6257. found 1261.4668.

(2) Synthesis of Bdev-4

Synthesis of Compound 26

[chemical formula 155]

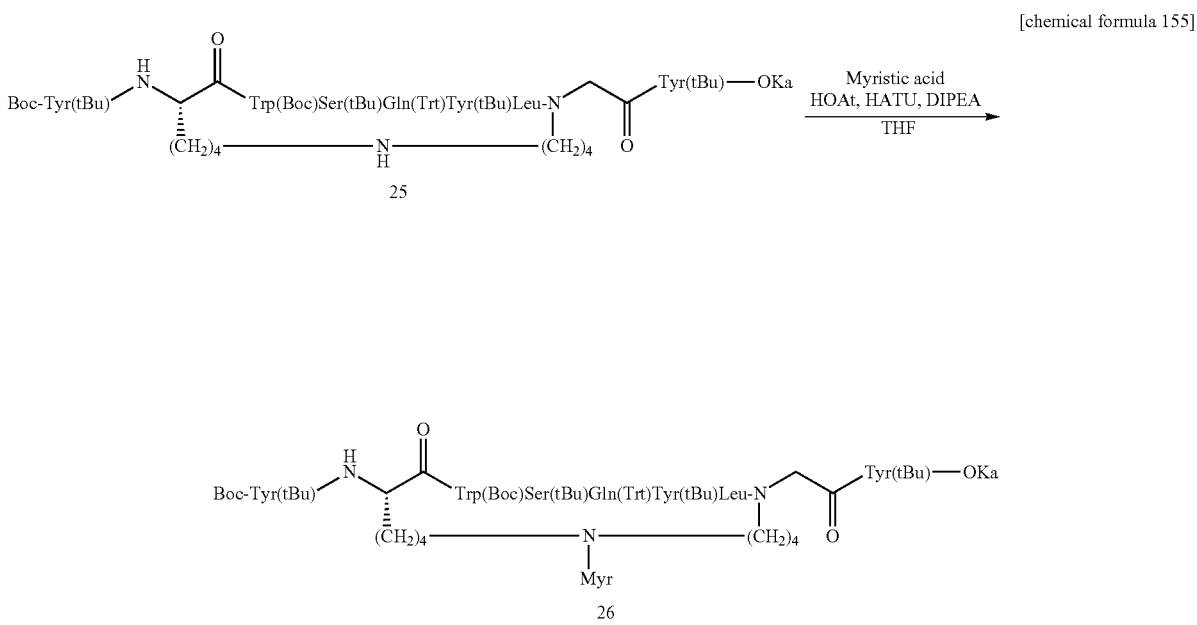

The compound 25 (62.6 mg, 0.0222 mmol), myristic acid (7.7 mg, 0.0337 mmol, 1.5 equiv), HOAt (4.5 mg, 0.0331 mmol, 1.5 equiv) and HATU (12.8 mg, 0.0337 mmol, 1.5 equiv) were dissolved in THF (444 μL), and DIPEA (19.3 μL, 0.111 mmol, 5.0 equiv) was added and the mixture was stirred at room temperature for 3 hours. The same post treatment as in synthesis of the compound 4 was conducted, to obtain a compound 26 (56.9 mg, 84.7%).

Synthesis of Bdev-4

[chemical formula 156]

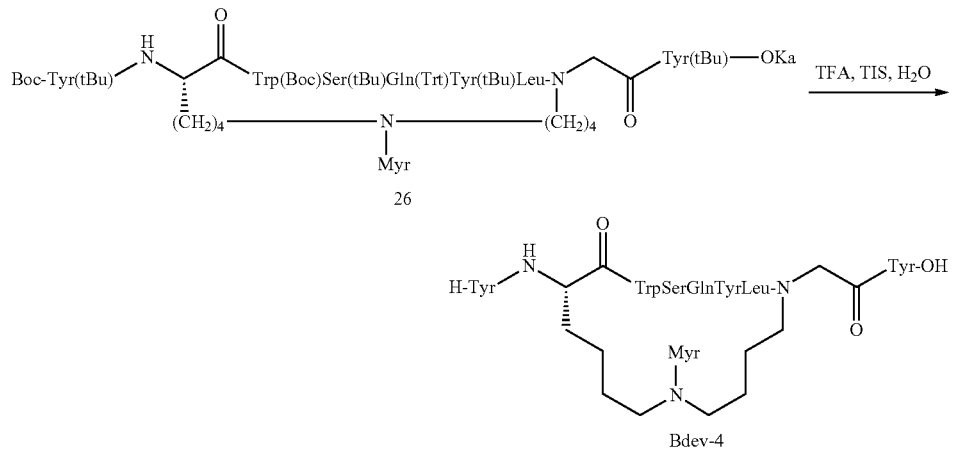

To the compound 26 (56.9 mg, 0.0188 mmol) was added a solution (1514 μL) of TFA/TIS/H$_2$O=95:5:5 and the mixture was stirred at room temperature for 5 minutes. TIS (46.9 mL) was added and the mixture was stirred for 3 hours and 55 minutes. The same post treatment as in synthesis of Bdev-7 was conducted, to obtain Bdev-4 (4.0 mg, 14.5%). HRMS m/z [M+H]$^+$: calcd for $C_{78}H_{111}N_{12}O_{16}$: 1471.8241. found 1471.8190.

(3) Synthesis of Bdev-2

Synthesis of Compound 27

[chemical formula 157]

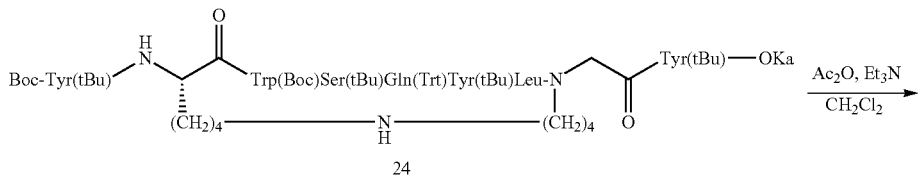

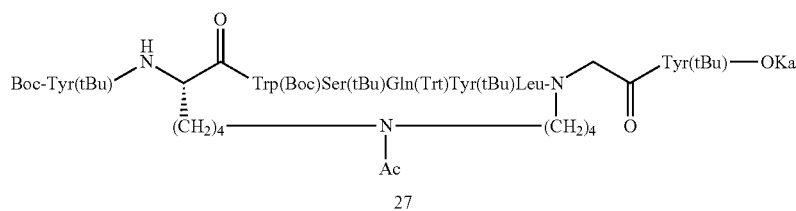

The compound 24 (204 mg, 0.0724 mmol) was dissolved in CH$_2$Cl$_2$ (1448 µL), and Et$_3$N (20.4 µL, 0.145 mmol, 2.0 equiv) and Ac$_2$O (13.7 µL, 0.145 mmol, 2.0 equiv) were added and the mixture was stirred at room temperature for 50 minutes. The same post treatment as in synthesis of the compound 4 was conducted, to obtain a compound 27 (200 mg, 96.3%).

Synthesis of Bdev-2

[chemical formula 158]

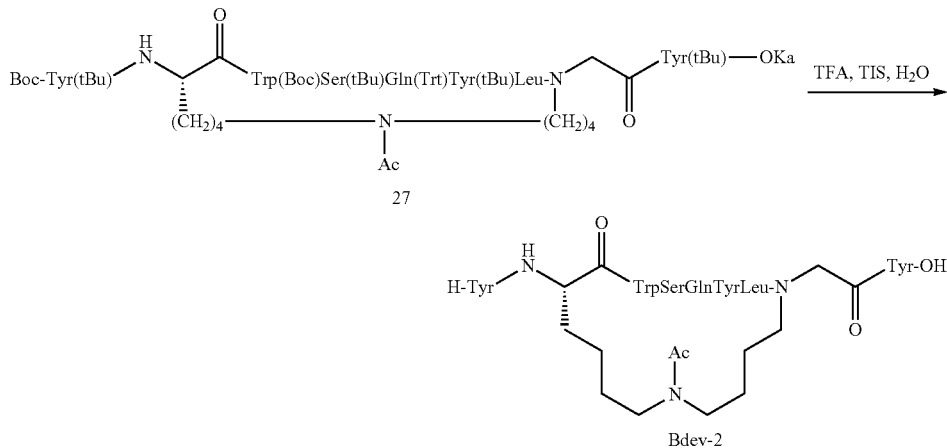

To the compound 27 (200 mg, 0.0697 mmol) was added a solution (6970 µL) of TFA/TIS/H$_2$O=95:5:5 and the mixture was stirred at room temperature for 3 hours. The same post treatment as in synthesis of Bdev-7 was conducted, to obtain Bdev-2 (54.4 mg, 59.8%). HRMS m/z [M+H]$^+$: calcd for C$_{66}$H$_{87}$N$_{12}$O$_{16}$: 1303.6363. found 1303.5524.

(4) Synthesis of Bdev-10

[chemical formula 159]

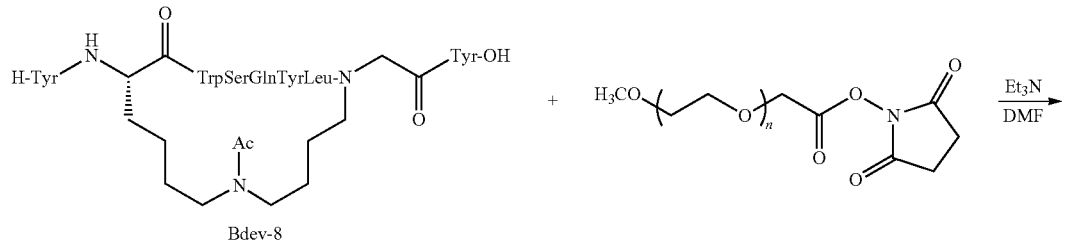

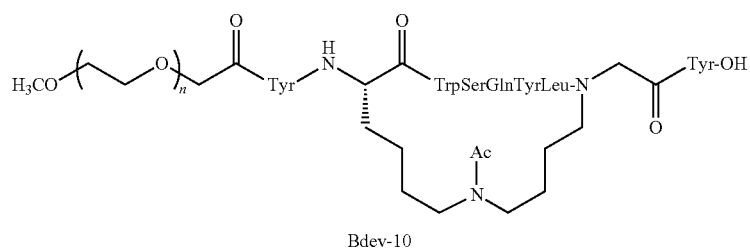

To Bdev-2 (13.1 mg, 0.0101 mmol) and SUNBRIGHT® ME-020AS (manufactured by NOF Corporation) (40.4 mg, 0.0202 mmol, 2.0 equiv) in DMF (404 µL) was added $Et_3N$ (2.84 µL, 0.0202 mmol, 2.0 equiv), and the mixture was stirred at room temperature for 22 hours and 40 minutes. Purification by HPLC was performed, to obtain Bdev-10 (16.8 mg, 48.9%).

The structure of the targeted substance was identified based on detection of divalent ions at 22-amu interval around m/z 1700 by MS measurement.

Example 8

Synthesis of Bdev-14

Figure 3:
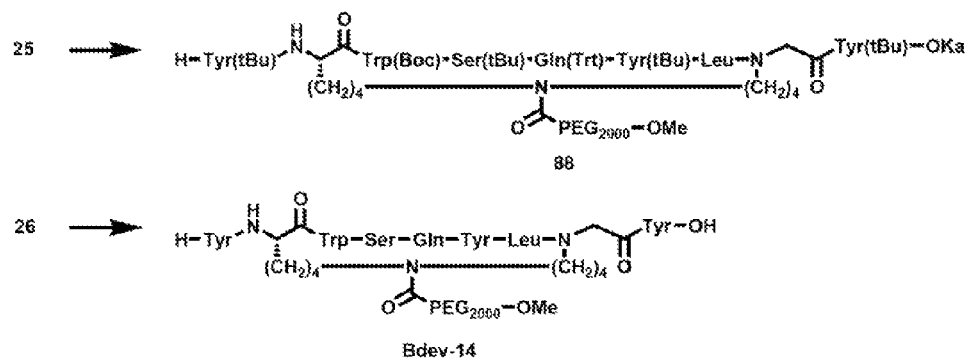
FIG. 3 shows a schematic view of a synthesis example of another W9 cross-linked peptide mimic (Bdev-14) of the present invention.

The synthesis route of Bdev-14 is shown schematically in FIG. 3.

Bdev-14 was synthesized as described below.

Synthesis of Compound 88

A mixture of the compound 25 (209 mg, 0.0739 mmol), MeO-PEG-$CO_2$H [manufactured by Iris Biotech, MW 2,000 Da] (299 mg, 0.149 mmol, 2.0 equiv), HOAt (58.5 mg, 0.430 mmol, 5.8 equiv), DIPCI (57.6 µL, 0.370 mmol, 5.0 equiv) and DIPEA (64.4 µL, 0.370 mmol, 5.0 equiv) in THF (1478 µL) was stirred at room temperature for 3 hours and 50 minutes. MeO-PEG-$CO_2$H (297 mg, 0.148 mmol, 2.0 equiv), HOAt (60.9 mg, 0.447 mmol, 6.0 equiv) and DIPCI (57.6 µL, 0.370 mmol, 5.0 equiv) were added and the mixture was stirred at room temperature for 40 minutes. The solvent was evaporated under reduced pressure, and the residue was subjected to silica gel column chromatography ($CHCl_3$/MeOH, 100:0-90:10), to obtain a compound 88 (673 mg) as a crude product.

Synthesis of Bdev-14

To the compound 88 (673 mg) was added a solution (7390 µL) of TFA/TIS/$H_2O$=95:5:5 and the mixture was stirred at room temperature for 3 hours. The precipitated material was filtrated, and the filtrate was evaporated under reduced pressure. The residue was purified by GPC, to obtain Bdev-14 (5.6 mg, 2.3%; 2 steps from compound 25). The structure of the targeted substance was identified since a group of peaks at 22-amu interval observed ranging from m/z 1400 to 1800 around m/z 1600 corresponded to a group of divalent ions derived from the PEG compound and a group of peaks at 14-amu interval observed ranging from m/z 1000 to 1200 around m/z 1100 corresponded to a group of tri-valent ions derived from the PEG compound, respectively, by MS measurement.

Example 9

Synthesis of Bdev-19

Figure 4:
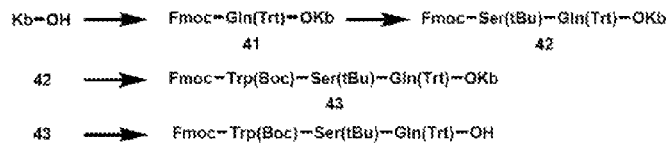
FIG. 4 shows a partial schematic view of a synthesis route of a synthesis example of still other W9 cross-linked peptide mimics (Bdev-19, -20) of the present invention.
Figure 5:
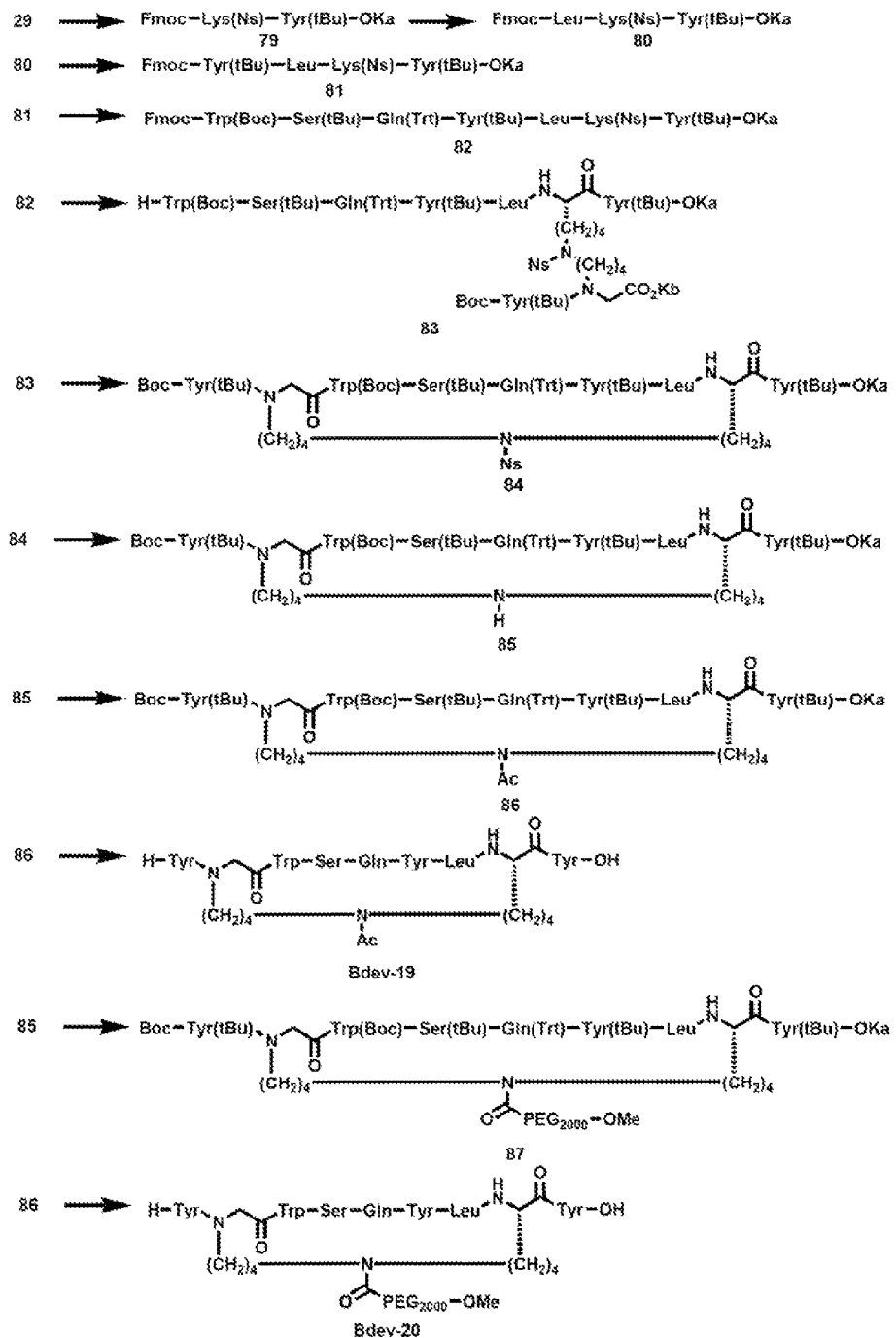
FIG. 5 shows a schematic view of a synthesis example of still other W9 cross-linked peptide mimics (Bdev-19, -20) of the present invention.

The synthesis route of Bdev-19 is shown schematically in FIG. 4 and FIG. 5.

Bdev-19 was synthesized as described below.

Synthesis of Compound 41

A compound 41 was obtained (q.y.) in the same manner as in the above-described synthesis example of the compound 1, excepting that the amino acid to be condensed was changed to Fmoc-Gln(Trt)-OH.

Synthesis of Compound 42

The compound 41 (13.50 g, 10.0 mmol) was dissolved in THF (180 mL) and DMF (20 mL), and piperidine (2000 µL) and DBU (2000 µL) were added and the mixture was stirred at room temperature for 5 minutes. Concentrated hydrochloric acid was added until pH of the reaction solution reached around 6, and the solvent was evaporated under reduced pressure. To the residue was added acetonitrile (540 mL) to find deposition of a precipitated material, which was then filtrated, and suspended and washed with acetonitrile twice, to obtain a de-Fmoc form.

The de-Fmoc form was dissolved in THF (140 mL) and DMF (60 mL), and Fmoc-Ser(tBu)-OH (4.60 g, 12.0 mmol), HOBt.$H_2O$ (1.84 g, 12.0 mmol), HBTU (4.55 g, 12.0 mmol) and DIPEA (8709 µL, 60.0 mmol) were added and the mixture was stirred at room temperature for 30 minutes. The solvent was evaporated under reduced pressure, then, to the residue was added acetonitrile (700 mL) to find deposition of a precipitated material, which was then filtrated, and suspended and washed with acetonitrile twice, to obtain a compound 42 (14.60 g, 97.8%).

Synthesis of Compound 43

A crude product obtained by treating in the same manner as in the above-described synthesis example of the compound 42 was purified by normal phase silica gel column chromatography (toluene/THF=100:0→90:10), to obtain a compound 43 (12.6 g, 72.6%), excepting that the amino acid to be condensed was changed to Fmoc-Trp(Boc)-OH.

Synthesis of Compound 91

The compound 43 (2.60 g, 14.6 mmol) was dissolved in DCM (40 mL) and TFE (4 mL), and TFA (39 µL) was added and the mixture was stirred at room temperature for 15 minutes. The precipitated material was filtrated, then, to the filtrate was added water (8 mL) and the mixture was evaporated under reduced pressure. The generated precipitate was centrifugally separated (3500 rpm, 6 min), and the precipitated material was dissolved in THF and EtOH, then, evaporated under reduced pressure. The residue was suspended and washed with IPE twice, and dried in vacuo, to obtain a compound 91 (98.6%).

Synthesis of Compound 79

A mixture of the compound 29 (1.35 g, 1.15 mmol), the compound 33 (963 mg, 1.74 mmol), HATU (656 mg, 1.73 mmol, 1.5 equiv), HOAt (235 mg, 1.73 mmol, 1.5 equiv) and DIPEA (1002 µL, 5.75 mmol, 5.0 equiv) in THF (23 mL) was stirred at room temperature for 2 hours and 30 minutes. The same post treatment as in synthesis of the compound 4 was conducted, to obtain a compound 79 (2.05 g).

Synthesis of Compound 80

The compound 79 (2.05 g) was dissolved in THF (23 mL), and piperidine (230 µL, 2.16 mmol, 1.9 equiv) and DBU (230 µL, 1.54 mmol, 1.3 equiv) were added and the mixture was stirred at room temperature for 5 minutes. The same post treatment as in synthesis of the compound 2 was conducted, to obtain a de-Fmoc form (1.68 g, 98.3% from compound 29).

The de-Fmoc form (1.68 g, 1.13 mmol) was dissolved in THF (23 mL), and Fmoc-Leu-OH (598 mg, 1.69 mmol, 1.5 equiv), HATU (646 mg, 1.70 mmol, 1.5 equiv), HOAt (233 mg, 1.71 mmol, 1.5 equiv) and DIPEA (984 μL, 5.65 mmol, 5.0 equiv) were added and the mixture was stirred at room temperature for 40 minutes. The same post treatment as in synthesis of the compound 4 was conducted, to obtain a compound 80 (1.92 g, 95.6%).

Synthesis of Compound 81

A compound 81 was synthesized (95.5% from compound 80) in the same manner as in the above-described synthesis example of the compound 80, excepting that the amino acid to be condensed was changed to Fmoc-Tyr(tBu)-OH.

Synthesis of Compound 82

A de-Fmoc form was obtained (99.2%) in the same manner as in the above-described synthesis example of the compound 80, excepting that the starting material was changed to the compound 81.

The de-Fmoc form (1.75 g, 0.966 mmol) was dissolved in THF (20 mL), and the compound 91 (1.51 g, 1.45 mmol, 1.5 equiv), HATU (551 mg, 1.45 mmol, 1.5 equiv), HOAt (197 mg, 1.45 mmol, 1.5 equiv) and DIPEA (841 μL, 4.83 mmol, 5.0 equiv) were added and the mixture was stirred at room temperature for 30 minutes. DIPCI (150 μL, 0.963 mmol, 1.0 equiv) and HOAt (197 mg, 1.45 mmol, 1.5 equiv) were added and the mixture was stirred for 30 minutes. The same post treatment as in synthesis of the compound 4 was conducted, to obtain a compound 82 (2.60 g, 98.2%).

Synthesis of Compound 83

A de-Fmoc form was obtained (97.8%) in the same manner as in the above-described synthesis example of the compound 80, excepting that the starting material was changed to the compound 82.

The de-Fmoc form (2.34 g, 0.909 mmol), the compound 90 (2.17 g, 1.80 mmol, 2.0 equiv) and PPh$_3$ (944 mg, 3.60 mmol, 4.0 equiv) were dissolved in THF (18 mL), and DEAD (1628 μL, 3.59 mmol, 3.9 equiv) was added and the mixture was stirred at room temperature for 2 hours. The same post treatment as in synthesis of the compound 4 was conducted to obtain a residue, which was then subjected to silica gel column chromatography (toluene/THF, 100:0-85:15), to obtain a compound 83 (1.88 g, 54.9%).

Synthesis of Compound 84

A compound 84 was obtained (78.8%) in the same manner as in the above-described synthesis example of the compound 15, excepting that the starting material was changed to the compound 83.

Synthesis of Compound 85

The compound 84 (403 mg, 0.134 mmol) was dissolved in THF (1340 μl), and PhSH (138 μL, 1.34 mmol, 10 equiv) and DBU (200 μL, 1.34 mmol, 10 equiv) were added and the mixture was stirred at room temperature for 50 minutes. To the reaction solution was added concentrated hydrochloric acid (112 μl), then, the same post treatment as for synthesis of the compound 5 was conducted, to obtain a compound 85 (343 mg, 90.3%).

Synthesis of Compound 86

A compound 86 was obtained (144 mg, 82.8%) in the same manner as in the above-described synthesis example of the compound 22, excepting that the starting, material was changed to the compound 85.

Synthesis of Bdev-19

Bdev-19 was obtained in the same manner as in the above-described synthesis example of Bdev-5, excepting that the starting material was changed to the compound 86. HRMS m/z [M+H]$^+$: calcd for $C_{66}H_{87}N_{12}O_{16}$: 1303.64. found 1303.87.

Example 10

Synthesis of Bdev-20

The synthesis route of Bdev-20 is shown schematically in FIG. 5.

Bdev-20 was synthesized as described below.

Synthesis of Compound 87

A compound 87 (340 mg) was obtained as a crude product in the same manner as in the above-described synthesis example of the compound 21, excepting that the starting material was changed to the compound 85 (172 mg).

Synthesis of Bdev-20

Bdev-20 was obtained (7.8%; 2 steps form compound 85) in the same manner as in the above-described synthesis example of Bdev-3, excepting that the starting material was changed to the compound 87. The structure of the targeted substance was identified since a group of peaks at 22-amu interval observed ranging from m/z 1400 to 1800 around m/z 1600 corresponded to a group of divalent ions derived from the PEG compound and a group of peaks at 14-amu interval observed ranging from m/z 1000 to 1200 around m/z 1060 corresponded to a group of tri-valent ions derived from the PEG compound, respectively, by MS measurement.

Example 11

Synthesis of Bdev-21

Figure 6:
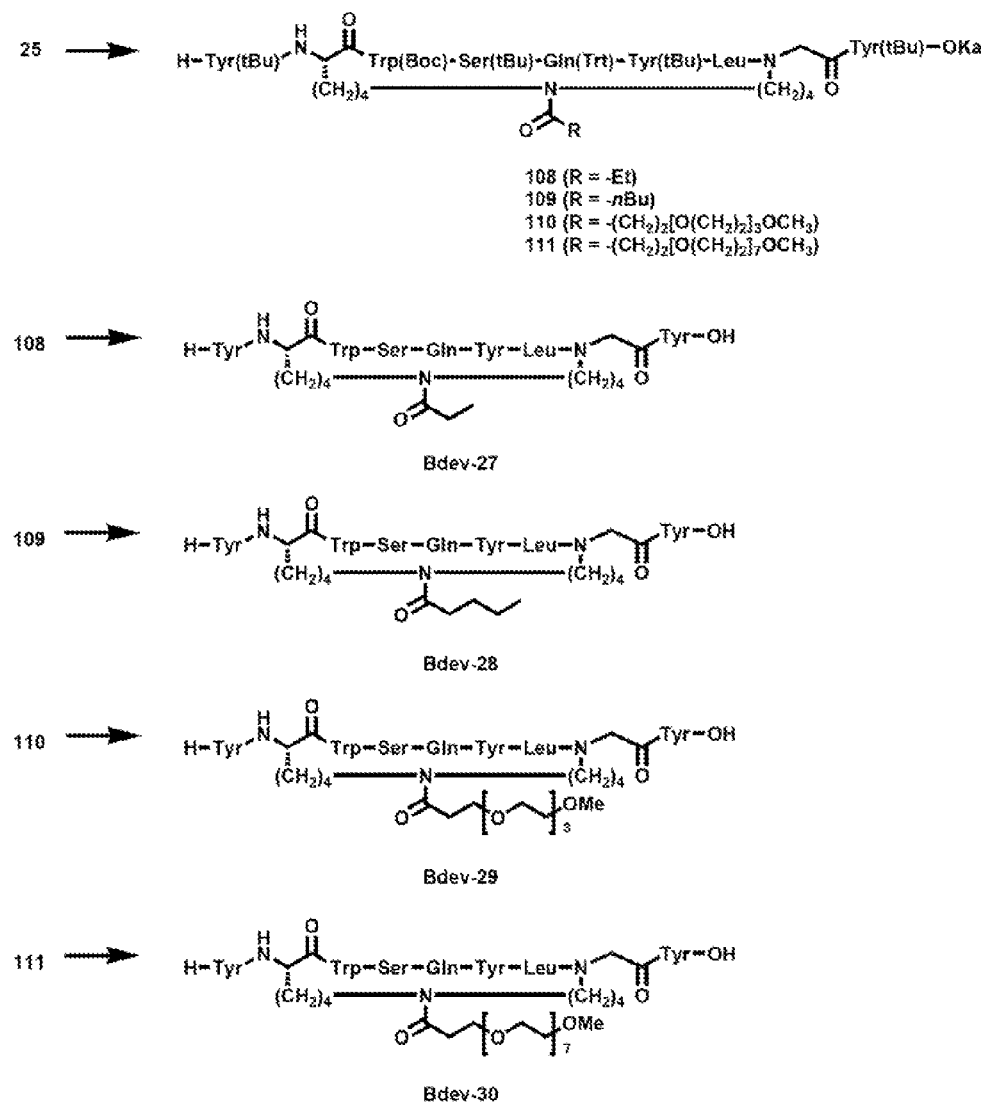
FIG. 6 shows a schematic view of a synthesis example of still another W9 cross-linked peptide mimic (Bdev-21) of the present invention.

The synthesis route of Bdev-21 is shown schematically in FIG. 6.

Bdev-21 was synthesized as described below.

Synthesis of Compound 89

The compound 5 (10.9 g, 9.69 mmol) was dissolved in THF (200 mL), and Boc-Tyr(tBu)-OH (4.90 g, 14.5 mmol, 1.5 equiv), HATU (5.53 g, 14.5 mmol, 1.5 equiv), HOAt (1.98 g, 14.6 mmol, 1.5 equiv) and DIPEA (8439 μL, 48.5 mmol, 5.0 equiv) were added and the mixture was stirred at room temperature for 1 hour and 30 minutes. Boc-Tyr(tBu)-OH (1.63 g, 4.83 mmol, 0.5 equiv) and HOAt (664 mg, 4.88 mmol, 0.5 equiv) were added and the mixture was stirred for 1 hour and 10 minutes. The solvent was evaporated under reduced pressure, and to the residue was added CH$_3$CN to find deposition of a precipitated material, which was then filtrated, and suspended and washed with CH$_3$CN twice to obtain a residue, which was then subjected to silica gel column chromatography (n-hexane/EtOAc=100:0-85:15), to obtain a compound 89 (11.0 g, 78.6%).

Synthesis of Compound 90

The compound 89 (11.0 g, 7.62 mmol) was dissolved in THF (70 mL), and TBAF (1.0 M solution in THF, 30.0 mL, 30.0 mmol, 3.9 equiv) was added and the mixture was stirred at room temperature for 13 hours. To the reaction solution was added $CH_2Cl_2$ and the mixture was washed with a saturated $NH_4Cl$ aqueous solution, water and saturated saline, and the organic layer was dried over anhydrous $MgSO_4$, filtrated, then, the filtrate was evaporated under reduced pressure. The residue was subjected to silica gel column chromatography (toluene/THF, 100:0-85:15), to obtain a compound 90 (3.89 g, 51.0%).

Synthesis of Compound 92

The compound 90 (259 mg, 0.215 mmol), $NsNH_2$ (104 mg, 0.514 mmol, 2.4 equiv) and $PPh_3$ (105 mg, 0.400 mmol, 1.9 equiv) were dissolved in THF (2 mL), and DEAD (181 μL, 0.399 mmol, 1.9 equiv) was added and the mixture was stirred at room temperature for 3 hours and 55 minutes. $PPh_3$ (13.3 mg, 0.0507 mmol, 0.24 equiv) and DEAD (22.7 μL, 0.0501 mmol, 0.24 equiv) were added and the mixture was stirred for 45 minutes. The same post treatment as in synthesis of the compound 4 was conducted, to obtain a compound 92 (293 mg, 98.1%).

Synthesis of Compound 93

The compound 13 (884 mg, 0.369 mmol), the compound 92 (536 mg, 0.385 mmol, 1.04 equiv) and $PPh_3$ (197 mg) were dissolved in THF (7.4 mL), and DEAD (168 μL) was added and the mixture was stirred at room temperature for 30 minutes. Further, $PPh_3$ (97.7 mg, 0.372 mmol, 1.0 equiv) and DEAD (84.0 μL, 0.185 mmol, 0.5 equiv) were added and the mixture was stirred for 30 minutes. Further, $PPh_3$ (97.6 mg, 0.372 mmol, 1.0 equiv) and DEAD (84.0 μL, 0.185 mmol, 0.5 equiv) were added and the mixture was stirred for 1 hour and 50 minutes. Further, $PPh_3$ (97.9 mg, 0.373 mmol, 1.0 equiv) and DEAD (84.0 μL, 0.185 mmol, 0.5 equiv) were added and the mixture was stirred for 40 minutes. Further, $PPh_3$ (98.3 mg, 0.375 mmol, 1.0 equiv) and DEAD (84.0 μL, 0.185 mmol, 0.5 equiv) were added and the mixture was stirred for 30 minutes. The same post treatment as in synthesis of the compound 4 was conducted to obtain a residue, which was then subjected to silica gel column chromatography ($CH_2Cl_2$/THF, 100:0-90:10), to obtain a compound 93 (886 mg, 63.7%).

Synthesis of Compound 94

A compound 94 was obtained (68.0% from compound 93) in the same manner as in the above-described synthesis example of the compound 84, excepting that the starting material was changed to the compound 93.

Synthesis of Compound 95

A compound 95 was obtained (110 mg, 82.6%) in the same manner as in the above-described synthesis example of the compound 85, excepting that the starting material was changed to the compound 94.

Synthesis of Compound 96

A compound 96 was obtained (76.4%) in the same manner as in the above-described synthesis example of the compound 86, excepting that the starting material was changed to the compound 95.

Synthesis of Bdev-21

Bdev-21 was obtained (27.0%) in the same manner as in the above-described synthesis example of Bdev-19, excepting that the starting material was changed to the compound 95. HRMS m/z $[M+H]^+$: calcd for $C_{66}H_{87}N_{12}O_{16}$: 1303.6363. found 1303.5704.

Example 12

Synthesis of Bdev-25

Figure 7:
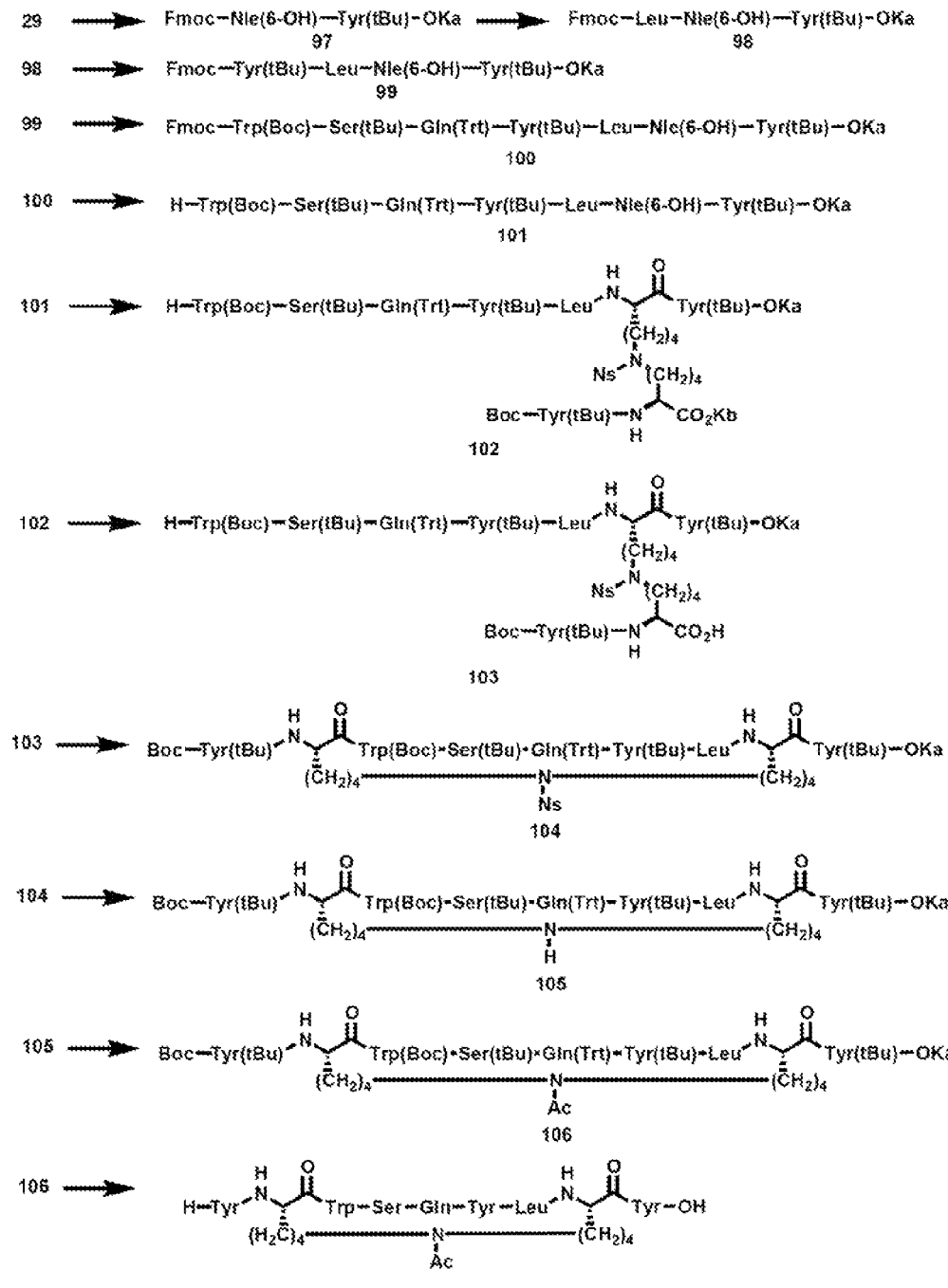
FIG. 7 shows a schematic view of a synthesis example of still another W9 cross-linked peptide mimic (Bdev-25) of the present invention.

The synthesis route of Bdev-25 is shown schematically in FIG. 7.
Bdev-25 was synthesized as described below.

Synthesis of Compound 97

A mixture of the compound 29 (2.35 g, 2.02 mmol), Fmoc-Nle(6-OH)—OH (890 mg, 2.41 mmol, 1.2 equiv), DMT-MM (860 mg, 3.11 mmol, 1.5 equiv) and DIPEA (697 μL, 4.00 mmol, 2.0 equiv) in THF (40 mL) was stirred at room temperature for 40 minutes. The same post treatment as in synthesis of the compound 4 was conducted, to obtain a compound 97 (2.97 g; 99.0%).

Synthesis of Compound 98

A compound 98 was obtained (89.6%) in the same manner as in the above-described synthesis example of the compound 80, excepting that the compound 97 was used as the starting material and the amino acid to be condensed was changed to Fmoc-Leu-OH.

Synthesis of Compound 99

A compound 99 was obtained (2.65 g, 96.6%) in the same manner as in the above-described synthesis example of the compound 81, excepting that the compound 98 was used as the starting material and the amino acid to be condensed was changed to Fmoc-Tyr(tBu)-OH.

Synthesis of Compound 100

A compound 100 was obtained (97.1%) in the same manner as in the above-described synthesis example of the compound 82, excepting that the compound 99 was used as the starting material.

Synthesis of Compound 101

The compound 100 (3.60 g, 1.37 mmol) was dissolved in THF (30 mL), and piperidine (300 μL) and DBU (300 μL) were added and the mixture was stirred at room temperature for 5 minutes. The same post treatment as in synthesis of the compound 2 was conducted, to obtain a compound 101 (3.20 g, 97.8%).

Synthesis of Compound 102

The compound 101 (3.20 g, 1.34 mmol), the compound 40 (4.67 g, 3.36 mmol, 2.5 equiv) and $PPh_3$ (1.41 g, 5.36 mmol, 4.0 equiv) were dissolved in THF (27 mL), and DEAD (2430 µL, 5.36 mmol, 4.0 equiv) was added and the mixture was stirred at room temperature for 45 minutes. The same post treatment as in synthesis of the compound 4 was conducted to obtain a residue, which was then subjected to silica gel column chromatography (toluene/THF, 100:0-80:20), to obtain a compound 102 (2.51 g, 49.7%).

Synthesis of Compound 103

A compound 103 was obtained (93.5%) in the same manner as in the above-described synthesis example of the compound 14, excepting that the compound 102 was used as the starting material.

Synthesis of Compound 104

A compound 104 was obtained (93.7%) in the same manner as in the above-described synthesis example of the compound 15, excepting that the compound 103 was used as the starting material.

Synthesis of Compound 105

A compound 105 was obtained (92.8%) in the same manner as in the above-described synthesis example of the compound 16, excepting that the compound 104 was used as the starting material.

Synthesis of Compound 106

A compound 106 was obtained (86.6%) in the same manner as in the above-described synthesis example of the compound 22, excepting that the compound 105 was used as the starting material.

Synthesis of Bdev-25

Bdev-25 was obtained (27.1%) in the same manner as in the above-described synthesis example of Bdev-5, excepting that the compound 106 was used as the starting material. HRMS m/z [M+H]$^+$: calcd for $C_{66}H_{87}N_{12}O_{16}$: 1303.64. found 1303.72.

Example 13

Synthesis of Bdev-27, 28, 29 and 30

The synthesis route of Bdev-27, 28, 29 and 30 is shown schematically in FIG. 8.

Bdev-27, 28, 29 and 30 were synthesized as described below.

Synthesis of Compound 108

The compound 25 (319 mg, 0.113 mmol) was dissolved in $CH_2Cl_2$ (2 mL), and $Et_3N$ (31.8 µL, 0.226 mmol, 2.0 equiv) and propionic anhydride (29.1 µL, 0.226 mmol, 2.0 equiv) were added and the mixture was stirred at room temperature for 45 minutes. The same post treatment as in synthesis of the compound 4 was conducted, to obtain a compound 108 (301 mg, 92.9%).

Synthesis of Compound 109

A compound 109 was obtained (90.7%) in the same manner as in the above-described synthesis example of the compound 108, excepting that n-valeric anhydride was used instead of propionic anhydride.

Synthesis of Compound 110

The compound 25 (315 mg, 0.111 mmol), MeO—[(CH$_2$)$_2$O]$_3$CH$_2$CH$_2$CO$_2$H (manufactured by Chempep: 31.3 mg, 0.132 mmol, 1.2 equiv), HOAt (18.3 mg, 0.134 mmol, 1.2 equiv) and HATU (55.2 mg, 0.145 mmol, 1.3 equiv) were dissolved in THF (2220 µL), and DIPEA (96.7 µL, 0.555 mmol, 5.0 equiv) was added and the mixture was stirred at room temperature for 2 hours and 10 minutes. The same post treatment as in synthesis of the compound 4 was conducted, to obtain a compound 110 (176 mg, 52.2%).

Synthesis of Compound 111

A compound III was obtained (40.9%) in the same manner as in the above-described synthesis example of the compound 110, excepting that MeO—[(CH$_2$)$_2$O]$_7$CH$_2$CH$_2$CO$_2$H was used instead of MeO—[(CH$_2$)$_2$O]$_3$CH$_2$CH$_2$CO$_2$H.

Synthesis of Bdev-27

To the compound 108 (301 mg, 0.105 mmol) were added a solution (10 mL) of TFA/TIS/H$_2$O=95:5:5 and TIS (1 mL) and the mixture was stirred at room temperature for 4 hours and 30 minutes. The same post treatment as in synthesis of Bdev-7 was conducted, to obtain Bdev-27 (28.6 mg, 20.7%). HRMS m/z [M+H]$^+$: calcd for $C_{67}H_{89}N_{12}O_{16}$: 1317.65. found 1317.52.

Synthesis of Bdev-28

Bdev-28 was obtained (33.7%) in the same manner as in the above-described synthesis example of Bdev-27, excepting that the compound 109 was used as the starting material. HRMS m/z [M+H]$^+$: calcd for $C_{69}H_{93}N_{12}O_{16}$: 1345.68. found 1345.58.

Synthesis of Bdev-29

Bdev-29 was obtained (18.1%) in the same manner as in the above-described synthesis example of Bdev-27, excepting that the compound 110 was used as the starting material. HRMS m/z [M+H]$^+$: calcd for $C_{74}H_{103}N_{12}O_{20}$: 1479.74. found 1479.57.

Synthesis of Bdev-30

Bdev-30 was obtained (4.9%) in the same manner as in the above-described synthesis example of Bdev-27, excepting that the compound III was used as the starting material. HRMS m/z [M+H]$^+$: calcd for $C_{82}H_{119}N_{12}O_{24}$: 1655.85. found 1655.67.

Example 14

Synthesis of Bdev-31

Figure 9:
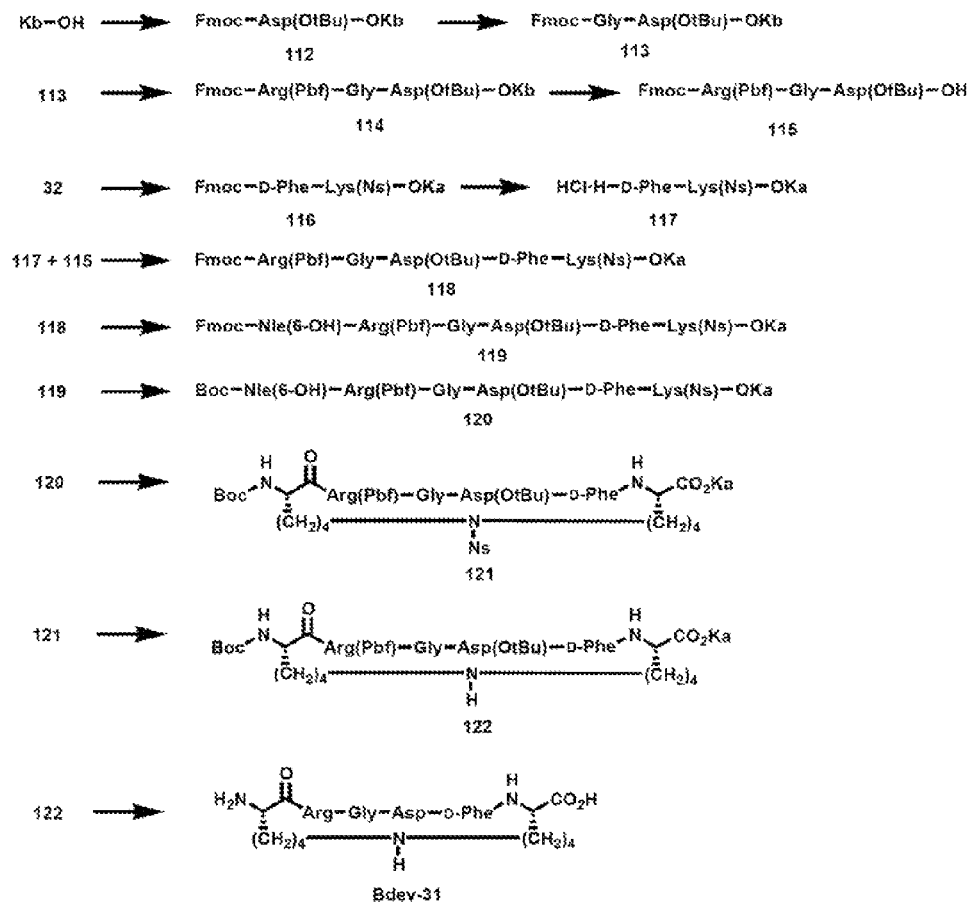
FIG. 9 shows a schematic view of a synthesis example of still another cross-linked peptide mimic (Bdev-31) of the present invention.
Figure 10:
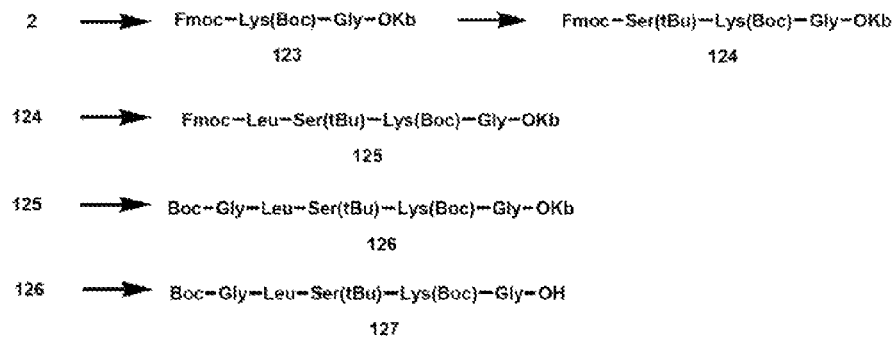
FIG. 10 shows a partial schematic view of a synthesis route of a synthesis example of still another cross-linked peptide mimic (Bdev-32) of the present invention.
Figure 11:
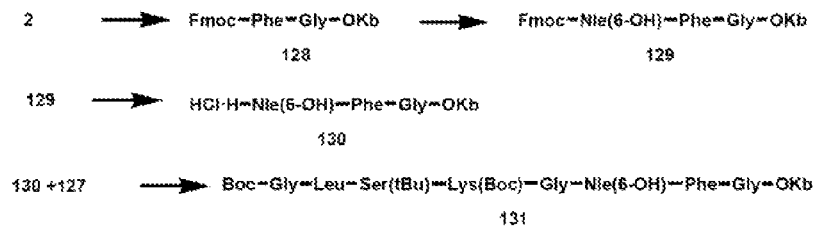
FIG. 11 shows a partial schematic view of a synthesis route of a synthesis example of still another cross-linked peptide mimic (Bdev-32) of the present invention.
Figure 12:
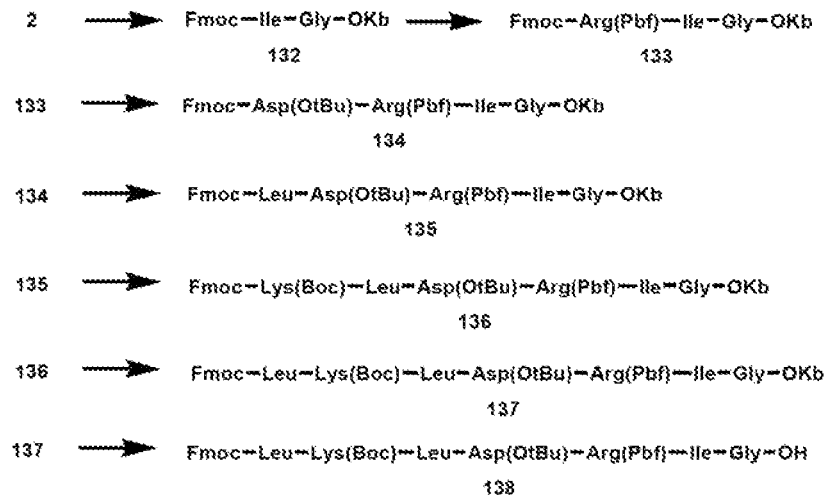
FIG. 12 shows a partial schematic view of a synthesis route of a synthesis example of still another cross-linked peptide mimic (Bdev-32) of the present invention.
Figure 13:
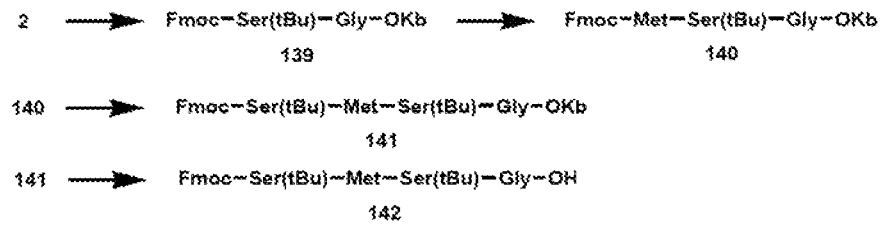
FIG. 13 shows a partial schematic view of a synthesis route of a synthesis example of still another cross-linked peptide mimic (Bdev-32) of the present invention.
Figure 14:
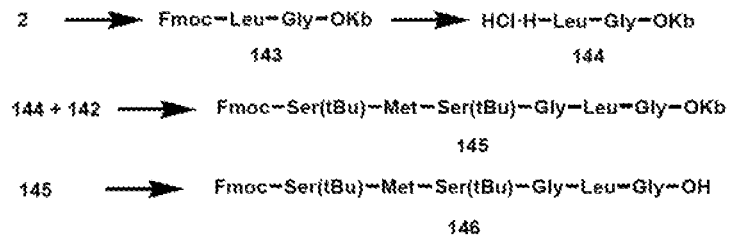
FIG. 14 shows a partial schematic view of a synthesis route of a synthesis example of still another cross-linked peptide mimic (Bdev-32) of the present invention.
Figure 15:
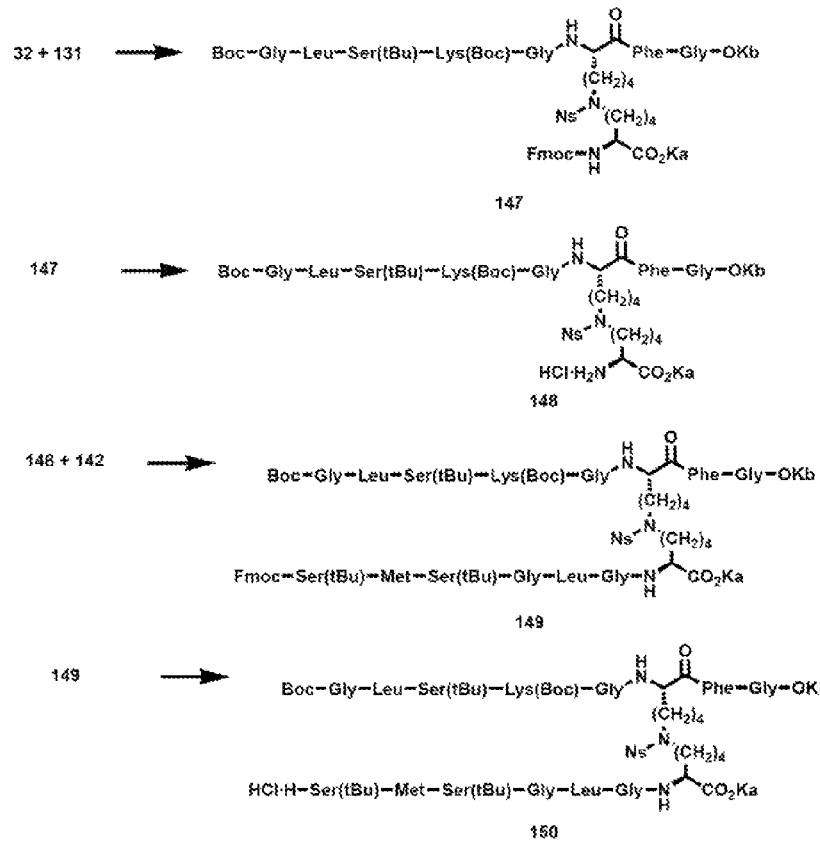
FIG. 15 shows a partial schematic view of a synthesis route of a synthesis example of still another cross-linked peptide mimic (Bdev-32) of the present invention.
Figure 16:
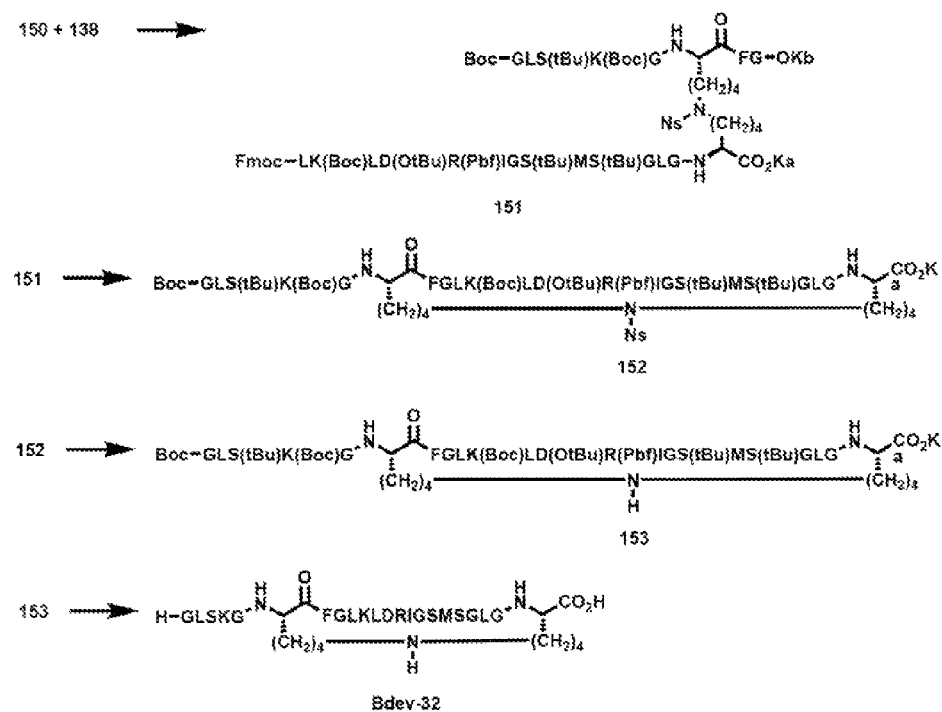
FIG. 16 shows a partial schematic view of a synthesis route of a synthesis example of still another cross-linked peptide mimic (Bdev-32) of the present invention.
Figure 17:
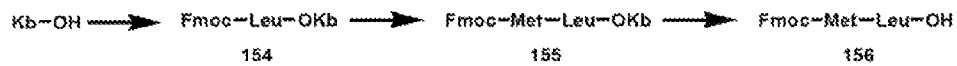
FIG. 17 shows a partial schematic view of a synthesis route of a synthesis example of still another cross-linked peptide mimic (Bdev-33) of the present invention.
Figure 18:
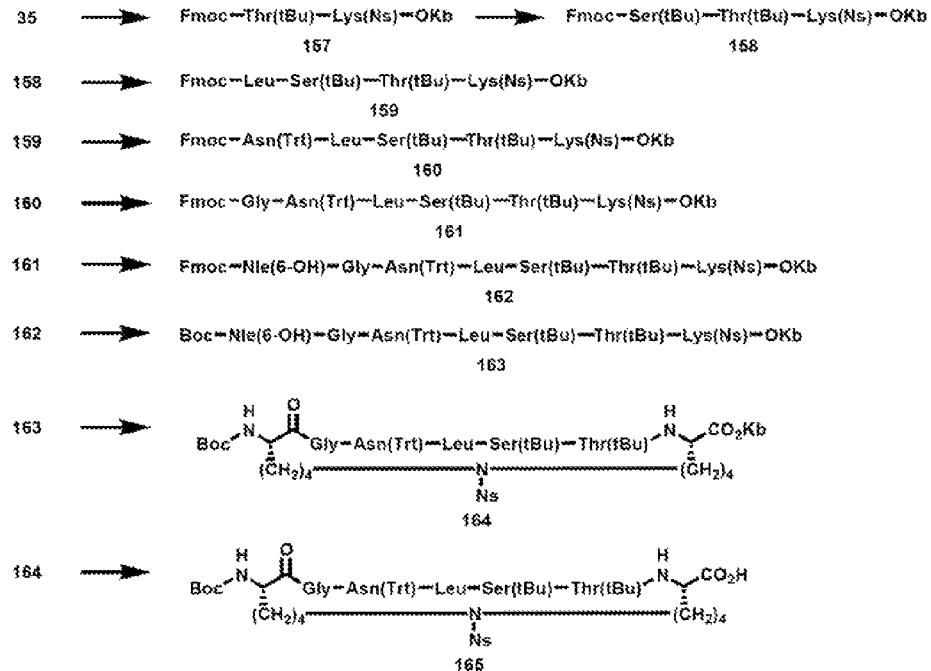
FIG. 18 shows a partial schematic view of a synthesis route of a synthesis example of still another cross-linked peptide mimic (Bdev-33) of the present invention.
Figure 19:
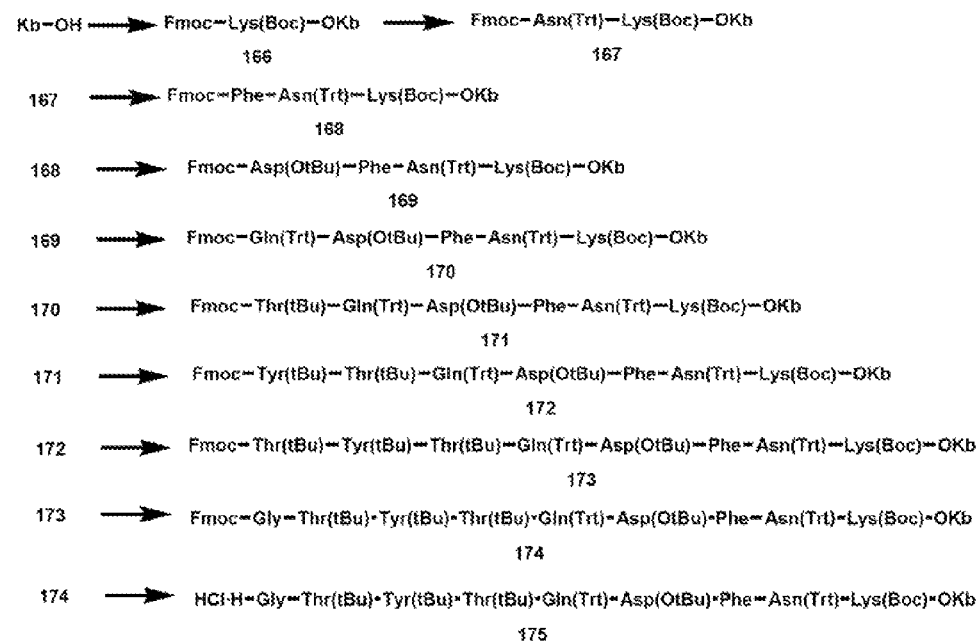
FIG. 19 shows a partial schematic view of a synthesis route of a synthesis example of still another cross-linked peptide mimic (Bdev-33) of the present invention.
Figure 20:
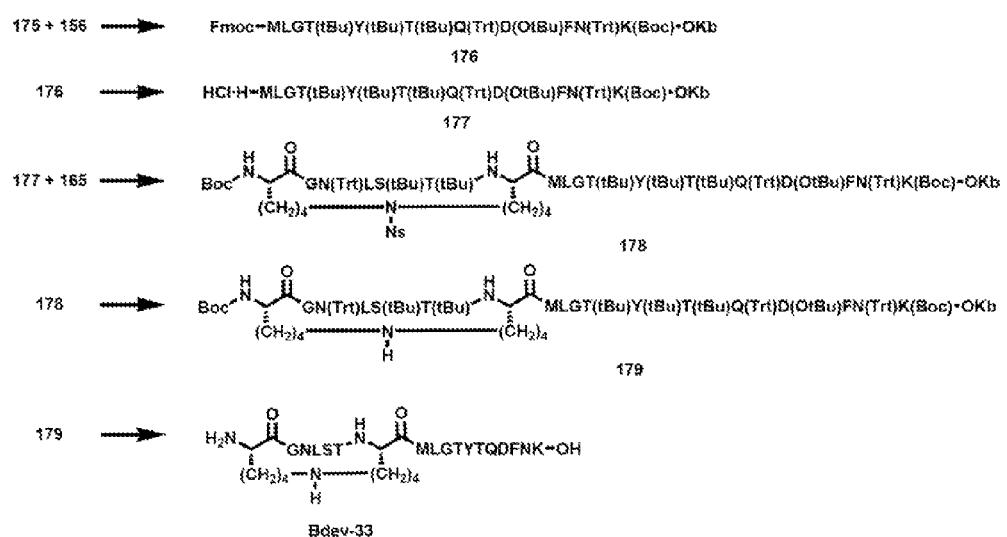
FIG. 20 shows a partial schematic view of a synthesis route of a synthesis example of still another cross-linked peptide mimic (Bdev-33) of the present invention.

The synthesis route of Bdev-31 is shown schematically in FIG. 9.
Bdev-31 was synthesized as described below.

Synthesis of Compound 112

A compound 112 was obtained (q. y.) in the same manner as in the above-described synthesis example of the compound 1, excepting that the amino acid to be condensed was changed to Fmoc-Asp(OtBu)-OH.

Synthesis of Compound 113

A compound 113 was obtained (q. y.) in the same manner as in the above-described synthesis example of the compound 42, excepting that the compound 112 was used as the starting material and the amino acid to be condensed was changed to Fmoc-Gly-OH.

Synthesis of Compound 114

A compound 114 was obtained (15.9 g, 98.1%, 5 steps from Kb-OH) in the same manner as in the above-described synthesis example of the compound 42, excepting that the compound 113 was used as the starting material and the amino acid to be condensed was changed to Fmoc-Arg(Pbf)-OH.

Synthesis of Compound 115

A compound 115 was obtained (87.0%) in the same manner as in the above-described synthesis example of the compound 91, excepting that the compound 114 was used as the starting material.

Synthesis of Compound 116

The compound 32 (2.32 g, 1.60 mmol) was dissolved in THF (32 mL), and piperidine (238 μL, 2.24 mmol, 1.4 equiv) and DBU (321 μL, 2.15 mmol, 1.3 equiv) were added and the mixture was stirred at room temperature for 5 minutes. The same post treatment as in synthesis of the compound 2 was conducted, to obtain a de-Fmoc form (2.01 g, 99.0%).

The de-Fmoc form (2.01 g, 1.59 mmol) was dissolved in THF (29 mL) and DMF (3.2 mL), and Fmoc-D-Phe-OH (924 mg, 2.38 mmol, 1.5 equiv), DMT-MM (904 mg, 3.27 mmol, 2.1 equiv) and DIPEA (277 μL, 1.59 mmol, 1.0 equiv) were added and the mixture was stirred at room temperature for 30 minutes, then, evaporated under reduced pressure. The same post treatment as in synthesis of the compound 4 was conducted, to obtain a compound 116 (2.50 g, 98.4%).

Synthesis of Compound 117

The compound 116 (2.50 g, 1.56 mmol) was dissolved in THF (31 mL), and piperidine (232 μL, 2.18 mmol, 1.4 equiv) and DBU (313 μL, 2.09 mmol, 1.3 equiv) were added and the mixture was stirred at room temperature for 5 minutes. The same post treatment as in synthesis of the compound 2 was conducted, to obtain a compound 117 (2.26 g, q. y.).

Synthesis of Compound 118

The compound 117 (2.16 g, 1.53 mmol) was dissolved in THF (28 mL) and DMF (3 mL), and the compound 115 (2.02 g, 2.30 mmol, 1.5 equiv), DMT-MM (918 g, 3.32 mmol, 2.2 equiv) and DIPEA (1334 μL, 7.66 mmol, 5.0 equiv) were added and the mixture was stirred at room temperature for 30 minutes, then, evaporated under reduced pressure. The same post treatment as in synthesis of the compound 4 was conducted, to obtain a compound 118 (3.41 g, 99.7%).

Synthesis of Compound 119

The compound 118 (3.41 g, 1.53 mmol) was dissolved in THF (31 mL), and piperidine (227 μL, 2.13 mmol, 1.4 equiv) and DBU (305 μL, 2.04 mmol, 1.3 equiv) were added and the mixture was stirred at room temperature for 5 minutes. The same post treatment as in synthesis of the compound 2 was conducted, to obtain a de-Fmoc form (3.25 g, q. y.).

The de-Fmoc form (2.05 g, 1.00 mmol) was dissolved in THF (18 mL) and DMF (2 mL), and Fmoc-Nle (6-OH)—OH (443 mg, 1.20 mmol, 1.2 equiv), DMT-MM (381 mg, 1.20 mmol, 1.2 equiv) and DIPEA (348 μL, 2.00 mmol, 2.0 equiv) were added and the mixture was stirred at room temperature for 30 minutes, then, evaporated under reduced pressure. The same post treatment as in synthesis of the compound 4 was conducted, to obtain a compound 119 (2.43 g, q. y.).

Synthesis of Compound 120

The compound 119 (1.18 g, 0.500 mmol) was dissolved in THF (9 mL) and DMF (1 mL), and piperidine (59.0 μL, 0.554 mmol, 1.1 equiv) and DBU (70.0 μL, 0.468 mmol, 0.94 equiv) were added and the mixture was stirred at room temperature for 5 minutes. The same post treatment as in synthesis of the compound 2 was conducted, to obtain a de-Fmoc form (1.05 g, 96.0%).

The de-Fmoc form (435 mg, 0.200 mmol) was dissolved in $CH_2Cl_2$ (4 mL), and $Boc_2O$ (65.0 mg, 0.298 mmol, 1.5 equiv) and $Et_3N$ (84.0 μL, 0.598 mmol, 3.0 equiv) were added and the mixture was stirred at room temperature for 1 hour. $Boc_2O$ (22.5 mg, 0.103 mmol, 0.52 equiv) was added and disappearance of starting materials was confirmed, then, this was evaporated under reduced pressure. The same post treatment as in synthesis of the compound 4 was conducted, to obtain a compound 120 (481 mg, q.y. %).

Synthesis of Compound 121

The compound 120 (218 mg, 0.0973 mmol) and $PPh_3$ (51.1 mg, 0.195 mmol, 2.0 equiv) were dissolved in toluene (28.5 mL), and DEAD (88.0 μL, 0.194 mmol, 2.0 equiv) was diluted with toluene (20 mL) and dropped over a period of 1 hour and the mixture was stirred at room temperature for 30 minutes. The same post treatment as in synthesis of the compound 4 was conducted to obtain a residue, which was then subjected to silica gel column chromatography ($CHCl_3$/EtOH, 100:0-90:10), to obtain a compound 121 (198 mg, 91.6%).

Synthesis of Compound 122

A compound 122 was obtained (q. y.) in the same manner as in the above-described synthesis example of the compound 16, excepting that the compound 121 was used as the starting material.

Synthesis of Bdev-31

Bdev-31 was obtained (77.1%) in the same manner as in the above-described synthesis example of Bdev-7, excepting that the compound 122 was used as the starting material. MS m/z [M+H]+: calcd for $C_{33}H_{53}N_{10}O_9$: 733.40. found 733.39.

Example 15

Synthesis of Bdev-32

The synthesis route of Bdev-32 is shown schematically in FIGS. 10 to 16.
Bdev-32 was synthesized as described below.

Synthesis of Compound 123

The compound 2 (2.55 g, 3.00 mmol) was dissolved in THF (54 mL) and DMF (6 mL), and Fmoc-Lys (Boc)-OH (1.69 g, 3.60 mmol, 1.2 equiv), HBTU (1.37 g, 3.60 mmol, 1.2 equiv), HOBt.H$_2$O (482 mg, 3.15 mmol, 1.05 equiv) and DIPEA (1568 µL, 9.00 mmol, 3.0 equiv) were added and the mixture was stirred at room temperature for 30 minutes, then, evaporated under reduced pressure. The same post treatment as in synthesis of the compound 4 was conducted on the residue, to obtain a compound 123 (3.80 g, q. y.).

Synthesis of Compound 124

A compound 124 was obtained (97.7%) in the same manner as in the above-described synthesis example of the compound 42, excepting that the compound 123 was used as the starting material and the amino acid to be condensed was changed to Fmoc-Ser(tBu)-OH.

Synthesis of Compound 125

A compound 125 was obtained in the same manner as in the above-described synthesis example of the compound 42, excepting that the compound 124 was used as the starting material and the amino acid to be condensed was changed to Fmoc-Leu-OH.

Synthesis of Compound 126

A compound 126 was obtained (83.7%, 7 steps from compound 2) in the same manner as in the above-described synthesis example of the compound 42, excepting that the compound 125 was used as the starting material and the amino acid to be condensed was changed to Boc-Gly-OH.

Synthesis of Compound 127

The compound 126 (3.66 g, 2.51 mmol) was dissolved in CH$_2$Cl$_2$ (126 mL), and TFE (13 mL) and TFA (1300 µL) were added and the mixture was stirred at room temperature for 30 minutes. The precipitated material was filtrated, to the filtrate was added DIPEA (2940 µL, 16.7 mmol), then, the mixture was evaporated under reduced pressure. To the residue was added water to find deposition of a precipitated material, which was then filtrated, and suspended and washed with water twice, to obtain a compound 127 (1.53 g, 84.9%).

Synthesis of Compound 128

A compound 128 was obtained (96.5%) in the same manner as in the above-described synthesis example of the compound 123, excepting that the amino acid to be condensed was changed to Fmoc-Phe-OH.

Synthesis of Compound 129

A compound 129 was obtained (99.3%) in the same manner as in the above-described synthesis example of the compound 42, excepting that the compound 128 was used as the starting material and the amino acid to be condensed was changed to Fmoc-Nle(6-OH)—OH.

Synthesis of Compound 130

A compound 130 was obtained (84.6%) in the same manner as in the above-described synthesis example of the compound 2, excepting that the compound 129 was used as the starting material.

Synthesis of Compound 131

The compound 130 (564 mg, 0.500 mmol) was dissolved in THF (9 mL) and DMF (1 mL), and the compound 127 (430 mg, 0.600 mmol, 1.2 equiv), DMT-MM (166 mg, 0.600 mmol, 1.2 equiv) and DIPEA (261 µL, 1.50 mmol, 3.0 equiv) were added and the mixture was stirred at room temperature for 30 minutes, then, evaporated under reduced pressure. The same post treatment as in synthesis of the compound 4 was conducted, to obtain a compound 131 (817 mg, 91.3%).

Synthesis of Compounds 132 to 137

Fmoc de-protection reaction: A Fmoc-protected peptide (1.0 equiv) was dissolved in THF (40 mL), and piperidine (1.3 equiv) and DBU (1.2 equiv) were added and the mixture was stirred at room temperature for 5 minutes. The same post treatment as in synthesis of the compound 2 was conducted, to obtain a de-Fmoc form.

Amino acid condensation reaction: The de-Fmoc form (1.0 equiv) was dissolved in THF (36 mL) and DMF (4 mL), and Fmoc-amino acid (1.2 equiv), HBTU (1.2 equiv), HOBt.H$_2$O (1.2 equiv) and DIPEA (3.6 equiv) were added and the mixture was stirred at room temperature for 30 minutes, then, evaporated under reduced pressure. The same post treatment as for synthesis of the compound 4 was conducted. Amino acid elongation was performed by the method as described above, to obtain a compound 137 (11.4 g, 86.4%, 14 steps from compound 131).

Synthesis of Compound 138

A compound 138 was obtained (98.4%) in the same manner as in the above-described synthesis example of the compound 127, excepting that the compound 137 was used as the starting material.

Synthesis of Compound 139

A compound 139 was obtained (q. y.) in the same manner as in the above-described synthesis example of the compound 123, excepting that the amino acid to be condensed was changed to Fmoc-Ser(tBu)-OH.

Synthesis of Compound 140

A compound 140 was obtained (99.6%, 3 steps from compound 2) in the same manner as in the above-described synthesis example of the compound 42, excepting that the compound 139 was used as the starting material and the amino acid to be condensed was changed to Fmoc-Met-OH.

Synthesis of Compound 141

A compound 141 was obtained (99.9%) in the same manner as in the above-described synthesis example of the compound 42, excepting that the compound 140 was used as the starting material.

Synthesis of Compound 142

A compound 142 was obtained (88.4%) in the same manner as in the above-described synthesis example of the compound 91, excepting that the compound 141 was used as the starting material.

Synthesis of Compound 143

A compound 143 was obtained (q. y.) in the same manner as in the above-described synthesis example of the compound 123, excepting that the amino acid to be condensed was changed to Fmoc-Leu-OH.

Synthesis of Compound 144

A compound 144 was obtained in the same manner as in the above-described synthesis example of the compound 2, excepting that the compound 129 was used as the starting material.

Synthesis of Compound 145

The compound 144 (1.35 g) was dissolved in THF (25 mL) and DMF (3 mL), and the compound 142 (1.27 g, 1.77 mmol), HATU (639 mg, 1.68 mmol), HOAt (200 mg, 1.47 mmol) and DIPEA (732 µL, 4.20 mmol) were added and the mixture was stirred at room temperature for 30 minutes. DIPEA (732 µL, 4.20 mmol) was added and disappearance of starting materials was confirmed, then, this was evaporated under reduced pressure. The same post treatment as in synthesis of the compound 4 was conducted on the residue, to obtain a compound 145 (1.98 g, q. y., 2 steps from compound 143).

Synthesis of Compound 146

A compound 146 was obtained (820 mg, q. y.) in the same manner as in the above-described synthesis example of the compound 91, excepting that the compound 145 was used as the starting material.

Synthesis of Compound 147

The compound 32 (701 mg, 0.484 mmol), the compound 131 (1.73 g, 0.968 mmol, 2.0 equiv) and PPh$_3$ (254 mg, 0.968 mmol, 2.0 equiv) were dissolved in THF (36 mL), and DEAD (1097 µL, 2.42 mmol, 5.0 equiv) was dissolved in THF (12 mL) and added over a period of 1 hour and the mixture was stirred at room temperature for 30 minutes. The same post treatment as in synthesis of the compound 4 was conducted to obtain a residue, which was then subjected to silica gel column chromatography (CHCl$_3$/THF, 100:0-75:25 and CHCl$_3$/THF, 100:0-80:20), to obtain a compound 147 (224 mg, 14.4%).

Synthesis of Compound 148

A compound 148 was obtained (57.1%) in the same manner as in the above-described synthesis example of the compound 2, excepting that the compound 145 was used as the starting material.

Synthesis of Compound 149

The compound 148 (120 mg, 0.0430 mmol) was dissolved in THF (776 µL) and DMF (86.0 µL), and the compound 146 (65.6 mg, 0.0741 mmol, 1.7 equiv), DMT-MM (17.1 mg, 0.0618 mmol, 1.4 equiv) and DIPEA (15.0 µL, 0.0861 mmol, 2.0 equiv) were added and the mixture was stirred at room temperature for 45 minutes. The mixture was stirred at 40° C. and disappearance of starting materials was confirmed, then, this was evaporated under reduced pressure. The same post treatment as in synthesis of the compound 4 was conducted, to obtain a compound 149 (138 mg, 84.2%).

Synthesis of Compound 150

A compound 150 was obtained (96.1%) in the same manner as in the above-described synthesis example of the compound 2, excepting that the compound 149 was used as the starting material.

Synthesis of Compound 151

The compound 150 (126 mg, 0.0350 mmol) was dissolved in THF (1.25 mL) and DMF (139 µL), and the compound 138 (75.6 mg, 0.0523 mmol, 1.5 equiv), DMT-MM (13.2 g, 0.0477 mmol, 1.4 equiv) and DIPEA (24.2 µL, 0.139 mmol, 4.0 equiv) were added and the mixture was stirred at room temperature for 35 minutes, then, this was evaporated under reduced pressure. The same post treatment as in synthesis of the compound 4 was conducted, to obtain a compound 151 (164 mg, 94.3%).

Synthesis of Compound 152

The compound 151 (164 mg, 0.0326 mmol) was dissolved in THF (1.8 mL) and DMF (196 µl), and piperidine (3.90 µl, 0.0366 mmol, 1.1 equiv) and DBU (9.20 µL, 0.0615 mmol, 1.9 equiv) were added and the mixture was stirred at room temperature for 5 minutes. DBU (3.00 µL, 0.0201 mmol) was added and disappearance of raw materials was confirmed, then, the same post treatment as in synthesis of the compound 2 was conducted, to obtain a de-Fmoc form (191 mg).

The de-Fmoc form was dissolved in CH$_2$Cl$_2$ (3.3 mL), and TEE (326 µL) and TEA (32.6 µL) were added and the mixture was stirred at room temperature for 15 minutes. The precipitated material was filtrated, to the filtrate was added DIPEA (76.5 µL, 0.439 mmol), then, this was evaporated under reduced pressure. To the residue was added water to find deposition of a precipitated material, which was then filtrated, and suspended and washed with water twice, to obtain a de-Kb form (114 mg).

The de-Kb form was dissolved in THF (5.0 mL) and DMF (560 µL), and DMT-MM (11.1 mg, 0.0401 mmol) and DIPEA (9.80 µL, 0.0563 mmol) were added and the mixture was stirred at room temperature for 2 hours, then, this was evaporated under reduced pressure. The same post treatment as in synthesis of the compound 4 was conducted, to obtain a compound 152 (110 mg, 83.7%, 3 steps from compound 151).

Synthesis of Compound 153

A compound 153 was obtained (98.2%) in the same manner as in the above-described synthesis example of the compound 16, excepting that the compound 152 was used as the starting material.

Synthesis of Bdev-32

To the compound 16 (103 mg, 0.0268 mmol) was added a solution (3 mL) of TFA/H$_2$O/PhOH/PhSMe/EDT=82.5/5/5/5/2.5 and the mixture was stirred at room temperature for 6 hours. The same post treatment as in synthesis of Bdev-7 was conducted, to obtain Bdev-32 (43.0 mg, 76.4%) as a crude product. MS m/z [M+H]$^+$: calcd for C$_{99}$H$_{171}$ N$_{28}$O$_{28}$S: 2232.25. found 2232.23.

Example 16

Synthesis of Bdev-33

The synthesis route of Bdev-33 is shown schematically in FIGS. 17 to 20.
Bdev-33 was synthesized as described below.

Synthesis of Compound 154

A compound 154 was obtained (q. y.) in the same manner as in the above-described synthesis example of the compound 1, excepting that the amino acid to be condensed was Fmoc-Leu-OH.

Synthesis of Compound 155

A compound 155 was obtained (99.8%) in the same manner as in the above-described synthesis example of the compound 42, excepting that the compound 154 was used as the starting material and the amino acid to be condensed was changed to Fmoc-Met-OH.

Synthesis of Compound 156

The compound 155 (1.67 g, 1.36 mmol) was dissolved in CH$_2$Cl$_2$ (136 mL), and TFE (13.6 mL) and TFA (1361 μL) were added and the mixture was stirred at room temperature for 30 minutes. The precipitated material was filtrated, to the filtrate was added DIPEA (3191 μL, 18.3 mmol), then, this was evaporated under reduced pressure. To the residue was added water for dilution, 1 N HClaq was added to attain pH4, and CH$_2$Cl$_2$ was added and extraction thereof was performed. The organic layer was washed with water three times, washed with saturated NaClaq, dried over MgSO$_4$, filtrated, and the filtrate was evaporated under reduced pressure. The residue was suspended and washed with n-hexane twice, to obtain a compound 156 (664 mg, q. y.).

Synthesis of Compound 157

A compound 157 was obtained (93.1%) in the same manner as in the above-described synthesis example of the compound 40, excepting that the amino acid to be condensed was Fmoc-Thr(tBu)-OH.

Synthesis of Compound 158

A compound 158 was obtained (92.2%) in the same manner as in the above-described synthesis example of the compound 42, excepting that the compound 157 was used as the starting material and the amino acid to be condensed was changed to Fmoc-Ser(tBu)-OH.

Synthesis of Compound 159

A compound 159 was obtained (94.9%) in the same manner as in the above-described synthesis example of the compound 42, excepting that the compound 158 was used as the starting material and the amino acid to be condensed was changed to Fmoc-Leu-OH.

Synthesis of Compound 160

A compound 160 was obtained (97.9%) in the same manner as in the above-described synthesis example of the compound 42, excepting that the compound 159 was used as the starting material and the amino acid to be condensed was changed to Fmoc-Asn(Trt)-OH.

Synthesis of Compound 161

A compound 161 was obtained (99.7%) in the same manner as in the above-described synthesis example of the compound 42, excepting that the compound 160 was used as the starting material and the amino acid to be condensed was changed to Fmoc-Gly-OH.

Synthesis of Compound 162

A de-Fmoc form was obtained in the same manner as in the above-described synthesis example of the compound 42, excepting that the compound 161 (2.11 g, 0.997 mmol) was used as the starting material.
The de-Fmoc form was dissolved in THF (18 mL) and DMF (2 mL), and Fmoc-Nle(6-OH)—OH (443 mg, 1.20 mmol), DMT-MM (381 mg, 1.38 mmol) and DIPEA (348 μL, 2.00 mmol) were added and the mixture was stirred at room temperature for 40 minutes, then, evaporated under reduced pressure. The same post treatment as in synthesis of the compound 4 was conducted, to obtain a compound 162 (2.29 g, q. y.).

Synthesis of Compound 163

A de-Fmoc form was obtained (1.07 g) in the same manner as in the above-described synthesis example of the compound 42, excepting that the compound 162 (1.13 g, 0500 mmol) was used as the starting material.
The de-Fmoc form was dissolved in CH$_2$Cl$_2$ (10 mL), and Boc$_2$O (218 mg, 0.999 mmol) and Et$_3$N (209 μL, 1.49 mmol) were added and the mixture was stirred at room temperature for 1 hour. Boc$_2$O (55.0 mg, 0.252 mmol) was added and disappearance of starting materials was confirmed, then, this was evaporated under reduced pressure. The same post treatment as in synthesis of the compound 4 was conducted, to obtain a compound 163 (1.16 g, q. y.).

Synthesis of Compound 164

A compound 164 was synthesized in the same manner as in the above-described synthesis example of the compound 121, excepting that the compound 163 was used as the starting material. The same post treatment as in synthesis of the compound 4 was conducted to obtain a residue, which was then subjected to silica gel column chromatography (CH$_2$Cl$_2$/THF, 100:0-65:35 and CH$_2$Cl$_2$/EtOH, 92:8), to obtain a compound 164 (26.9%).

Synthesis of Compound 165

The compound 164 (210 g, 0.0920 mmol) was dissolved in CH$_2$Cl$_2$ (10 mL), and TFE (1 mL) and TFA (92.0 μL) were added and the mixture was stirred at room temperature for 15 minutes. The precipitated material was filtrated, to the filtrate was added DIPEA (220 μL, 1.26 mmol), then, this was evaporated under reduced pressure. To the residue was added water to find deposition of a precipitated material, which was then filtrated, and suspended and washed with water twice, suspended and washed with IPE three times, to obtain a compound 165 (144 mg, q. y.).

Synthesis of Compound 166

A compound 166 was obtained (q. y.) in the same manner as in the above-described synthesis example of the compound 1, excepting that the amino acid to be condensed was Fmoc-Lys (Hoc)-OH.

Synthesis of Compounds 167 to 175

Fmoc de-protection reaction: A Fmoc-protected peptide (1.0 equiv) was dissolved in THF (40 mL), and piperidine (1.3 equiv) and DBU (1.2 equiv) were added and the mixture was stirred at room temperature for 5 minutes. The same post treatment as in synthesis of the compound 2 was conducted, to obtain a de-Fmoc form.

Amino acid condensation reaction: The de-Fmoc form (1.0 equiv) was dissolved in THF (36 mL) and DMF (4 mL), and Fmoc-amino acid (1.2 equiv), HBTU (1.2 equiv), HOBt.H$_2$O (1.2 equiv) and DIPEA (3.6 equiv) were added and the mixture was stirred at room temperature for 30 minutes, then, evaporated under reduced pressure. The same post treatment as for synthesis of the compound 4 was conducted. Amino acid elongation was performed by the method as described above, to obtain a compound 175 (5.03 g, 38.0%, 17 steps from compound 166).

Synthesis of Compound 176

The compound 175 (959 mg, 0.361 mmol) was dissolved in THF (6.8 mL), and the compound 156 (247 mg, 0.510 mmol, 1.4 equiv), DMT-MM (138 mg, 0.510 mmol, 1.4 equiv) and DIPEA (178 μL, 1.02 mmol, 2.8 equiv) were added and the mixture was stirred at room temperature for 30 minutes, then, evaporated under reduced pressure. The same post treatment as in synthesis of the compound 4 was conducted, to obtain a compound 176 (1.13 g, q. y.).

Synthesis of Compound 177

A compound 177 was obtained (91.2%) in the same manner as in the above-described synthesis example of the compound 2, excepting that the compound 176 was used as the starting material.

Synthesis of Compound 178

The compound 177 (243 mg, 0.0830 mmol) was dissolved in THF (1.5 mL) and DMF (170 μL), and the compound 165 (136 mg, 0.0993 mmol, 1.2 equiv), DMT-MM (28.0 mg, 0.101 mmol, 1.2 equiv) and DIPEA (28.9 μL, 0.166 mmol, 2.0 equiv) were added and the mixture was stirred at room temperature for 35 minutes, then, evaporated under reduced pressure. The same post treatment as in synthesis of the compound 4 was conducted, to obtain a compound 178 (298.2 mg, 85.2%).

Synthesis of Compound 179

A compound 179 was obtained (253 mg, 91.1%) in the same manner as in the above-described synthesis example of the compound 16, excepting that the compound 178 was used as the starting material.

Synthesis of Bdev-33

To the compound 179 (127 mg, 0.0316 mmol) was added a solution (3 mL) of TFA/H$_2$O/PhOH/PhSMe/EDT=82.5/5/5/5/2.5 and the mixture was stirred at room temperature for 3 hours. The same post treatment as in synthesis of Bdev-7 was conducted, to obtain Bdev-33 (55.6 mg, 86.7%). MS m/z [M+H]$^+$: calcd for $C_{89}H_{142}N_{23}O_{29}S$: 2029.01. found 2028.99.

As shown by these results, it is possible to introduce a cross-linkage of the present invention in place of the original disulfide bond into a cyclic peptide showing pharmacological activity, and as a result, a peptide having a novel cross-linkage structure can be synthesized.

Comparative Example

Synthesis of Comparative Compound

As a comparative compound, a W9 peptide (disulfide cross-linkage: compound number: STD) was used. The W9 peptide was prepared by condensing 2,4-docosyloxy benzyl alcohol with an amino acid successively, to synthesize a linear sequence, then, forming a disulfide bond by oxidation with iodine, and cleaving 2,4-docosyloxy benzyl alcohol by trifluoroacetic acid.

Reference Example

Synthesis of Reference Compound

Figure 21:
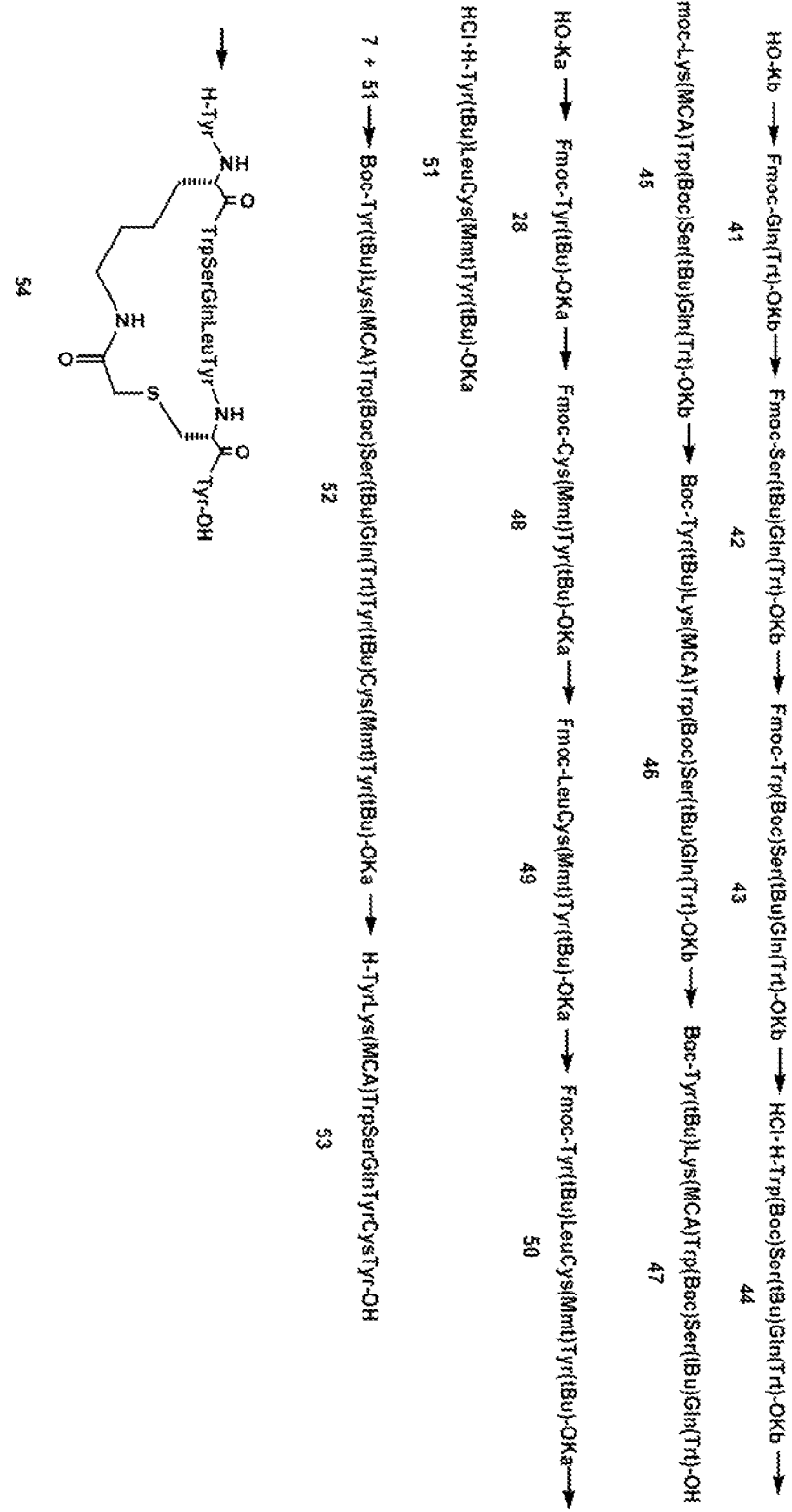
FIG. 21 shows a synthesis example of a W9 peptide mimic having a thioether cross-linkage as a reference example.
Figure 22:
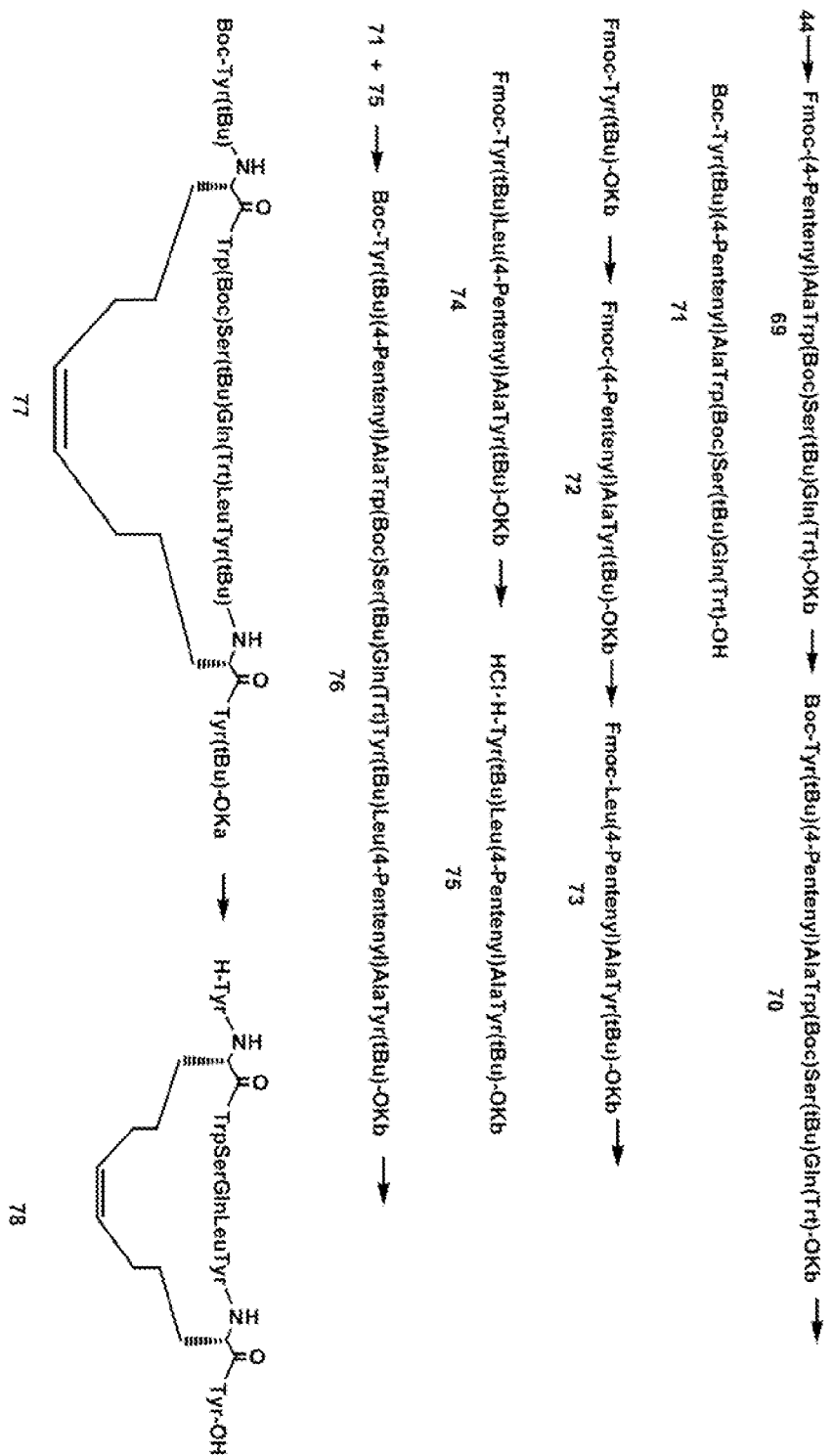
FIG. 22 shows a synthesis example of a W9 peptide mimic having an olefin cross-linkage as a reference example.

As a reference example, a modified body in which the cross-link portion had been converted into a thioether cross-linkage (compound number: Comp. 1) or an olefin cross-linkage (compound number: Comp. 3) was used. The thioether-cross-linked W9 peptide was synthesized according to a synthesis scheme described in FIG. 21. The olefin-cross-linked W9 peptide was synthesized according to a synthesis scheme described in FIG. 22.

Example 17

Resistance to Peptidase

Resistance to a peptidase of a peptide of the present invention was investigated using a carboxy peptidase and chymotrypsin. Resistance to a peptidase was measured as described below.

(Decomposition by Carboxy Peptidase)

A carboxy peptidase purchased from SIGMA was treated with PBS to prepare an enzyme solution of 1 U/ml, which was then kept warm at 37° C. in a water bath. Then, a peptide solution having a concentration adjusted to 5 mg/ml with DMSO: pure water=1:1 mixed solvent was treated with PBS (−) to obtain a concentration of 1 mg/ml, and the enzyme solution and the peptide solution were mixed at 4:1 so as to give a peptide final concentration of 0.2 mg/ml. Thereafter, these were reacted quickly at 37° C. With time, the reaction solution was sampled each in an amount of 0.1 ml, and a reaction stopping solution (25% TFA in acetonitrile, 20 μL) was added to stop the reaction. Samples were analyzed by HPLC, and decomposition of a peptide by the peptidase was measured. Sampling was conducted at 0, 0.5 minutes, 1 minute and 2 minutes, and when decomposition of 50% or more was not obtained at 2 minutes, sampling was conducted further at 0.5 hours, 1 hour, 3 hours, additionally, sometimes at 6 hours, and for peptides stable for a long period, sampling was conducted in a range of 24 hours to 168 hours according to demands. Time at which half of the peptide added was decomposed was measured. The results are shown in Table 3.

(Decomposition by Chymotrypsin)

Chymotrypsin purchased from SIGMA was treated with 0.1M Tris-HCl (pH8.0) to prepare an enzyme solution of 4 U/ml, which was then kept warm at 37° C. in a water bath. Then, a peptide solution treated with DMSO: pure water=1:1 to obtain a concentration of 5 mg/ml was treated with 0.1M Tris-HCl (pH8.0) to give a concentration of 1 mg/ml, and the enzyme solution and the peptide solution were mixed at 4:1 so as to give a peptide final concentration of 0.2 mg/ml. Thereafter, these were reacted quickly at 37° C. With time, the reaction solution was sampled each in an amount of 0.1 ml, and a reaction stopping solution (25% TFA in acetonitrile, 20 μL) was added to stop the reaction. Samples were analyzed by HPLC, and decomposition of a peptide by chymotrypsin was measured. Sampling was conducted at 0, 0.5 minutes, 1 minute and 2 minutes, and when decomposition of 50% or more was not obtained at 2 minutes, sampling was conducted further at 0.5 hours, 1 hour, 3 hours, and time at which half of the peptide added was decomposed was measured. The results are shown in Table 3.

TABLE 3

| compound number | structure pattern | $Z_1$ | $Z_3$ | $Z_2$ | half period by carboxy peptidase ($t^{1/2}$) | half period by chymotrypsin ($t^{1/2}$) |
|---|---|---|---|---|---|---|
| Bdev2 | P-1 | H | Ac | OH | 18.70 min | 1.40 min |
| Bdev3 | P-1 | Ac | PEG$_{2000}$ | OH | >7days | 5.19 hr |
| Bdev5 | P-1 | Ac | Ac | OH | 3.34 min | 0.39 min |
| Bdev6 | P-1 | Ac | H | OH | 2.47 min | 2.09 min |
| Bdev8 | P-1 | H | H | OH | 2.79 min | 1.26 min |
| Bdev10 | P-1 | PEG$_{2000}$ | Ac | OH | >7days | 58.28 min |
| Bdev13 | P-1 | Ac | Ac | PEG$_{2000}$ | >7days | 47.41 min |
| Bdev-19 | P-2 | H | Ac | OH | 2.97 min | 0.97 min |
| Bdev-20 | P-2 | H | PEG$_{2000}$ | OH | 59.60 min | 3.6 min |
| Bdev-21 | P-3 | H | Ac | OH | 14.60 min | 0.95 min |
| Bdev-25 | P-4 | H | Ac | OH | 2.63 min | 1.85 min |
| Bdev-27 | P-1 | H | —(C=O)-Ethyl | OH | 14.99 min | 4.37 min |
| Bdev-28 | P-1 | H | —(C=O)—n-Butyl | OH | 21.67 min | 2.90 min |
| Bdev-29 | P-1 | H | —(C=O)CH$_2$CH$_2$(OCH$_2$)$_3$OMe | OH | 15.67 min | 3.73 min |
| Bdev-30 | P-1 | H | —(C=O)CH$_2$CH$_2$(OCH$_2$)$_7$OMe | OH | 19.22 min | 3.66 min |
| STD | | | SS cross-linkage | | 0.45 min | 0.40 min |
| Comp. 1 | | | Thioether cross-linkage | | 0.72 min | 0.45 min |
| Comp. 3 | | | Olefin cross-linkage | | 3.29days | 2.07 min |

The above-described results teach that a W9 peptide mimic of the present invention fabricated according to the cross-linking method of the present invention shows improved decomposition resistance to a peptidase, as compared with a W9 peptide containing a disulfide cross-linkage or a thioether cross-linkage.

The above detailed descriptions are provided only for explaining the object and the subject of the present invention, and dot not limit the scope of the appended claims. Various changes and substitutions for the described embodiments are apparent for those skilled in the art based on teachings described in the present specification, without deviating from the scope of the appended claims.

INDUSTRIAL APPLICABILITY

The present invention provides a cross-linked peptide containing a novel nonpeptidic cross-linked structure, and a method for synthesizing the same. Such a cross-linked peptide is useful since it can manifest various improved natures.

The invention claimed is:

1. A cross-linked peptide represented by the following formula P-1:

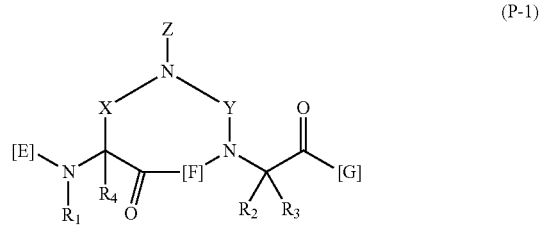

(P-1)

wherein,

X is any one selected from the group consisting of the following formulae X-1 to X-7:

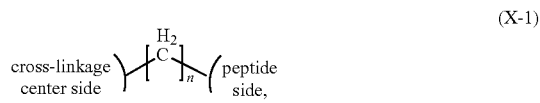

(X-1)

-continued

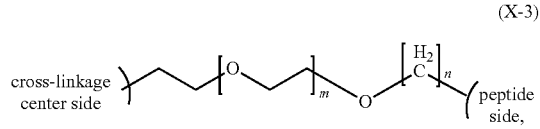

(X-2)

(X-3)

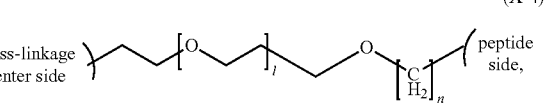

(X-4)

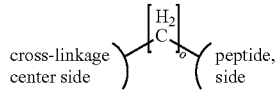
(Y1-1)

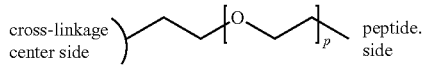
(Y1-2)

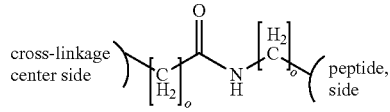
(Y2-1)

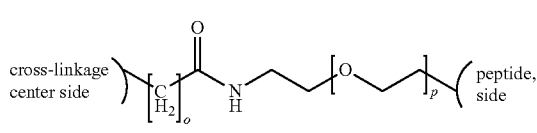
(Y2-2)

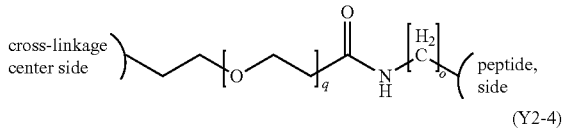
(Y2-3)

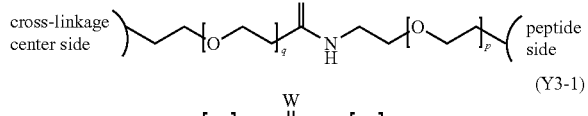
(Y2-4)

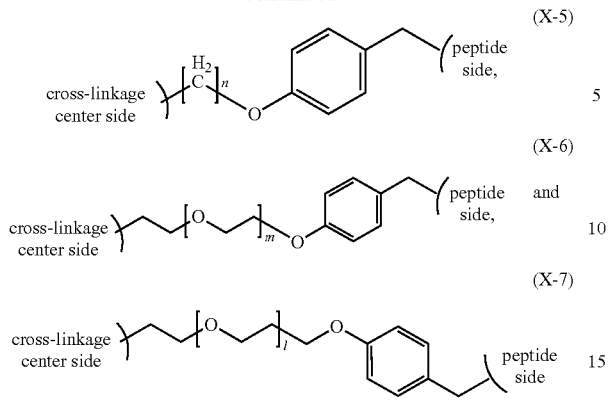

(X-5)

(X-6) and (X-7)

wherein,
n represents an integer of 1 to 12,
m represents an integer of 1 to 24 and
l represents an integer of 1 to 24,
Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom,
Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group,
[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and
$R_1$, $R_3$ and $R_4$ represent each independently a hydrogen atom or a methyl group, and
$R_2$ represents a hydrogen atom or a side chain of an amino acid or unnatural amino acid.

2. A cross-linked peptide represented by the following formula P-1:

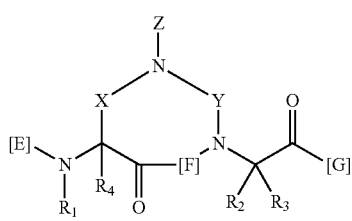

(P-1)

wherein,
X represents an alkylene chain having 1 to 12 carbon atoms or an alkylene chain having 1 to 66 carbon atoms containing at least one —O— or —S-bond,
Y is any one selected from the group consisting of the following compounds Y1-1 to Y1-2, Y2-1 to Y2-4, Y3-1 to Y3-9, Y4-1 to Y4-5, and Y5:

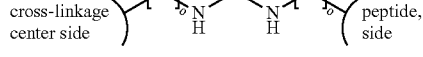
(Y3-1)

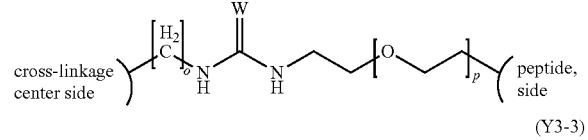
(Y3-2)

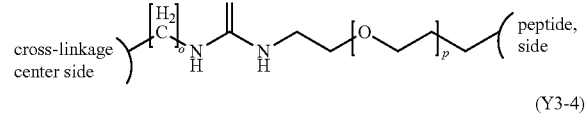
(Y3-3)

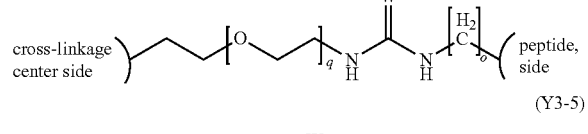
(Y3-4)

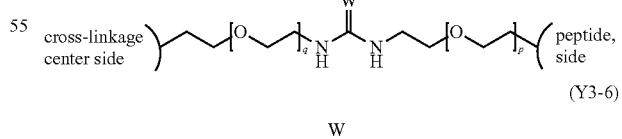
(Y3-5)

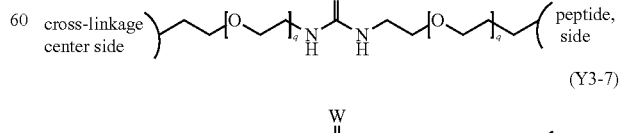
(Y3-6)

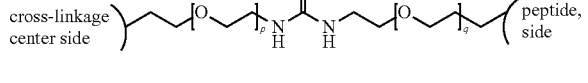
(Y3-7)

(Y3-8)

cross-linkage center side —[O]ₚ—CH₂—NH—C(W)—NH—[O]ₚ— peptide side (Y3-9)

cross-linkage center side —[O]ₚ—CH₂—NH—C(W)—NH—[CH₂]ₒ— peptide side (Y4-1)

cross-linkage center side —[CH₂]ₒ—[O—CH₂]ₒ— peptide side (Y4-2)

cross-linkage center side —[CH₂]ₒ—[O]ₚ— peptide side (Y4-3)

cross-linkage center side —[CH₂]ₒ—[O]_q— peptide side (Y4-4)

cross-linkage center side —[O]ₚ—O—[CH₂]ₒ— peptide side (Y4-5)

cross-linkage center side —[O]_q—O—[CH₂]ₒ— peptide side (Y5)

cross-linkage center side —[H]—S—[I]— peptide side wherein, [H] is represented by any one of the following formulae H1 to H3: or (H1)

cross-linkage center side —[CH₂]ₒ—

(H2)

cross-linkage center side —[O]_q— , or (H3)

cross-linkage center side —[O]ₚ— and

[I] is represented by any one of the following formulae I1 to I3:

(I1)

—[CH₂]ₛ— peptide side, (I2)

—[O]ᵣ— peptide side, or (I3)

—[J]—NH—C(=O)—[K]— peptide side wherein, [J] is represented by any one of the following formulae J1 to J2:

(J1)

—[CH₂]ₜ—C(=O)— , or (J2)

—[O]ᵣ— and

[K] is represented by any one of the following formulae K1 to K3:

(K1)

—[CH₂]ₒ— , (K2)

—[O]_q— , or (K3)

—[O]_u— , and o represents an integer of 1 to 12,
p represents an integer of 1 to 27,
q represents an integer of 1 to 24,
r represents an integer of 1 to 8,
s represents an integer of 1 to 16,
t represents an integer of 1 to 15,
u represents an integer of 1 to 11, and
W represents O or S,
Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group,
[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and
$R_1$, $R_3$ and $R_4$ represent each independently a hydrogen atom or a methyl group, and
$R_2$ represents a hydrogen atom or a side chain of an amino acid or unnatural amino acid.

3. The cross-linked peptide according to claim 1, wherein
n represents an integer of 1 to 7,
m represents an integer of 1 to 11, and
l represents an integer of 1 to 12, and
Y is any one selected from the group consisting of the following compounds Y1-1 to Y1-2, Y2-1 to Y2-4, Y3-1 to Y3-9, Y4-1 to Y4-5, and Y5:
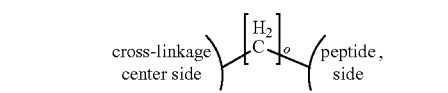
(Y1-1)
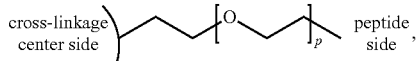
(Y1-2)
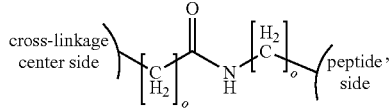
(Y2-1)
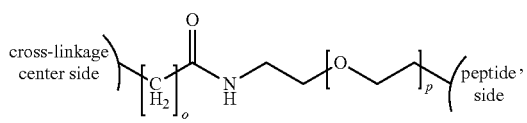
(Y2-2)
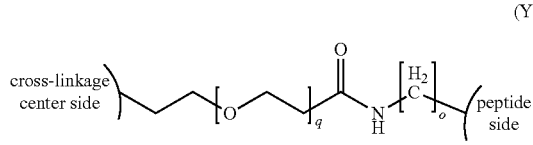
(Y2-3)
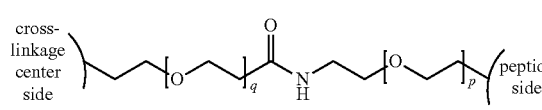
(Y2-4)
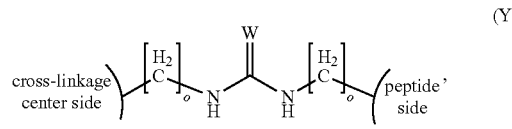
(Y3-1)
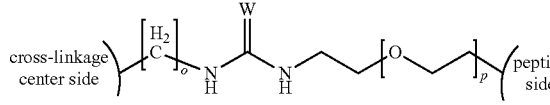
(Y3-2)
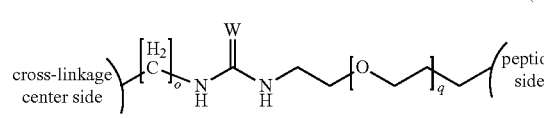
(Y3-3)
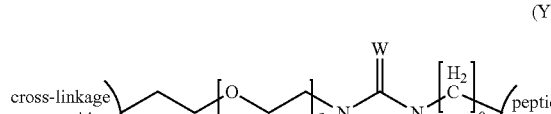
(Y3-4)
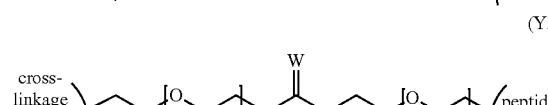
(Y3-5)
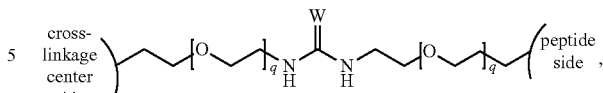
(Y3-6)
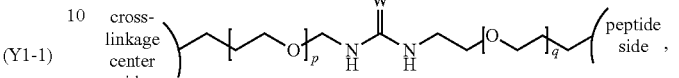
(Y3-7)
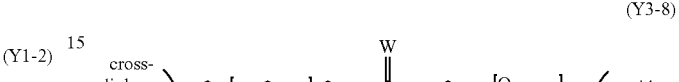
(Y3-8)
(Y3-9)
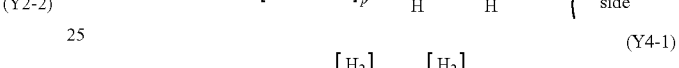
(Y4-1)
(Y4-2)
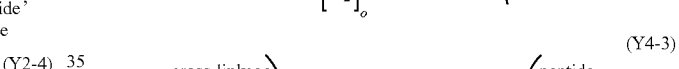
(Y4-3)
(Y4-4)
(Y4-5)
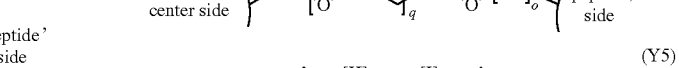
(Y5)
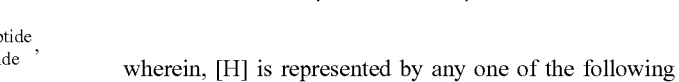
wherein, [H] is represented by any one of the following formulae H1 to H3:
or
(H1)
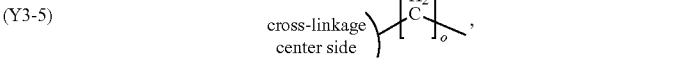
(H2)
, or -continued

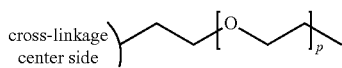  (H3)

[I] is represented by any one of the following formulae 11 to 13:

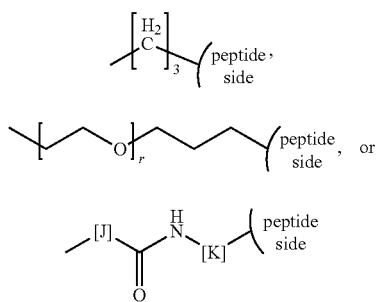

wherein, [J] is represented by any one of the following formulae J1 to J2:

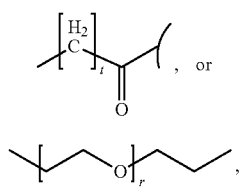

and

[K] is represented by any one of the following formulae K1 to K3:

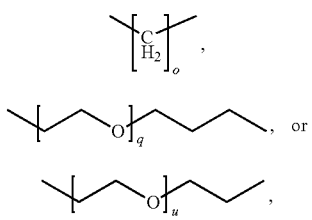

and wherein o represents an integer of 1 to 8,
p represents an integer of 1 to 11,
q represents an integer of 1 to 12,
r represents an integer of 1 to 8,
s represents an integer of 1 to 16,
t represents an integer of 1 to 15,
u represents an integer of 1 to 11, and
W represents 0 or S.

4. A cross-linked peptide represented by the following formula P-1:

  (P-1)

wherein

Z is an acyl group having 1 to 8 carbon atoms, an unsubstituted or substituted alkyl group having 1 to 8 carbon atoms, polyethylene glycol having a molecular weight of 100 to 10000 Da represented by —C(=O)—CH$_2$CH$_2$ (OCH$_2$CH$_2$)$_n$OCH$_2$CH$_2$OCH$_3$ or any one selected from the group consisting of the following formulae Z-1 to Z-5:

  (Z-1)

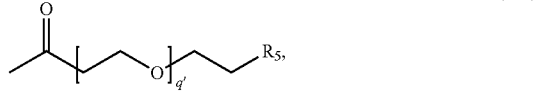  (Z-2)

  (Z-3)

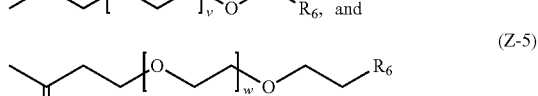  (Z-4)

  (Z-5)

wherein, n represents an integer of 1 to 12,
q' represents an integer of 1 to 12,
v represents 1 or 2,
w represents an integer of 1 to 12,
R$_5$ is any one selected from the group consisting of the following formulae R5-1 to R5-5:

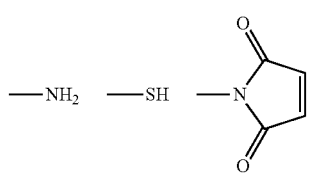

-continued

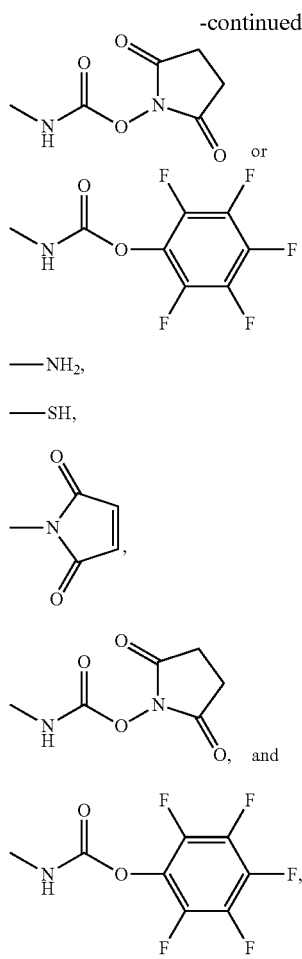

(R5-1) —NH₂,
(R5-2) —SH,
(R5-3)
(R5-4)
(R5-5)

and,
R₆ is any one selected from the group consisting of the following formulae R6-1 to R6-5:

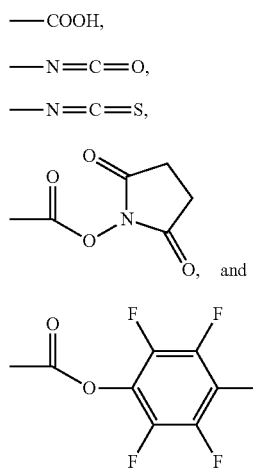

(R6-1) —COOH,
(R6-2) —N=C=O,
(R6-3) —N=C=S,
(R6-4)
(R6-5)

X represents an alkylene chain having 1 to 12 carbon atoms or an alkylene chain having 1 to 66 carbon atoms containing at least one —O— or —S-bond,
Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom,

[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and
R₁, R₃ and R₄ represent each independently a hydrogen atom or a methyl group, and
R₂ represents a hydrogen atom or a side chain of an amino acid or unnatural amino acid.

5. A cross-linked peptide represented by the following formula P-1:

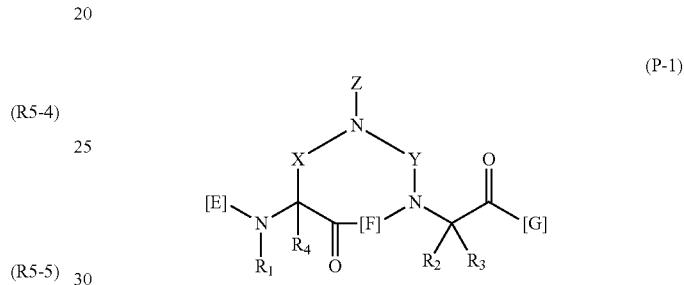

(P-1)

wherein
each of [E] and [G] represents a peptide having at least one amino acid or unnatural amino acid and
[F] represents a peptide having at least two amino acids or unnatural amino acids,
X represents an alkylene chain having 1 to 12 carbon atoms or an alkylene chain having 1 to 66 carbon atoms containing at least one —O— or —S-bond,
Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom,
Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group, and
R₁, R₃ and R₄ represent each independently a hydrogen atom or a methyl group, and
R₂ represents a hydrogen atom or a side chain of an amino acid or unnatural amino acid.

6. A cross-linked peptide represented by the following formula P-2:

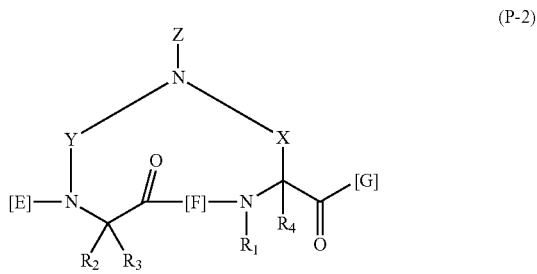

(P-2)

wherein
X is any one selected from the group consisting of the following formulae X-1 to X-7:

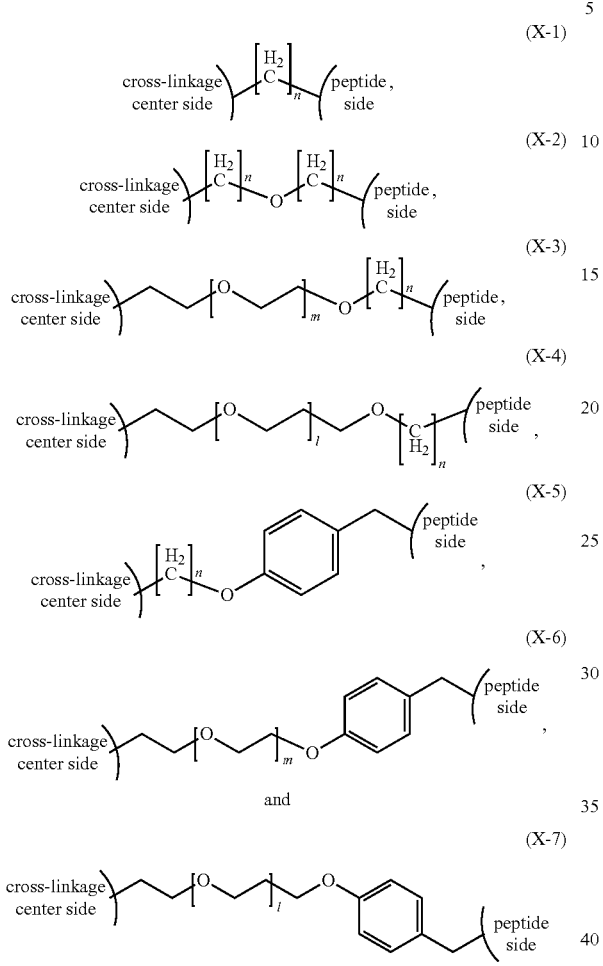

wherein,
n represents an integer of 1 to 12,
m represents an integer of 1 to 24, and
l represents an integer of 1 to 24,
Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom,
Z represents hydrogen, an optionally substituted alkyl group having 1 to 30 carbon atoms, an optionally substituted acyl group having 1 to 36 carbon atoms, polyethylene glycol, a tBoc group a Fmoc group, a Cbz group or a Nosyl group,
[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and $R_1$, $R_3$ and $R_4$ represent each independently a hydrogen atom or a methyl group, and
$R_2$ represents a hydrogen atom or a side chain of an amino acid or unnatural amino acid.

7. A cross-linked peptide represented by the following formula P-2:

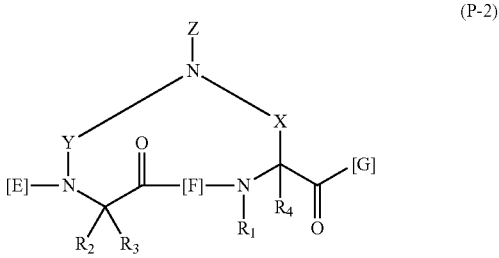

wherein
X represents an alkylene chain having 1 to 12 carbon atoms or an alkylene chain having 1 to 66 carbon atoms containing at least one —O— or —S-bond,
Y is any one selected from the group consisting of the following compounds Y1-1 to Y1-2, Y2-1 to Y2-4, Y3-1 to Y3-9, Y4-1 to Y4-5, and Y5:

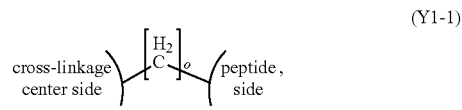

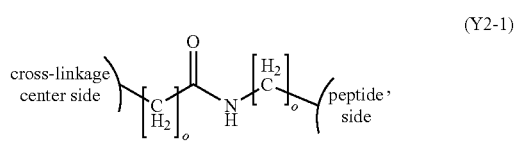

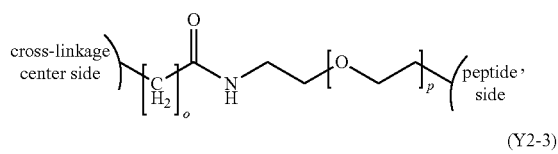

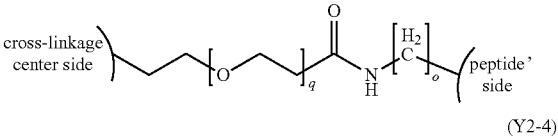

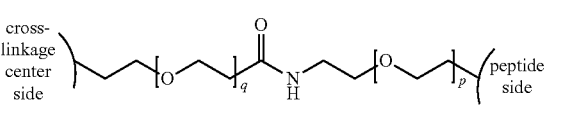

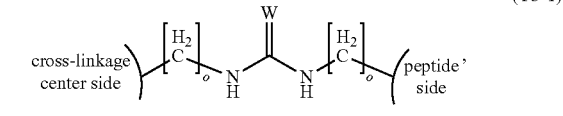

-continued
(Y3-2)
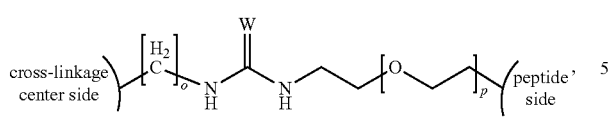
(Y3-3)
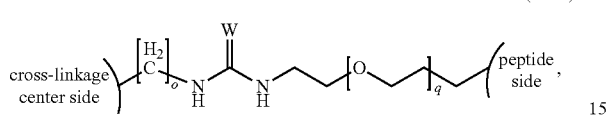
(Y3-4)
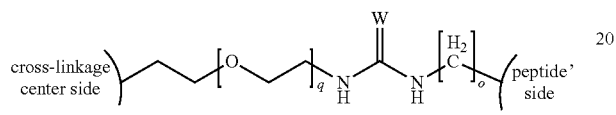
(Y3-5)
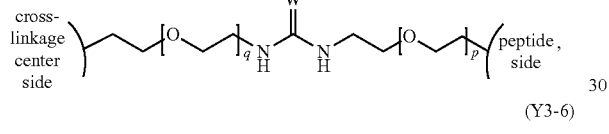
(Y3-6)
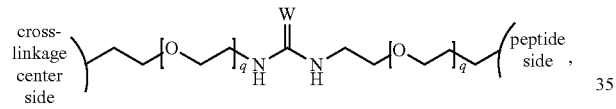
(Y3-7)
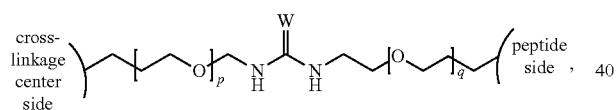
(Y3-8)
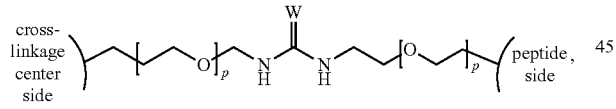
(Y3-9)
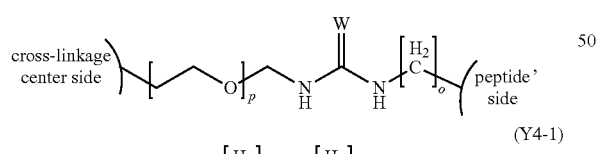
(Y4-1)
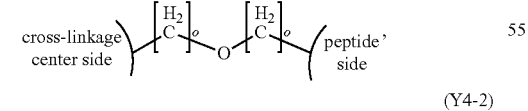
(Y4-2)
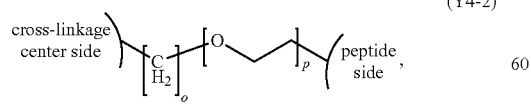
(Y4-3)
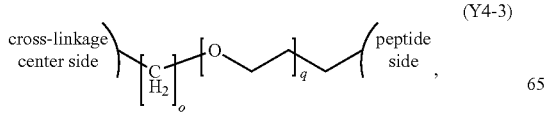
-continued
(Y4-4)
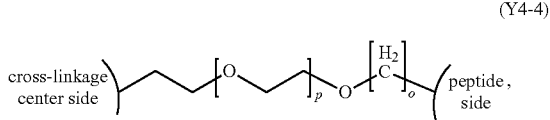
(Y4-5)
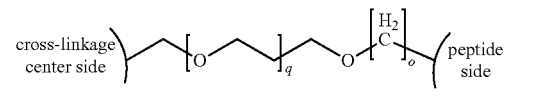
(Y5)
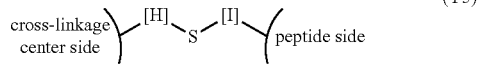
wherein, [H] is represented by any one of the following formulae H1 to H3:
(H1)
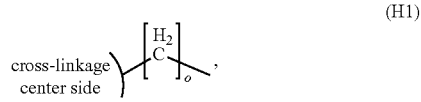
(H2)
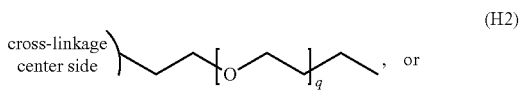
(H3)
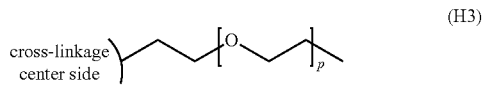
and
[I] is represented by any one of the following formulae 11 to 13:
(I1)
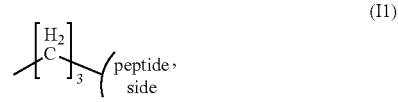
(I2)
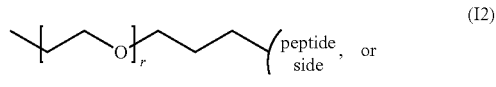
(I3)
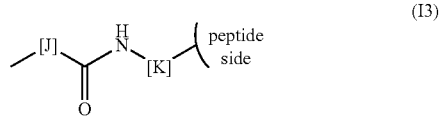
wherein, [J] is represented by any one of the following formulae J1 to J2:
(J1)

-continued

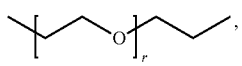 (J2)

and

[K] is represented by any one of the following formulae K1 to K3:

 (K1)

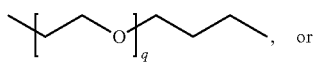 (K2)

, or

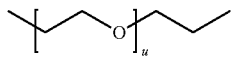 (K3)

and o represents an integer of 1 to 12,
p represents an integer of 1 to 27,
q represents an integer of 1 to 24,
r represents an integer of 1 to 8,
s represents an integer of 1 to 16,
t represents an integer of 1 to 15,
u represents an integer of 1 to 11, and
W represents 0 or S,
Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group,
[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and
$R_1$, $R_3$ and $R_4$ represent each independently a hydrogen atom or a methyl group, and
$R_2$ represents a hydrogen atom or a side chain of an amino acid or unnatural amino acid.

8. The cross-linked peptide according to claim 6, wherein
n represents an integer of 1 to 7,
m represents an integer of 1 to 11,
l represents an integer of 1 to 12, and
Y is any one selected from the group consisting of the following compounds Y1-1 to Y1-2, Y2-1 to Y2-4, Y3-1 to Y3-9, Y4-1 to Y4-5, and Y5:

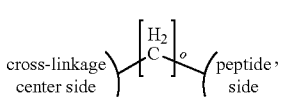 (Y1-1)

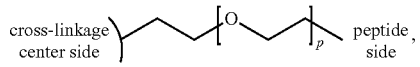 (Y1-2)

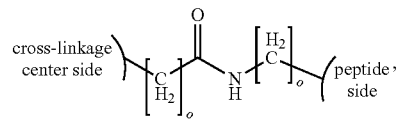 (Y2-1)

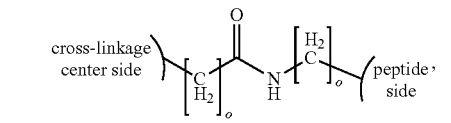 (Y2-2)

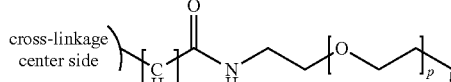 (Y2-3)

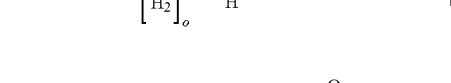 (Y2-4)

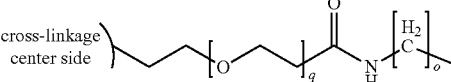 (Y3-1)

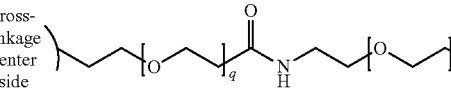 (Y3-2)

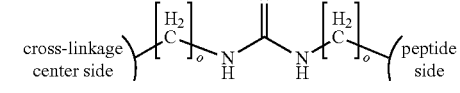 (Y3-3)

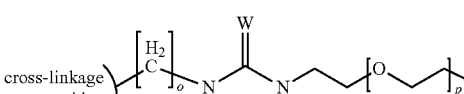 (Y3-4)

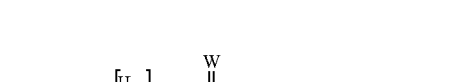 (Y3-5)

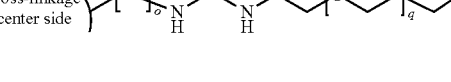 (Y3-6)

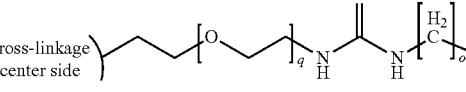 (Y3-7)

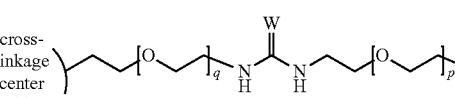

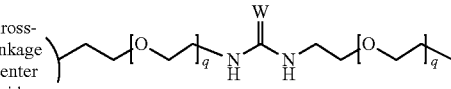

-continued (Y3-8)

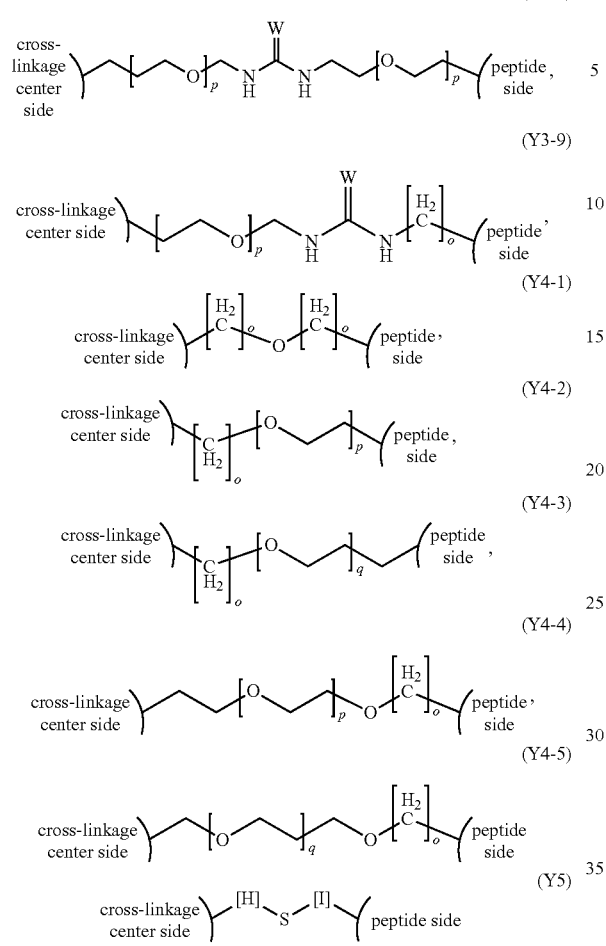

(Y3-9)

(Y4-1)

(Y4-2)

(Y4-3)

(Y4-4)

(Y4-5)

(Y5)

wherein, [H] is represented by any one of the following formulae H1 to H3:

or (H1)

(H2)

(H3)

and

[I] is represented by any one of the following formulae I1 to I3:

(I1)

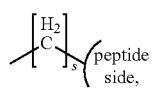

-continued (I2)

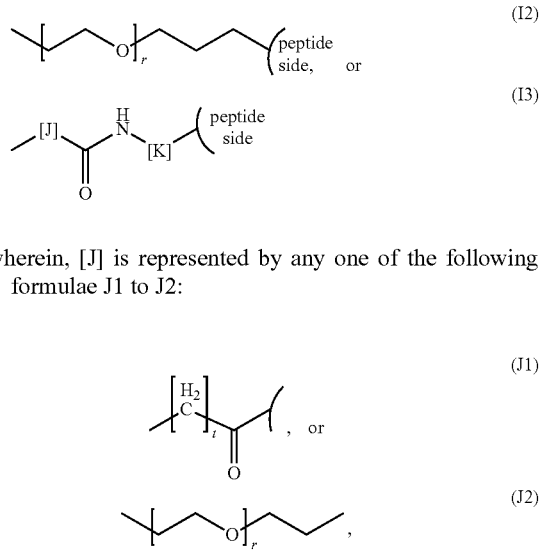

(I3)

wherein, [J] is represented by any one of the following formulae J1 to J2:

(J1)

(J2)

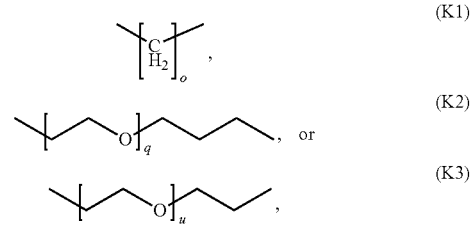

and

[K] is represented by any one of the following formulae K1 to K3:

(K1)

(K2)

(K3)

and wherein
o represents an integer of 1 to 8,
p represents an integer of 1 to 11,
q represents an integer of 1 to 12,
r represents an integer of 1 to 8,
s represents an integer of 1 to 16,
t represents an integer of 1 to 15,
u represents an integer of 1 to 11, and
W represents O or S.

9. A cross-linked peptide represented by the following formula P-2:

(P-2)

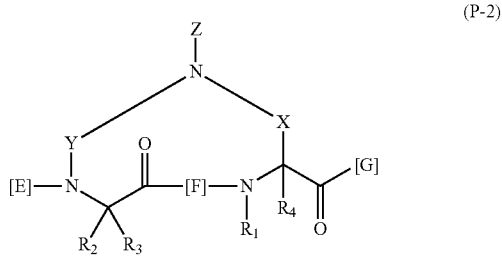

wherein
Z is an acyl group having 1 to 8 carbon atoms, an unsubstituted or substituted alkyl group having 1 to 8 carbon atoms, polyethylene glycol having a molecular weight of 100 to 10000 Da represented by —C(═O)—CH$_2$CH$_2$(OCH$_2$CH$_2$)$_n$ OCH$_2$CH$_2$OCH$_3$ or any one selected from the group consisting of the following formulae Z-1 to Z-5:

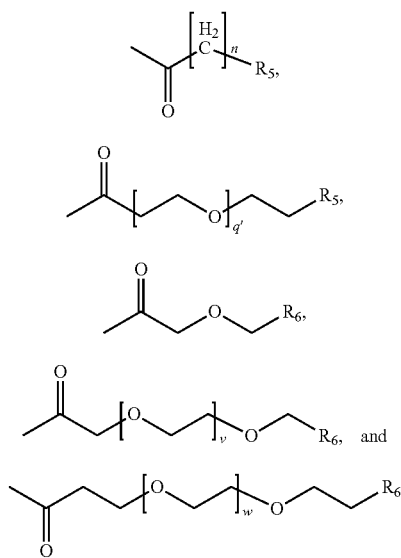

wherein
n represents an integer of 1 to 12,
q' represents an integer of 1 to 12,
v represents 1 or 2,
w represents an integer of 1 to 12,
R$_5$ is any one selected from the group consisting of the following formulae R5-1 to R5-5:

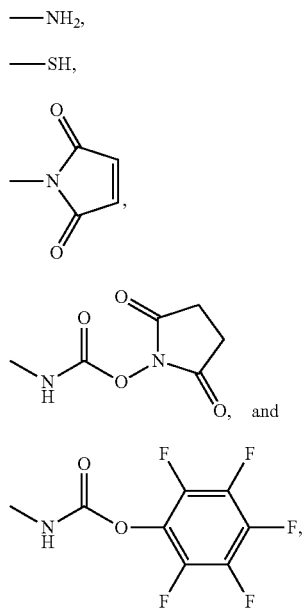

and
R$_6$ is any one selected from the group consisting of the following formulae R6-1 to R6-5:

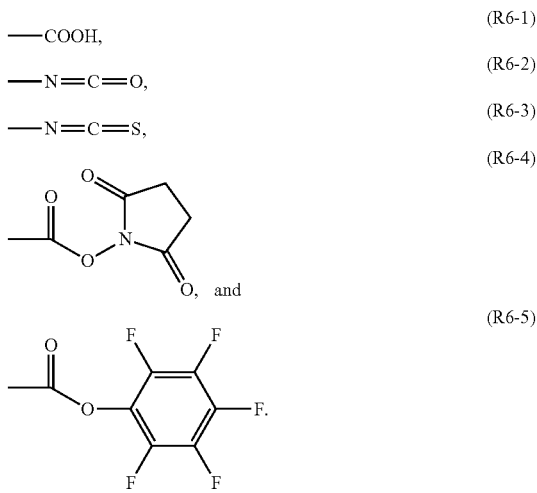

X represents an alkylene chain having 1 to 12 carbon atoms or an alkylene chain having 1 to 66 carbon atoms containing at least one —O— or —S-bond,
Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom,
[E] represents a hydrogen atom, an optionally substituted acyl group having 1 to 6 carbon atoms or a peptide having 1 to 20 residues composed of amino acids or unnatural amino acids as constituent elements,
[F] represents a peptide having 1 to 20 residues composed of amino acids or unnatural amino acids,
[G] represents OH, an amino group or a peptide having 1 to 20 residues composed of amino acids or unnatural amino acids,
the sum of the numbers of amino acids of [E], [F] and [G] is at least 3, and
R$_1$, R$_3$ and R$_4$ represent each independently a hydrogen atom or a methyl group, and
R$_2$ represents a hydrogen atom or a side chain of an amino acid or unnatural amino acid.

10. A cross-linked peptide represented by the following formula P-2:

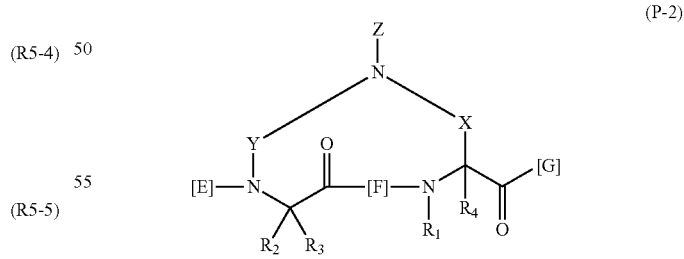

wherein
each of [E] and [G] represent a peptide having at least one amino acid or unnatural amino acid and
[F] represents a peptide having at least two amino acids or unnatural amino acids,
X represents an alkylene chain having 1 to 12 carbon atoms or an alkylene chain having 1 to 66 carbon atoms containing at least one —O— or —S-bond, Y represents an alkylene chain having 1 to 12 carbon atoms or an alkylene chain having 1 to 66 carbon atoms containing at least one —O—, —NH— or —S-bond and optionally substituted by a divalent oxygen atom or sulfur atom, Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group, $R_1$, $R_3$ and $R_4$ represent each independently a hydrogen atom or a methyl group, and $R_2$ represents a hydrogen atom or a side chain of an amino acid or unnatural amino acid.

11. A method of synthesizing a cross-linked peptide represented by the following formula:

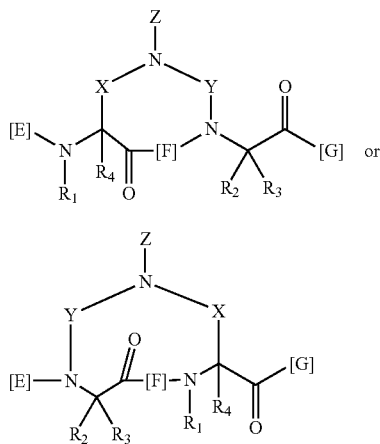

wherein,

X and Y represent each independently an alkylene chain having 1 to 12 carbon atoms or an alkylene chain having 1 to 66 carbon atoms containing at least one —O—, —NH— or —S— bond and optionally substituted by a divalent oxygen atom or sulfur atom, Z represents hydrogen, an optionally substituted alkyl group having 1 to 30 carbon atoms, an optionally substituted acyl group having 1 to 36 carbon atoms, polyethylene glycol, a tBoc group, a Fmoc group, a Cbz group or a Nosyl group,

[E] represents a hydrogen atom, an acetyl group or a peptide having 1 to 20 residues composed of amino acids or unnatural amino acids,

[G] represents OH, an amino group or a peptide having 1 to 20 residues composed of amino acids or unnatural amino acids,

[F] represents a peptide having 1 to 20 residues composed of amino acids or unnatural amino acids, the sum of the numbers of amino acids of [E], [F] and [G] is at least 3, $R_1$, $R_3$ and $R_4$ represent each independently a hydrogen atom or a methyl group, and $R_2$ represents a hydrogen atom or a side chain of an amino acid or unnatural amino acid, comprising the following steps:

(a) a step of preparing a first component, comprising the following steps, (a-1) a step of reacting the N-terminus side of the peptide or amino acid synthesized or the carboxyl protective group with an amino acid derivative containing in the side chain a linker forming part of a cross-linkage of the cross-linked peptide, to synthesize the peptide having the linker in the side chain or the amino acid derivative having the carboxyl group protected, (a-2) when the linker end is not reactive in the following step c of the cross-linkage forming reaction, a step of converting the linker end into a reactive functional group, (b) a step of preparing a second component, comprising the following steps, (b-1) a step of condensing a carboxyl protective group with amino acids or a peptide constituting a partial peptide sequence of the cross-linked peptide, (b-2) a step of reacting the N-terminus of the peptide or the amino acid derivative synthesized with a compound containing a linker forming part of a cross-linkage of the cross-linked peptide, to synthesize a peptide or an amino acid derivative having a secondary amine at the N-terminus containing the linker, (b-3) when the linker end is not reactive in the following step c of the cross-linkage forming reaction, a step of converting the linker end into a reactive functional group, (c) a step of linking the first component and the second component by the Mitsunobu reaction, a reductive amination reaction or the Aza-Wittig reaction and the subsequent reduction reaction, to prepare an intermediate having a structure in which the two components are linked via a secondary amine or a tertiary amine, and (d) a step of condensing the peptide N- or C-terminus of one component with the peptide C- or N-terminus of another component.

12. A method of synthesizing the cross-linked peptide according to claim 11, wherein the step (c) is carried out under a condition in which at least one of the first component and the second component is linked to the carboxyl protective group of a peptide support, wherein the peptide support is an alkoxy substituted benzyl selected from the group consisting of a 2,4-substituted benzyl alcohol, a 3,5-substituted benzyl alcohol, a 3,4,5-substituted benzyl alcohol and a 2,4,5-substituted benzyl alcohol.

13. The method of synthesizing the cross-linked peptide according to claim 12, wherein the number of carbon atoms of the alkoxy substituent of the 2,4-substituted benzyl alcohol is 1 to 60.

* * * * *